US011597914B2

(12) United States Patent
Jang et al.

(10) Patent No.: US 11,597,914 B2
(45) Date of Patent: Mar. 7, 2023

(54) IGG TYPE MONOCLONAL ANTIBODIES SPECIFICALLY BINDING TO ODONTOBLAST SURFACE

(71) Applicant: Dankook University Cheonan Campus Industry Academic Cooperation Foundation, Chungcheongnam-do (KR)

(72) Inventors: Young Joo Jang, Seoul (KR); Kyung Jung Kang, Chungcheongnam-do (KR)

(73) Assignee: Dankook University Cheonan Campus Industry Academic Cooperation Foundation, Chungcheongnam-Do (KR)

( * ) Notice: Subject to any disclaimer, the term of this patent is extended or adjusted under 35 U.S.C. 154(b) by 777 days.

(21) Appl. No.: 16/097,837

(22) PCT Filed: Dec. 21, 2017

(86) PCT No.: PCT/KR2017/015269
§ 371 (c)(1),
(2) Date: May 2, 2019

(87) PCT Pub. No.: WO2018/124642
PCT Pub. Date: Jul. 5, 2018

(65) Prior Publication Data

US 2019/0249145 A1 Aug. 15, 2019

(30) Foreign Application Priority Data

Dec. 26, 2016 (KR) ........................ 10-2016-0179277
Dec. 1, 2017 (KR) ........................ 10-2017-0164380
Dec. 1, 2017 (KR) ........................ 10-2017-0164410

(51) Int. Cl.

| | |
|---|---|
| ***C12N 5/077*** | (2010.01) |
| ***C07K 16/28*** | (2006.01) |
| ***C07K 16/18*** | (2006.01) |
| ***C12N 5/0775*** | (2010.01) |
| ***G01N 33/53*** | (2006.01) |
| ***A61K 35/32*** | (2015.01) |
| ***C12N 5/074*** | (2010.01) |
| ***G01N 33/50*** | (2006.01) |

(52) U.S. Cl.
CPC ............ *C12N 5/0654* (2013.01); *A61K 35/32* (2013.01); *C07K 16/18* (2013.01); *C07K 16/28* (2013.01); *C12N 5/0607* (2013.01); *C12N 5/0664* (2013.01); *G01N 33/5073* (2013.01); *G01N 33/53* (2013.01); *C07K 2317/56* (2013.01); *C07K 2317/565* (2013.01); *C12N 2501/115* (2013.01); *C12N 2501/15* (2013.01); *C12N 2501/155* (2013.01); *C12N 2506/1361* (2013.01)

(58) Field of Classification Search
None
See application file for complete search history.

(56) References Cited

PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*

* cited by examiner

*Primary Examiner* — Adam Weidner
(74) *Attorney, Agent, or Firm* — Wood, Phillips, Katz, Clark & Mortimer

(57) ABSTRACT

The present invention relates to a composition for the differentiation of dental pulp stem cells into odontoblasts and an IgG or IgM type monoclonal antibody that specifically binds to the surface of odontoblasts differentiated from the stem cells. According to the present invention, BMP2 and BMP4 are optimally combined to significantly increase the differentiation efficiency of dental pulp stem cells into odontoblasts, to induce the mineralization of the matrix, and to improve the differentiation ability of odontoblasts into dentin. Further, the IgG or IgM monoclonal antibody that specifically binds to the surface of odontoblasts of the present invention is used to effectively isolate and purify odontoblasts, which can be useful for tissue regeneration and differentiation.

14 Claims, 9 Drawing Sheets

Specification includes a Sequence Listing.

[FIG. 1]
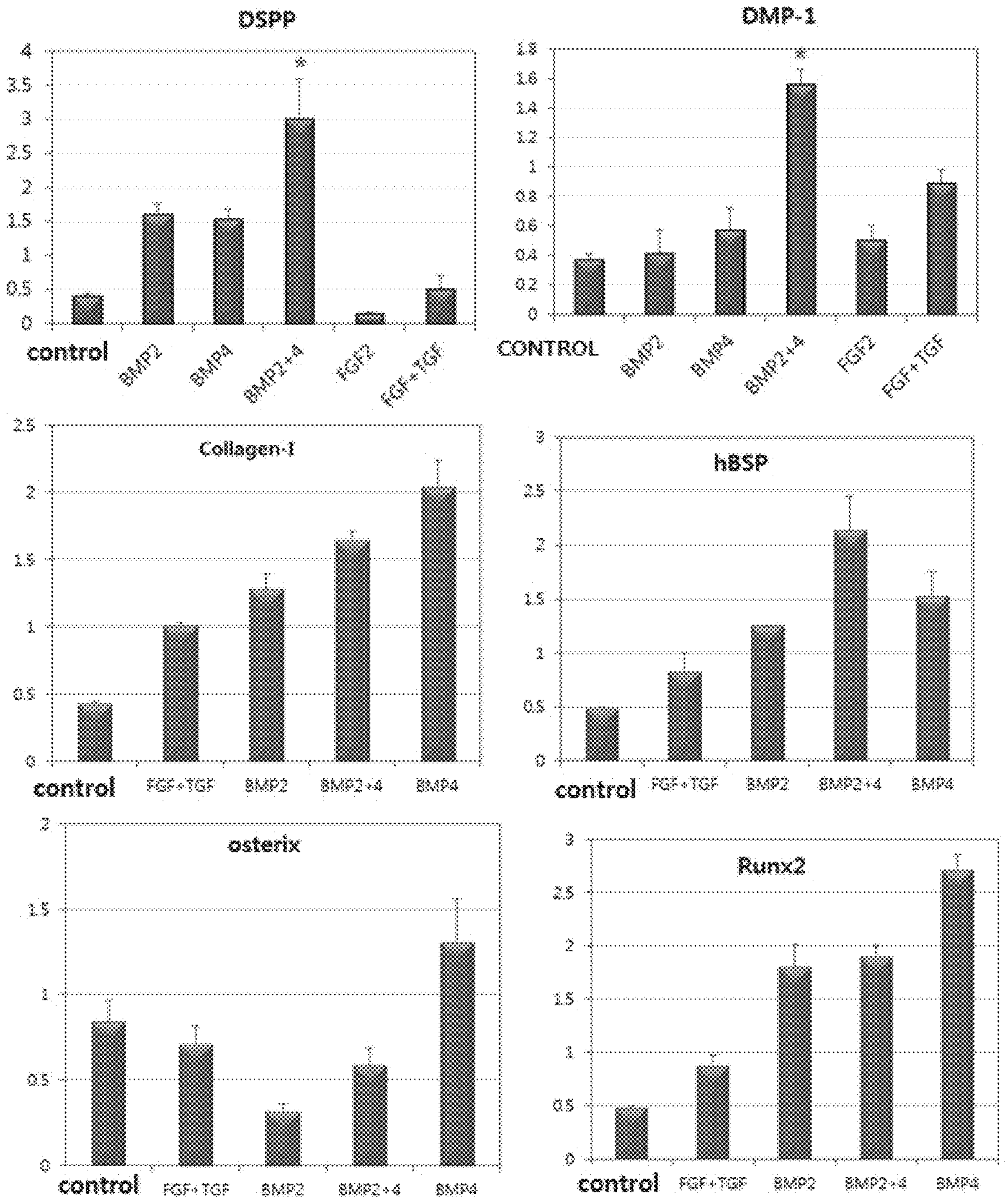

[FIG. 2]
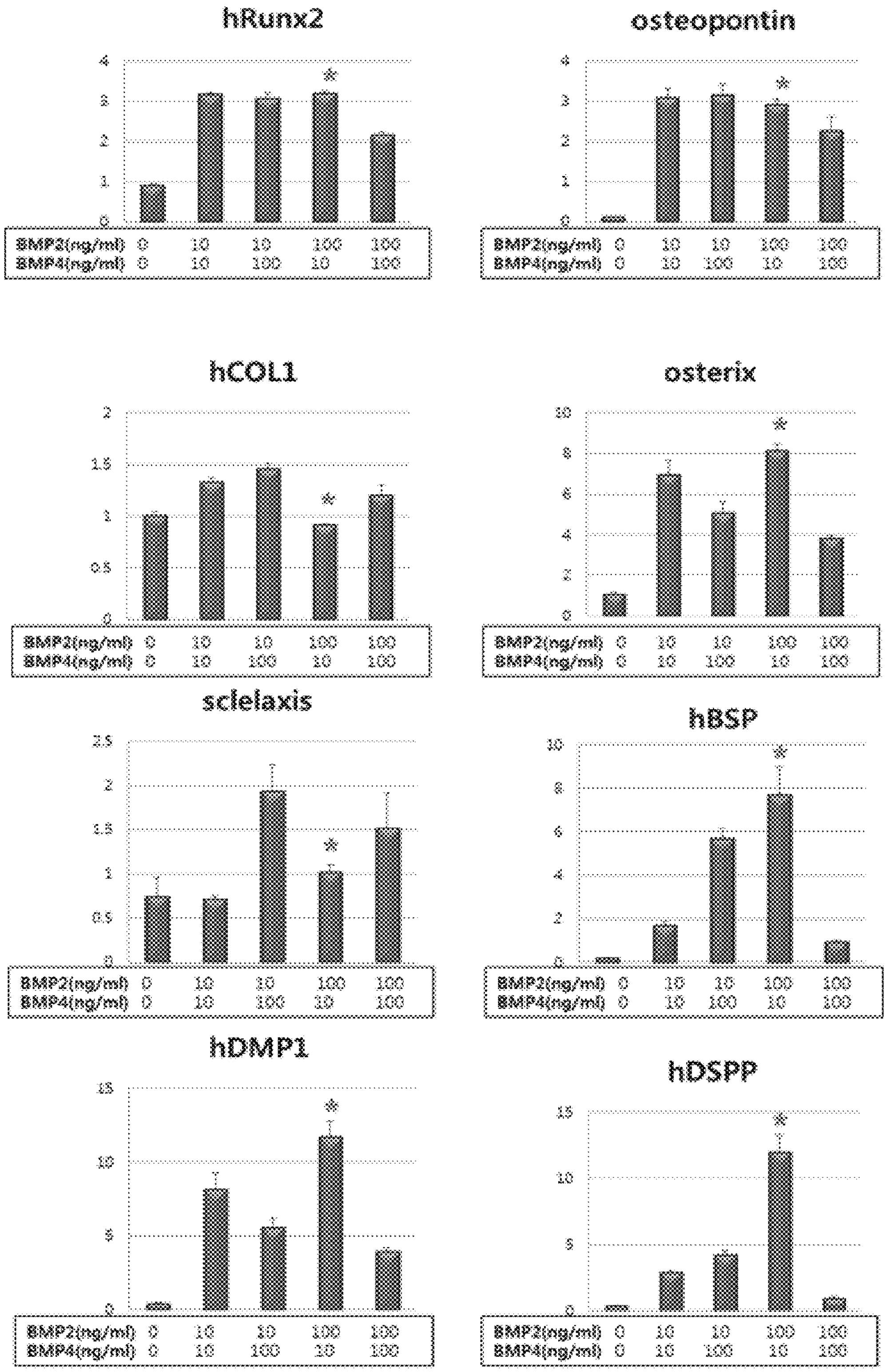

[FIG. 3]
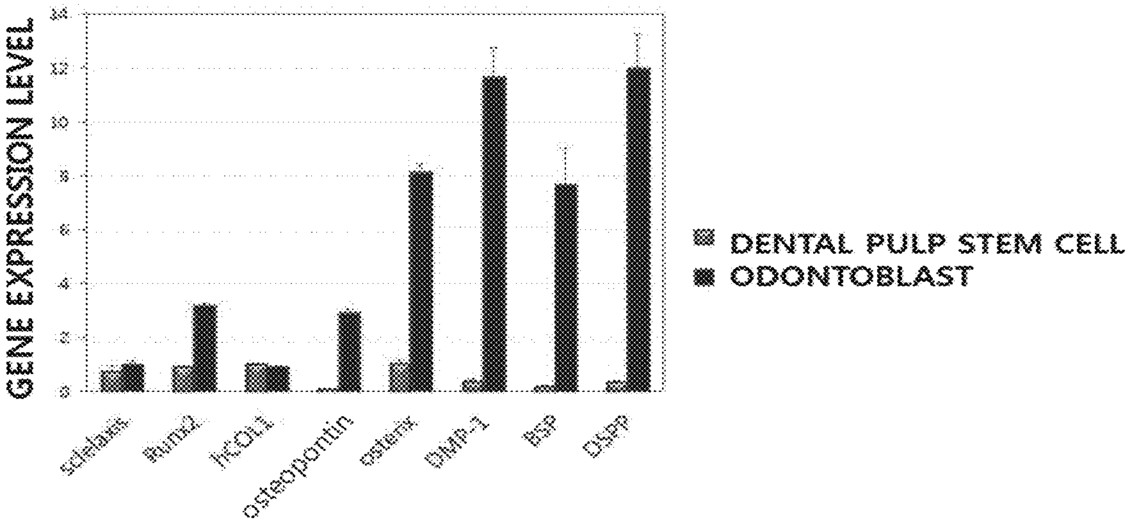
[FIG. 4]
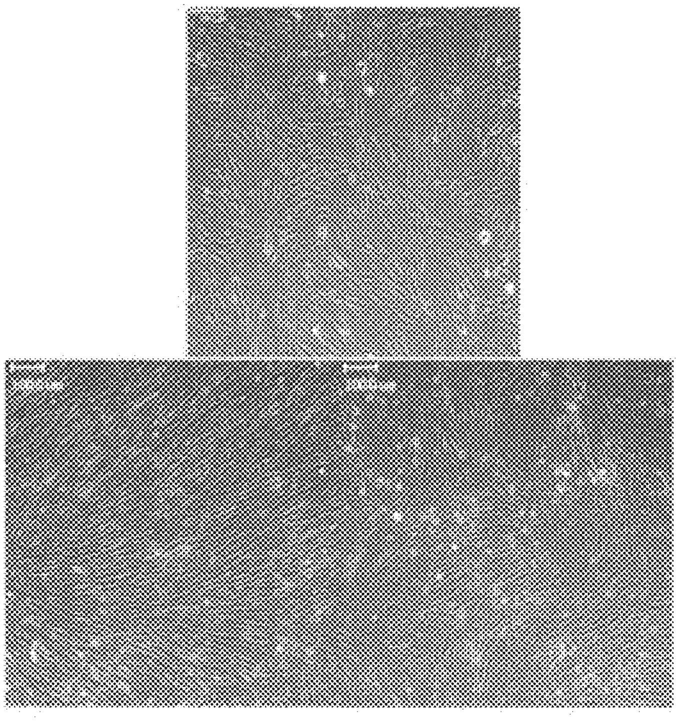

[FIG. 5]
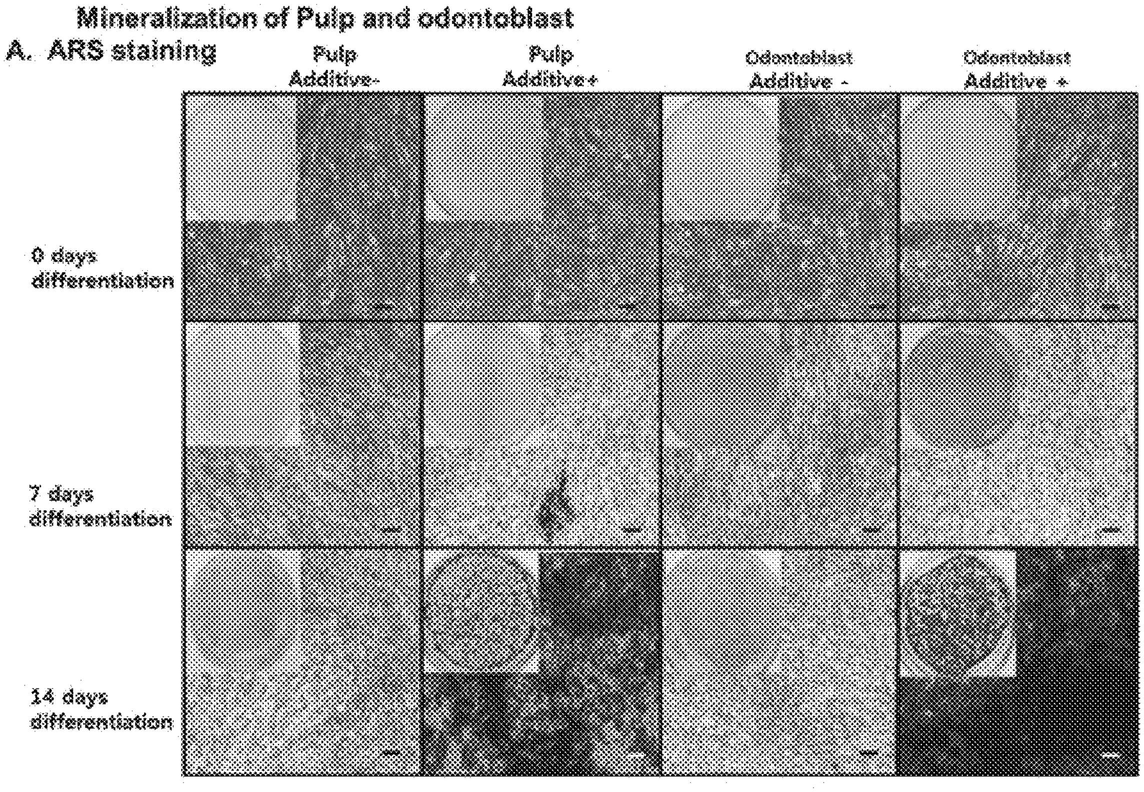
[FIG. 6]
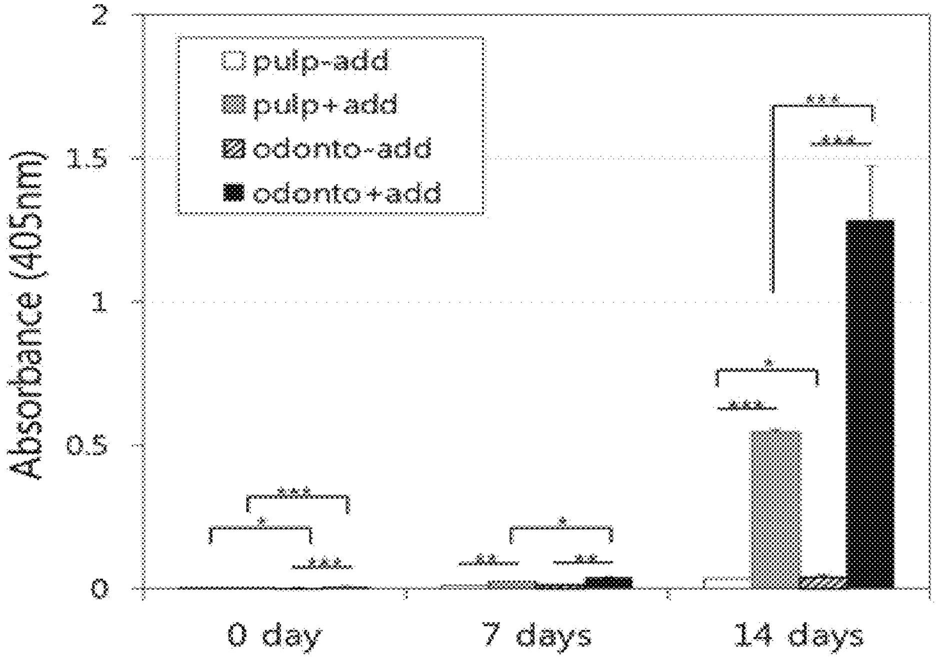

[FIG. 7]
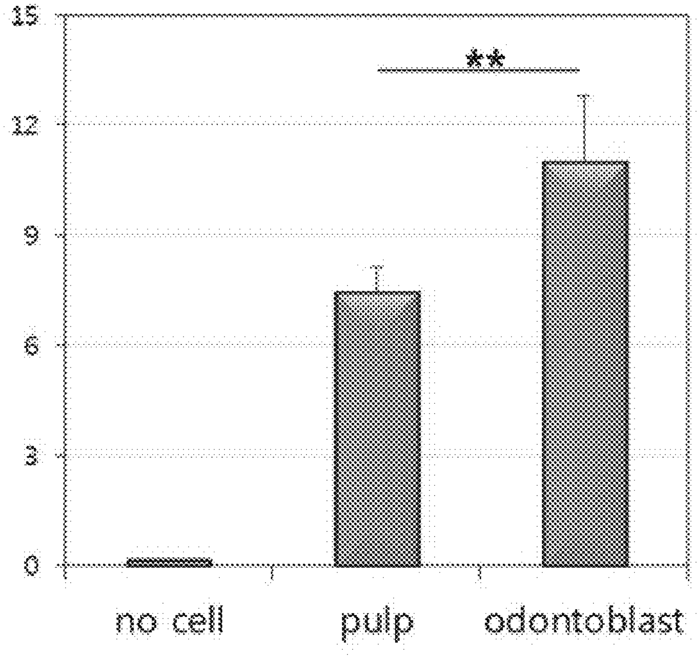
[FIG. 8]
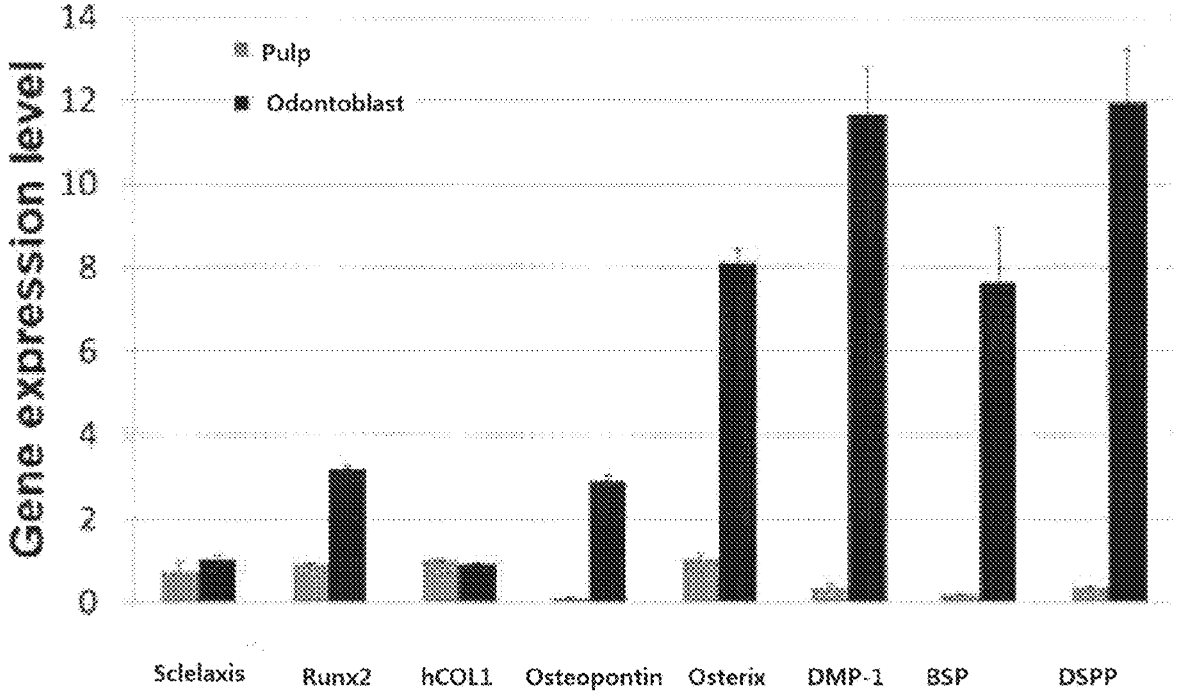

[FIG. 9]
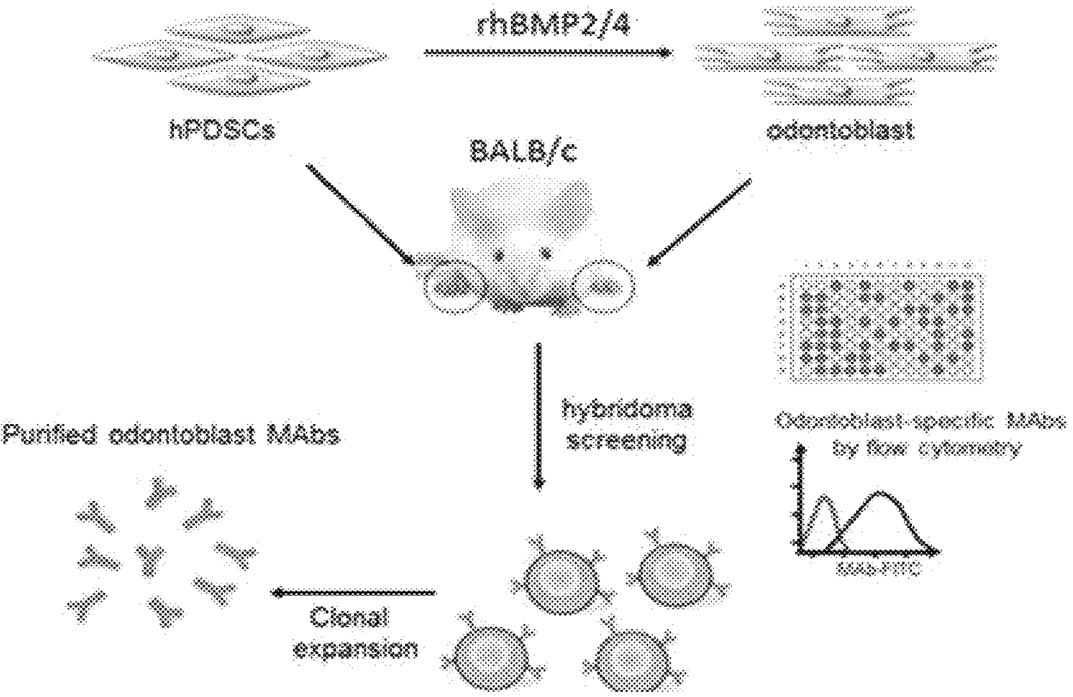

[FIG. 10]

a. IgG Light chain variable region

| | | ------CDR-L1------ | | ---CDR-L2--- | | ------CDR-L3------ | | |
|---|---|---|---|---|---|---|---|---|
| OD 40 | FRKLDIQLTQSPASLSVSVGETVTITC | RASENIYSHLA---------- | WYQEKQGKSPQLLVY | AATNLAD | GVPSRFSGSGSGTIYSLKINRLQSEDFGSYYC | QHFWGTLPT- | FGGGPSEKSG | SEQ ID NO. 73 |
| OD 46 | -RKLDIQLTQSPSSLAMSVGQKVTMSC | KSSQSLLNSSNQKNYLA | WYQQKPGQSPKLLVY | FASPISKO | GVPDRFIGSGSGTDFTLTISSVQAEDLADYFC | QQHYTTPWT- | FGGGTKLNQTG | SEQ ID NO. 75 |
| OD 82B | FRKLDIQLTQSPALMSASPGEKVTMTC | SASSSVSYMN------------ | WYQQKPRSSPKPWIY | LTSNLAS | GVPARFSGSGSGTSYSLTISNMEAEDAATYYC | QQSWSNPLT- | FGAGPS | SEQ ID NO. 77 |
| OD 142B | --------DIQLTQSPKFLLVSAGDRVTITC | KASQSVSNDVA---------- | WYQQKPGQSPKLLIY | YASNRYT | GVPDRFTGSGYGTDFTFTINTMQAEDLAVYFC | QQDYSSPYT- | FGGGTKLEIKRADAAPTVS | SEQ ID NO. 79 |
| OD 142D | FRKLDIQLTQSPSSLAMSVGQKVTMSC | KSSQSLLNSSNQKNYLA | WYQQKPGQSPKLLVY | FASARKS | GVPDRFIGSGYGTDFTLTISSVQAEDLADYFC | QQHYTTPWT- | FGGGTKLNQAG | SEQ ID NO. 81 |
| OD 149A | -RKLDIQLTQSPKFMSTSVGDRVSVTC | KASQNVGTNVA---------- | WYQQKPGQSPKALIY | SASYRYS | GVPDRFTGSGSGTDFTLTISNVQSEDLAEYFC | QQYNSYPLT- | FGAGPS | SEQ ID NO. 83 |
| OD 218A | YRKLDIQLTQSPAILSAFPGEKVTMTC | RASSSVSYMN------------ | WYQQKPGSSPKPWIY | ATSNLAS | GVPARFSGSGSGASYSLTISRVEAEDAATYYC | QQWSSNPPYT | FGGGPS | SEQ ID NO. 85 |
| OD 218B | --------HSADPVSKFMSTSVGDRVSITC | KASQDVSTTVA---------- | WYQQKPGQSPKLLIY | WASTRHT | GVPDRFTGSGSGTDYSLTISSVQAEDLALYYC | QQHYSTPYT- | FGGGTKLEIKRADAAPTVS | SEQ ID NO. 87 |
| OD 228 | -------DIVLTQSPASLAVSAGEKVTMSC | KSSQSVLYSSNQKNYLA | WYQQKPGQSPKLLIY | WASTRES | GVPDRFTGSGSGTDFTLTISSVQAEDLAVYYC | HQYLSWT--- | FGGGTKLEIKRADAAPTVS | SEQ ID NO. 89 |
| OD 238 | SFKLDIQLTQSPSSLAMSVGQKVTMSC | KSSQSLLNSSNQKNYLA | WYQQKPGQSPKLLVY | FASXRKS | GVPDRFIGSGSGTDFTLTISSVQAEDLADYFC | QQHYTTPWT- | FGGGTKLNQSWM | SEQ ID NO. 91 |
| OD 243A | ---------DIQLTQSPSSLSASLGDRVTISC | RASLDISNYLN---------- | WYQQKPDGTVKLLIY | YTSRLHS | GVPSRFSGSGSGTDYSLTISNLDQEDFATYFC | QQGNTLPWT- | FGGGTKLEIKRADAAPTVS | SEQ ID NO. 93 |
| OD 256 | ----------DIQLTQSPLSLPVSLGDQASISC | RSSQSLVHSNGNTYLH- | WYLQKPGQSPKLLIY | KVSNRFS | GVPDRFNGSGSGTDFTLKISRVEAEDLGVYFC | SQSTHVPFT- | FGSGTELEIKRADAAPTVS | SEQ ID NO. 95 |

b. IgG Heavy chain variable region

| | | -------CDR-H1------- | | ------------CDR-H2------------ | | ----------CDR-H3---------- | | |
|---|---|---|---|---|---|---|---|---|
| OD 40 | FRKFEVQLQESGPGILQPSQTLSLTCSFS | GFSLSTYGIGVG | WIRQPSGKGLEWLA | HIWWNDNKYYNTALKS-- | RLTISKDISNNQVFLKIVSVDTADTATYYCAR- | ILMLRRFMDY---------- | WGQGTSVIVSS | SEQ ID NO. 74 |
| OD 46 | FRKIEVQLQQSGAELVRPGSSVKISCKAS | GYAFSSYWMN- | WVKQRPGQGLEWIG | QIYPGDGDSNYNGKFKG-- | KATLTADKSSSIAYMQLSSLTSEDSAVYFCARF | GSTATADY-------------- | WGQGTTLTVSSA | SEQ ID NO. 76 |
| OD 82B | LPEFQVQLEQSGAELAKPGASVKMSCKAS | GYTFASYWMH- | WMKQRPGQGLEWIG | YINPSTVYTEYNQKFKD-- | KASLTADTSSSTAYMQLSSLTSEDSAVYYCAR- | SRYDGFAY-------------- | WGQGTLVTSPA | SEQ ID NO. 78 |
| OD 142B | FRNFEVQLQQSGGGLVKPGGSLKLSCAAS | GFTFSSYAMS-- | WVRQTPEKRLEWVA | TISSGGSYTYYPDSVKG-- | RFTISRDNAKNTLYLQMSSLRSEDTAMYYCAR- | RSYDGGGVWFAY------ | WGQGTLVTSL | SEQ ID NO. 80 |
| OD 142D | FRKFEVQLQQSGGGLVKPGGSLKLSCAAS | GFTFSSYAMS-- | WVRQTPEKRLEWVA | TISSGGSYTYYPDSVKG-- | RFTISRDNAKNTLYLQMSSLRSEDTAMYYCAR- | RSYDGGGVWFAY------ | WGQGTLVTSL | SEQ ID NO. 82 |
| OD 149A | FRNFEVQLQESGTELVRPGASVKLSCKAL | GYTFTDYEMH-- | WVKQTPVHGLEWIG | AIHPGSGGTAYNQNFKG- | KATLTADKSSSTAYMELSSLTSEDSAVYYCTT- | YGNYFDY--------------- | WGQGTTLTVSL | SEQ ID NO. 84 |
| OD 218A | LPEFQVQLQESGGGLEQPGGSLKLSCAAS | GFDFSRYWMN-- | WVRQAPGKGLEWIG | EINPDSSTINYTPSLKD--- | KFIISRDNAKNTLYLQMSKVRSEDTALYYCAR- | PMGITKGFAY------------ | WGQGTLVTSLA | SEQ ID NO. 86 |
| OD 218B | LPEFQVQLQESGGGLEQPGGSLKLSCAAS | FGDFSRYWMN-- | WVRQAPGKGLEWIG | EINPDSSTINYTPSLKD--- | KRIISRDNAKNTLYLQMSKVRSEDTALYYCAR- | PMGITKGFAY------------ | WGQGTLVTSL | SEQ ID NO. 88 |
| OD 228 | FRKFEVQLQQSGAELVRPGASVKLSCKAS | GYTFTSYWMN-- | WVKQRPEQGLEWIG | RIDPYAGETQFNEKFKD-- | KAILTVDKSSSTAYMQLSSLTSEDSAVYYCAR- | PSLLRGAMDY----------- | WGQGTSVTVSS | SEQ ID NO. 90 |
| OD 238 | ----------VKLQESGPGILQPSQTLSLTCSFS | GFSLSTYDIGVG | WIRQPSGKGLEWLS | HIWWNDNKYYNTALKS-- | RLTISKDTSNNQVFLKIASVDTADTATYYCSR- | TGSYYYGTSSHYYVMDY | WGQGTSVTVSSA | SEQ ID NO. 92 |
| OD 243A | LSEFEVQLQESGGGLVQPGRPMKLSCVAS | GFTFSDYWMN-- | WVRQSPEKRLEWVA | QIRNKPFNYETYYSDSVKG | RFTISRDDSKSSVYLQMNNLRAEDMGIYYCTS- | IGYDGSFAY------------ | WGQGTLVTSAG | SEQ ID NO. 94 |
| OD 256 | FRKIEVQLQESGPELVKPGASVKMSCKAS | GYTFTSYVMH-- | WVKQKPGQGLEWIG | YINPYNDGTKYNEKFKG-- | KATLTSDKSSSTAYMELSSLTSEDSAVYYCAR- | GYGLGDY--------------- | WGQGTSVTVSS | SEQ ID NO. 96 |

[FIG. 11]
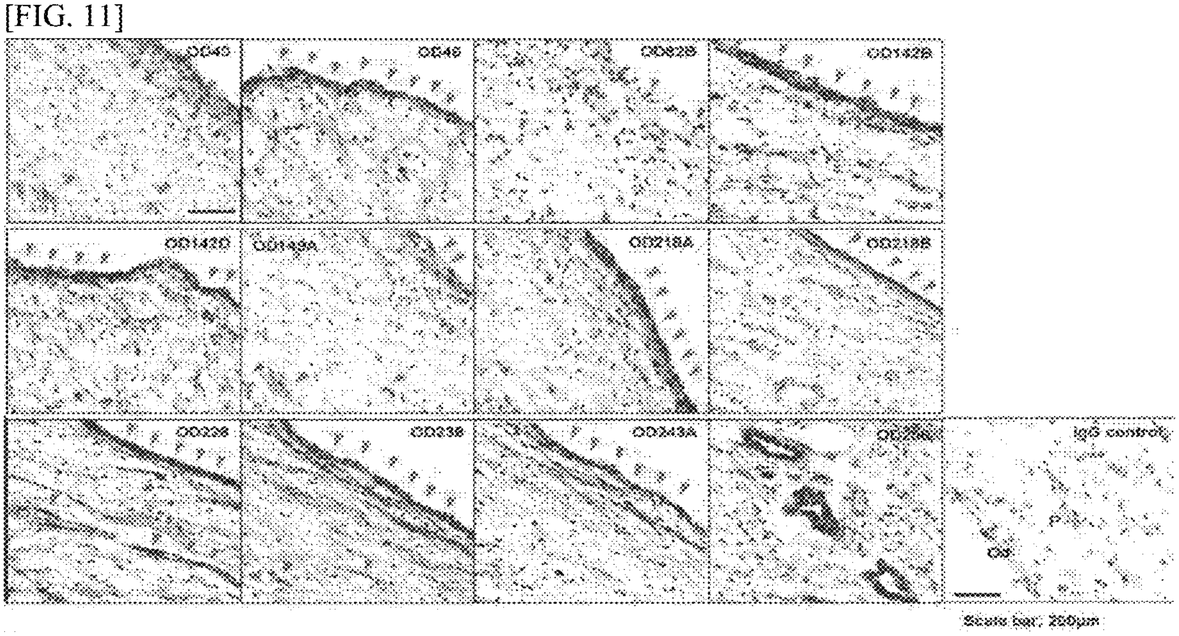

[FIG. 12]

a. IgM Light chain variable region

| | | ------CDR-L1------ | | ---CDR-L2--- | | ------CDR-L3------ | | |
|---|---|---|---|---|---|---|---|---|
| OD 7 | FRKLDIQLTQSPATLSVTPGDSVSLSC | RASQSISNNLH | WYQQFSHESPRLLIK | YASQSIS | GIPSRFSGSGSGTDFTLSINSVETEDFGMYFC | QQSNSWPLT | FGAGPS | SEQ ID NO. 211 |
| OD 111A | ----DIQLTQSPASLSASVGETVTITC | RASENIYSYLA | WYQQKQGKSPQLLVY | NAKTLAE | GVPSRFSGSGSFTQFSLKINSLQPEDFGSYYC | QHHYGTPLT | FGAGTKLELKRADAAPTVS | SEQ ID NO. 213 |
| OD 169B | -----MQLTQSPAIMSASPGEKVTMTC | SASSSVSYMH | WYQQKSGTSPKRWIY | DTSKLAS | GVPARFSGSGSGTSYSLTISSMEAEDAATYYC | QQWSSNPPT | FGSGQSE | SEQ ID NO. 215 |
| OD 184 | ----DIQLTQSPFSNPVTLGTSASISC | RSSMSLLESNGITYLY | WYLQKPGQSPQLLIY | QMSNLAS | GVPDRFSSSGSGTDFTLRISSRVEAEDVGVYYC | AWNLELPPT | FGGGTKLEIKRADAAPTVS | SEQ ID NO. 217 |
| OD 185 | -RKLDIQLTQSPSSLSVSAGEKVTMSC | KSSQSLLNSGNQKNYLA | WYQQKPGQPPKLLIY | GASTRES | GVPDRFTGSGSGTDFTLTISSVQAEDLAVYYC | QNDHSYPYT | FGGGPS | SEQ ID NO. 219 |
| OD 196 | CRKLDIQLTQSPKFMSTSVGDRVSVTC | KASQNVGTNVA | WYQQKPGQSPKALIY | SASYRYS | GVPDRFTGSGSGTDFTLTISNVQSEDLAEYFC | QQYNSYPYT | FGGGPS | SEQ ID NO. 221 |
| OD 210A | --KLDIVLTQSPASLAVSLGQRATISC | RASESVDNYGISFMN | WFQQKPGQPPKLLIY | AASNQGS | GVPARFSGSGSGTDFSLNINPMEEDDTAMYFC | QQSKEVPRT | FGGGTKNQSG | SEQ ID NO. 223 |
| OD 225 | --KLDIQLTQSPSSLSVSAGEKVTMSC | KSSQSLLNSGNQKNYLA | WYQQKPGQPPKLLIY | GASTRES | GVPDRFTGSGSGTDFTLTISSVQAEDLAVYYC | QNDHSYPFT | FGGQSE | SEQ ID NO. 225 |
| OD 234 | ----DIVLTQSPASLAVSLGQRATISY | RASKSVSTSGYSYMH | WNQQKPGQPPRLLTY | LVSNLES | GVPARFSGSGSGTDFTLNIHPVEEEDAATYYC | QHIRELTRAS | EGGPSWK | SEQ ID NO. 227 |
| OD 241 | ----DIQLTQSPASLSVATGEKVTIRC | ITSTDIDDDMN | WYQQKPGEPPKLLIS | EGNTLRP | GVPSRFSSSGYSTDFVFTIENTLSEDVADYYC | LQSDNMPFT | FGSGTKLEIPRADAAPTVS | SEQ ID NO. 229 |
| OD 244 | YRKLDIQLTQSPAIMSASPGEKVTISC | SASSSVSYMY | WYQQKPGSSPKPWIY | RTSNTLAS | GVPARFSGSGSGTSYSLTISSMEAEDAATYYC | QQYHSYPMYT | FGGGPS | SEQ ID NO. 231 |
| OD 270 | SPKLCIQLTQSPSSLSASLGGKVTITC | KASQDINKYIA | WYQHKPGKGPRLLIH | YTSTLQP | GIPSRFSGSGSGRDYSFSISNLEPEDIATYYC | LQYDNLWT | FGGGTKLNQAG | SEQ ID NO. 233 |
| OD 296 | -EKLDIQLTQSPSSLAVTAGEKVTMRC | KSSQSLLWSVNQKNYLS | WYQQKQGQPPKLLIY | GASIRES | WVPDRFTGSGSGTDFTLTISNVHAEDLAVYYC | QHNHGSFLPLT | FGAGPS | SEQ ID NO. 235 |
| OD 298 | YRKLDIQLTQSPAILSVSPGERVSFSC | RASQSIGTSIH | WYQQRTNGSPRLLIK | YASESIS | GIPSRFSGSGSTDFTLSINSVESEDIADYYC | QQSNSWPYT | FGGGPS | SEQ ID NO. 237 |
| OD 340 | RSEACIQLTQSPASLYASVGETVTITC | RASGNIHNYLA | WYQQKQGKSPQLLVY | NAKTLAD | GVPSRFSGSGSGTQYSLKINSLQPEDFGSYYC | QHFWSTPLY | FGAGPS | SEQ ID NO. 239 |

b. IgM Heavy chain variable region

| | | -------CDR-H1------- | | -----------CDR-H2----------- | | -----------CDR-H3----------- | | |
|---|---|---|---|---|---|---|---|---|
| OD 7 | FRKFEVQLQQSGAELVRPGASVKLSCKAS | GFSFTSYWMN | WVKQRPGQGLEWIG | MIHPSDSETRLNQKFKD | KATLTVDESSSTAYMQLSSPTSEDSAVYYCAR | FVVATGRYYSMDY | WGQGT | SEQ ID NO. 212 |
| OD 111A | LPEFQVQLQQSGAELMKPGASVKISCKAT | GYTFSSYWIE | WVKQRPGHGLEWIG | EILPGSGSTNYNEKFKG | KATFTADTSSNTAYMQLSSLTSEDSAVYYCAR | RKWGNYYNYYAMDY | WGQGTSVTVL | SEQ ID NO. 214 |
| OD 169B | LPEFEVQLEESGPGLVAPSQSLSITCTVS | FGSLTSYGVS | WVRQPPGKGLEWLG | VIWGDGSTNYHSALIS | RLSISKDNSKSQVFLKLNSLQTDDTATYYCAG | YRGY | WGQGTLVTTP | SEQ ID NO. 216 |
| OD 184 | LPEFQVQLQQSGSELRSPGSSVKLSCKDF | DSEVFPIAYMS | WVRQKPGHGFEWIG | DILPSIGRTIYGEKFED | KATLDADTVSNTAYLELNSLTSEDSAIYYCAR | EGSSGYGAWFAY | WGQGTLVTLC | SEQ ID NO. 218 |
| OD 185 | LPEFQVQLEQSGPGILQPSQTLSLTCSFS | GFSLSTSGMGVG | WIRQPSGKGLEWLA | HIWWDDDKRYNPALKS | RLTISKDTSSNQVFLKIADVDTADTATYYCAR | TEDSLLPLGFAY | WGQGTLVTTL | SEQ ID NO. 220 |
| OD 196 | LPEFEVQLQESGPELVKPGASVKISCKTS | GYTFTEYTMH | WVKQSHGKSLEWIG | GINPNNGGTSYNQKFKG | KATLTVDKSSSTAYMELRSLTSEDSAVYYCAT | GYAMDY | WGQGTSVTES | SEQ ID NO. 222 |
| OD 210A | FRKFQVQLQQSGGGLVQPGGSLKLSCAAS | GFDFSRYWMS | WVRQAPGKGLEWIG | EINPDSSTINYTPSLKD | KFIISRDNAKNTLYLQMSKVRSEDTALYYCAR | RGIYYGNYCDY | WGQGTTLTVPC | SEQ ID NO. 224 |
| OD 225 | LPEFQVQLQQSGAELVKPGTSVKMSCKAS | GYTFTSYWMH | WVKQRPGQGLEWIG | DIYPGSDSTNYNEKFKS | KATLTVDTSSSTAYMQLSSLTSEDSAVYYCAR | CDFYWYFDV | WGAGPRSPSL | SEQ ID NO. 226 |
| OD 234 | LSEFEVQLQQSGPELVKPGASMKISCKAS | GYSFTGYTMN | WVSHGKN---LEWIG | LINPYNGGTSYNQKFKG | KATLTVDKSSSTAYMELLSLTSEDSAVYYCAR | VRAYYGNYELFYWYFDV | WGAGPRSPSP | SEQ ID NO. 228 |
| OD 241 | FRKFQVQLQESGPGILQPSTQTLSLTCSFS | GFSLSTSGMSVG | WIRQPSGKGLEWLA | HIWWNDDNYYNPALKS | RLTISKDTSNNQVFLKIASVVTADTATYYCAR | IAREVRRYFDV | WGAGPRSPSL | SEQ ID NO. 230 |
| OD 244 | LPEIEVQLQQSGTVLARPGASVKMSCKAS | GYTFTSYWMH | WVKQRPGQGLEWIG | AOUGMSDTSUMQLPLGLA | KLTAVTSTSTAYMELSSLTNESDSAV---YYCTR | SOPPYWYFDV | WGAGPRSPPY | SEQ ID NO. 232 |
| OD 270 | FRKFEVQLQESGAELVRPGASVKLSCKAS | GYSFTSYWMN | WVKQRPGQGLEWIG | OJSDSETRMQLPLD | KATLTVDKSSSTAYMQLSSPTSEDSAVYYCVD | GYAMDY | WGQGTSVTVP | SEQ ID NO. 234 |
| OD 296 | FRKEEVQLQESGPELVKPGASVKMSCKAS | GYTFTSYVMH | WVKQKPGQGLEWIG | UOMUMDGTRUMELPLG | KATLTSDKSSSTAYMELSSLTSEDSAVYYCAR | REKYGNYVGAMDY | WGQGTSVTVL | SEQ ID NO. 236 |
| OD 298 | PRKIQVQLQESGPELVRPGVSVKISCKGS | GYTFTDYAMH | WVKQSHAKSLEWIG | VOSTUSGMTMUMQLPLG | KATMTVDKSSSTAYMELARLTSEDSAIYYCAR | EASGLCPFDY | WGQGTTLTVP | SEQ ID NO. 238 |
| OD 340 | LPEIEVQLQESGPELVKPGASVKISSCKAS | GYTFTDYNMH | WVKQSHGKSLEWIG | UOUUMGGTGUMQLPRS | KATLTVDNSSSTAYMELRSLTSEDSAVYYCAR | ADGNHPYYFDY | WGQGTTLTWS | SEQ ID NO. 240 |

SEQUENCE LISTING

```
<160> NUMBER OF SEQ ID NOS: 314

<210> SEQ ID NO 1
<211> LENGTH: 11
<212> TYPE: PRT
<213> ORGANISM: Artificial Sequence
<220> FEATURE:
<223> OTHER INFORMATION: OD40 Light chain CDR1

<400> SEQUENCE: 1

Arg Ala Ser Glu Asn Ile Tyr Ser His Leu Ala
1               5                   10


<210> SEQ ID NO 2
<211> LENGTH: 7
<212> TYPE: PRT
<213> ORGANISM: Artificial Sequence
<220> FEATURE:
<223> OTHER INFORMATION: OD40 Light chain CDR2

<400> SEQUENCE: 2

Ala Ala Thr Asn Leu Ala Asp
1               5


<210> SEQ ID NO 3
<211> LENGTH: 9
<212> TYPE: PRT
<213> ORGANISM: Artificial Sequence
<220> FEATURE:
<223> OTHER INFORMATION: OD40 Light chain CDR3

<400> SEQUENCE: 3

Gln His Phe Trp Gly Thr Leu Pro Thr
1               5


<210> SEQ ID NO 4
<211> LENGTH: 12
<212> TYPE: PRT
<213> ORGANISM: Artificial Sequence
<220> FEATURE:
<223> OTHER INFORMATION: OD40 heavy chain CDR1

<400> SEQUENCE: 4

Gly Phe Ser Leu Ser Thr Tyr Gly Ile Gly Val Gly
1               5                   10


<210> SEQ ID NO 5
<211> LENGTH: 16
<212> TYPE: PRT
<213> ORGANISM: Artificial Sequence
<220> FEATURE:
<223> OTHER INFORMATION: OD40 heavy chain CDR2
```

<400> SEQUENCE: 5

His Ile Trp Trp Asn Asp Asn Lys Tyr Tyr Asn Thr Ala Leu Lys Ser
1 5 10 15

<210> SEQ ID NO 6
<211> LENGTH: 10
<212> TYPE: PRT
<213> ORGANISM: Artificial Sequence
<220> FEATURE:
<223> OTHER INFORMATION: OD40 heavy chain CDR3

<400> SEQUENCE: 6

Ile Leu Trp Leu Arg Arg Pro Met Asp Tyr
1 5 10

<210> SEQ ID NO 7
<211> LENGTH: 17
<212> TYPE: PRT
<213> ORGANISM: Artificial Sequence
<220> FEATURE:
<223> OTHER INFORMATION: OD46 Light chain CDR1

<400> SEQUENCE: 7

Lys Ser Ser Gln Ser Leu Leu Asn Ser Ser Asn Gln Lys Asn Tyr Leu
1 5 10 15

Ala

<210> SEQ ID NO 8
<211> LENGTH: 7
<212> TYPE: PRT
<213> ORGANISM: Artificial Sequence
<220> FEATURE:
<223> OTHER INFORMATION: OD46 Light chain CDR2

<400> SEQUENCE: 8

Phe Ala Ser Ala Arg Lys Ser
1 5

<210> SEQ ID NO 9
<211> LENGTH: 9
<212> TYPE: PRT
<213> ORGANISM: Artificial Sequence
<220> FEATURE:
<223> OTHER INFORMATION: OD46 Light chain CDR3

<400> SEQUENCE: 9

Gln Gln His Tyr Thr Thr Pro Trp Thr
1 5

<210> SEQ ID NO 10
<211> LENGTH: 10
<212> TYPE: PRT
<213> ORGANISM: Artificial Sequence
<220> FEATURE:
<223> OTHER INFORMATION: OD46 heavy chain CDR1

<400> SEQUENCE: 10

Gly Tyr Ala Phe Ser Ser Tyr Trp Met Asn
1 5 10

<210> SEQ ID NO 11
<211> LENGTH: 17
<212> TYPE: PRT
<213> ORGANISM: Artificial Sequence
<220> FEATURE:

<223> OTHER INFORMATION: OD46 heavy chain CDR2

<400> SEQUENCE: 11

Gln Ile Tyr Pro Gly Asp Gly Asp Ser Asn Tyr Asn Gly Lys Phe Lys
1 5 10 15

Gly

<210> SEQ ID NO 12
<211> LENGTH: 8
<212> TYPE: PRT
<213> ORGANISM: Artificial Sequence
<220> FEATURE:
<223> OTHER INFORMATION: OD46 heavy chain CDR3

<400> SEQUENCE: 12

Gly Ser Thr Ala Thr Ala Asp Tyr
1 5

<210> SEQ ID NO 13
<211> LENGTH: 10
<212> TYPE: PRT
<213> ORGANISM: Artificial Sequence
<220> FEATURE:
<223> OTHER INFORMATION: OD82B Light chain CDR1

<400> SEQUENCE: 13

Ser Ala Ser Ser Ser Val Ser Tyr Met Asn
1 5 10

<210> SEQ ID NO 14
<211> LENGTH: 7
<212> TYPE: PRT
<213> ORGANISM: Artificial Sequence
<220> FEATURE:
<223> OTHER INFORMATION: OD82B Light chain CDR2

<400> SEQUENCE: 14

Leu Thr Ser Asn Leu Ala Ser
1 5

<210> SEQ ID NO 15
<211> LENGTH: 9
<212> TYPE: PRT
<213> ORGANISM: Artificial Sequence
<220> FEATURE:
<223> OTHER INFORMATION: OD82B Light chain CDR3

<400> SEQUENCE: 15

Gln Gln Trp Ser Ser Asn Pro Leu Thr
1 5

<210> SEQ ID NO 16
<211> LENGTH: 10
<212> TYPE: PRT
<213> ORGANISM: Artificial Sequence
<220> FEATURE:
<223> OTHER INFORMATION: OD82B Heavy chain CDR1

<400> SEQUENCE: 16

Gly Tyr Thr Phe Ala Ser Tyr Trp Met His
1 5 10

<210> SEQ ID NO 17
<211> LENGTH: 17
<212> TYPE: PRT
<213> ORGANISM: Artificial Sequence
<220> FEATURE:
<223> OTHER INFORMATION: OD82B Heavy chain CDR2

<400> SEQUENCE: 17

Tyr Ile Asn Pro Ser Thr Val Tyr Thr Glu Tyr Asn Gln Lys Phe Lys
1 5 10 15

Asp

<210> SEQ ID NO 18
<211> LENGTH: 8
<212> TYPE: PRT
<213> ORGANISM: Artificial Sequence
<220> FEATURE:
<223> OTHER INFORMATION: OD82B Heavy chain CDR3

<400> SEQUENCE: 18

Ser Arg Tyr Asp Gly Phe Ala Tyr
1 5

<210> SEQ ID NO 19
<211> LENGTH: 11
<212> TYPE: PRT
<213> ORGANISM: Artificial Sequence
<220> FEATURE:
<223> OTHER INFORMATION: OD142B Light chain CDR1

<400> SEQUENCE: 19

Lys Ala Ser Gln Ser Val Ser Asn Asp Val Ala
1 5 10

<210> SEQ ID NO 20
<211> LENGTH: 7
<212> TYPE: PRT
<213> ORGANISM: Artificial Sequence
<220> FEATURE:
<223> OTHER INFORMATION: OD142B Light chain CDR2

<400> SEQUENCE: 20

Tyr Ala Ser Asn Arg Tyr Thr
1 5

<210> SEQ ID NO 21
<211> LENGTH: 9
<212> TYPE: PRT
<213> ORGANISM: Artificial Sequence
<220> FEATURE:
<223> OTHER INFORMATION: OD142B Light chain CDR3

<400> SEQUENCE: 21

Gln Gln Asp Tyr Ser Ser Pro Tyr Thr
1 5

<210> SEQ ID NO 22
<211> LENGTH: 10
<212> TYPE: PRT
<213> ORGANISM: Artificial Sequence
<220> FEATURE:
<223> OTHER INFORMATION: OD142B Heavy chain CDR1

<400> SEQUENCE: 22

Gly Phe Thr Phe Ser Ser Tyr Ala Met Ser
1 5 10

<210> SEQ ID NO 23
<211> LENGTH: 17
<212> TYPE: PRT

-continued

<213> ORGANISM: Artificial Sequence
<220> FEATURE:
<223> OTHER INFORMATION: OD142B Heavy chain CDR2

<400> SEQUENCE: 23

Thr Ile Ser Ser Gly Gly Ser Tyr Thr Tyr Tyr Pro Asp Ser Val Lys
1 5 10 15

Gly

<210> SEQ ID NO 24
<211> LENGTH: 12
<212> TYPE: PRT
<213> ORGANISM: Artificial Sequence
<220> FEATURE:
<223> OTHER INFORMATION: OD142B Heavy chain CDR3

<400> SEQUENCE: 24

Arg Ser Tyr Asp Gly Gly Gly Val Trp Phe Ala Tyr
1 5 10

<210> SEQ ID NO 25
<211> LENGTH: 17
<212> TYPE: PRT
<213> ORGANISM: Artificial Sequence
<220> FEATURE:
<223> OTHER INFORMATION: OD142D Light chain CDR1

<400> SEQUENCE: 25

Lys Ser Ser Gln Ser Leu Leu Asn Ser Ser Asn Gln Lys Asn Tyr Leu
1 5 10 15

Ala

<210> SEQ ID NO 26
<211> LENGTH: 7
<212> TYPE: PRT
<213> ORGANISM: Artificial Sequence
<220> FEATURE:
<223> OTHER INFORMATION: OD142D Light chain CDR2

<400> SEQUENCE: 26

Phe Ala Ser Ala Arg Lys Ser
1 5

<210> SEQ ID NO 27
<211> LENGTH: 9
<212> TYPE: PRT
<213> ORGANISM: Artificial Sequence
<220> FEATURE:
<223> OTHER INFORMATION: OD142D Light chain CDR3

<400> SEQUENCE: 27

Gln Gln His Tyr Thr Thr Pro Trp Thr
1 5

<210> SEQ ID NO 28
<211> LENGTH: 10
<212> TYPE: PRT
<213> ORGANISM: Artificial Sequence
<220> FEATURE:
<223> OTHER INFORMATION: OD142D Heavy chain CDR1

<400> SEQUENCE: 28

Gly Phe Thr Phe Ser Ser Tyr Ala Met Ser
1 5 10

<210> SEQ ID NO 29
<211> LENGTH: 17
<212> TYPE: PRT
<213> ORGANISM: Artificial Sequence
<220> FEATURE:
<223> OTHER INFORMATION: OD142D Heavy chain CDR2

<400> SEQUENCE: 29

Thr Ile Ser Ser Gly Gly Ser Tyr Thr Tyr Tyr Pro Asp Ser Val Lys
1 5 10 15

Gly

<210> SEQ ID NO 30
<211> LENGTH: 12
<212> TYPE: PRT
<213> ORGANISM: Artificial Sequence
<220> FEATURE:
<223> OTHER INFORMATION: OD142D Heavy chain CDR3

<400> SEQUENCE: 30

Arg Ser Tyr Asp Gly Gly Gly Val Trp Phe Ala Tyr
1 5 10

<210> SEQ ID NO 31
<211> LENGTH: 11
<212> TYPE: PRT
<213> ORGANISM: Artificial Sequence
<220> FEATURE:
<223> OTHER INFORMATION: OD149A Light chain CDR1

<400> SEQUENCE: 31

Lys Ala Ser Gln Asn Val Gly Thr Asn Val Ala
1 5 10

<210> SEQ ID NO 32
<211> LENGTH: 7
<212> TYPE: PRT
<213> ORGANISM: Artificial Sequence
<220> FEATURE:
<223> OTHER INFORMATION: OD149A Light chain CDR2

<400> SEQUENCE: 32

Ser Ala Ser Tyr Arg Tyr Ser
1 5

<210> SEQ ID NO 33
<211> LENGTH: 9
<212> TYPE: PRT
<213> ORGANISM: Artificial Sequence
<220> FEATURE:
<223> OTHER INFORMATION: OD149A Light chain CDR3

<400> SEQUENCE: 33

Gln Gln Tyr Asn Ser Tyr Pro Leu Thr
1 5

<210> SEQ ID NO 34
<211> LENGTH: 10
<212> TYPE: PRT
<213> ORGANISM: Artificial Sequence
<220> FEATURE:
<223> OTHER INFORMATION: OD149A Heavy chain CDR1

<400> SEQUENCE: 34

Gly Tyr Thr Phe Ile Asp Tyr Glu Met His
1 5 10

<210> SEQ ID NO 35
<211> LENGTH: 17
<212> TYPE: PRT
<213> ORGANISM: Artificial Sequence
<220> FEATURE:
<223> OTHER INFORMATION: OD149A Heavy chain CDR2

<400> SEQUENCE: 35

Ala Ile His Pro Gly Ser Gly Gly Thr Ala Tyr Asn Gln Asn Phe Lys
1 5 10 15

Gly

<210> SEQ ID NO 36
<211> LENGTH: 7
<212> TYPE: PRT
<213> ORGANISM: Artificial Sequence
<220> FEATURE:
<223> OTHER INFORMATION: OD149A Heavy chain CDR3

<400> SEQUENCE: 36

Tyr Gly Asn Tyr Phe Asp Tyr
1 5

<210> SEQ ID NO 37
<211> LENGTH: 10
<212> TYPE: PRT
<213> ORGANISM: Artificial Sequence
<220> FEATURE:
<223> OTHER INFORMATION: OD218A  Light chain CDR1

<400> SEQUENCE: 37

Arg Ala Ser Ser Ser Val Ser Tyr Met Asn
1 5 10

<210> SEQ ID NO 38
<211> LENGTH: 7
<212> TYPE: PRT
<213> ORGANISM: Artificial Sequence
<220> FEATURE:
<223> OTHER INFORMATION: OD218A  Light chain CDR2

<400> SEQUENCE: 38

Ala Thr Ser Asn Leu Ala Ser
1 5

<210> SEQ ID NO 39
<211> LENGTH: 10
<212> TYPE: PRT
<213> ORGANISM: Artificial Sequence
<220> FEATURE:
<223> OTHER INFORMATION: OD218A  Light chain CDR3

<400> SEQUENCE: 39

Gln Gln Trp Ser Ser Asn Pro Pro Tyr Thr
1 5 10

<210> SEQ ID NO 40
<211> LENGTH: 10
<212> TYPE: PRT
<213> ORGANISM: Artificial Sequence
<220> FEATURE:
<223> OTHER INFORMATION: OD218A  Heavy chain CDR1

<400> SEQUENCE: 40

Gly Phe Asp Phe Ser Arg Tyr Trp Met Asn
1 5 10

<210> SEQ ID NO 41
<211> LENGTH: 17
<212> TYPE: PRT
<213> ORGANISM: Artificial Sequence
<220> FEATURE:
<223> OTHER INFORMATION: OD218A Heavy chain CDR2

<400> SEQUENCE: 41

Glu Ile Asn Pro Asp Ser Ser Thr Ile Asn Tyr Thr Pro Ser Leu Lys
1 5 10 15

Asp

<210> SEQ ID NO 42
<211> LENGTH: 10
<212> TYPE: PRT
<213> ORGANISM: Artificial Sequence
<220> FEATURE:
<223> OTHER INFORMATION: OD218A Heavy chain CDR3

<400> SEQUENCE: 42

Pro Met Gly Ile Thr Lys Gly Phe Ala Tyr
1 5 10

<210> SEQ ID NO 43
<211> LENGTH: 11
<212> TYPE: PRT
<213> ORGANISM: Artificial Sequence
<220> FEATURE:
<223> OTHER INFORMATION: OD218B Light chain CDR1

<400> SEQUENCE: 43

Lys Ala Ser Gln Asp Val Ser Thr Thr Val Ala
1 5 10

<210> SEQ ID NO 44
<211> LENGTH: 7
<212> TYPE: PRT
<213> ORGANISM: Artificial Sequence
<220> FEATURE:
<223> OTHER INFORMATION: OD218B Light chain CDR2

<400> SEQUENCE: 44

Trp Ala Ser Thr Arg His Thr
1 5

<210> SEQ ID NO 45
<211> LENGTH: 9
<212> TYPE: PRT
<213> ORGANISM: Artificial Sequence
<220> FEATURE:
<223> OTHER INFORMATION: OD218B Light chain CDR3

<400> SEQUENCE: 45

Gln Gln His Tyr Ser Thr Pro Tyr Thr
1 5

<210> SEQ ID NO 46
<211> LENGTH: 10
<212> TYPE: PRT
<213> ORGANISM: Artificial Sequence
<220> FEATURE:
<223> OTHER INFORMATION: OD218B Heavy chain CDR1

<400> SEQUENCE: 46

Gly Phe Asp Phe Ser Arg Tyr Trp Met Asn 1 5 10

<210> SEQ ID NO 47
<211> LENGTH: 17
<212> TYPE: PRT
<213> ORGANISM: Artificial Sequence
<220> FEATURE:
<223> OTHER INFORMATION: OD218B Heavy chain CDR2

<400> SEQUENCE: 47

Glu Ile Asn Pro Asp Ser Ser Thr Ile Asn Tyr Thr Pro Ser Leu Lys
1 5 10 15

Asp

<210> SEQ ID NO 48
<211> LENGTH: 10
<212> TYPE: PRT
<213> ORGANISM: Artificial Sequence
<220> FEATURE:
<223> OTHER INFORMATION: OD218B Heavy chain CDR3

<400> SEQUENCE: 48

Pro Met Gly Ile Thr Lys Gly Phe Ala Tyr
1 5 10

<210> SEQ ID NO 49
<211> LENGTH: 17
<212> TYPE: PRT
<213> ORGANISM: Artificial Sequence
<220> FEATURE:
<223> OTHER INFORMATION: OD228 Light chain CDR1

<400> SEQUENCE: 49

Lys Ser Ser Gln Ser Val Leu Tyr Ser Ser Asn Gln Lys Asn Tyr Leu
1 5 10 15

Ala

<210> SEQ ID NO 50
<211> LENGTH: 7
<212> TYPE: PRT
<213> ORGANISM: Artificial Sequence
<220> FEATURE:
<223> OTHER INFORMATION: OD228 Light chain CDR2

<400> SEQUENCE: 50

Trp Ala Ser Thr Arg Glu Ser
1 5

<210> SEQ ID NO 51
<211> LENGTH: 7
<212> TYPE: PRT
<213> ORGANISM: Artificial Sequence
<220> FEATURE:
<223> OTHER INFORMATION: OD228 Light chain CDR3

<400> SEQUENCE: 51

His Gln Tyr Leu Ser Trp Thr
1 5

<210> SEQ ID NO 52
<211> LENGTH: 10
<212> TYPE: PRT
<213> ORGANISM: Artificial Sequence
<220> FEATURE:
<223> OTHER INFORMATION: OD228 Heavy chain CDR1

<400> SEQUENCE: 52

Gly Tyr Thr Phe Thr Ser Tyr Trp Met Asn
1               5                   10

<210> SEQ ID NO 53
<211> LENGTH: 17
<212> TYPE: PRT
<213> ORGANISM: Artificial Sequence
<220> FEATURE:
<223> OTHER INFORMATION: OD228 Heavy chain CDR2

<400> SEQUENCE: 53

Arg Ile Asp Pro Tyr Ala Gly Glu Thr Gln Phe Asn Glu Lys Phe Lys
1               5                   10                  15

Asp

<210> SEQ ID NO 54
<211> LENGTH: 10
<212> TYPE: PRT
<213> ORGANISM: Artificial Sequence
<220> FEATURE:
<223> OTHER INFORMATION: OD228 Heavy chain CDR3

<400> SEQUENCE: 54

Pro Ser Leu Leu Arg Gly Ala Met Asp Tyr
1               5                   10

<210> SEQ ID NO 55
<211> LENGTH: 17
<212> TYPE: PRT
<213> ORGANISM: Artificial Sequence
<220> FEATURE:
<223> OTHER INFORMATION: OD238  Light chain CDR1

<400> SEQUENCE: 55

Lys Ser Ser Gln Ser Leu Leu Asn Ser Ser Asn Gln Lys Asn Tyr Leu
1               5                   10                  15

Ala

<210> SEQ ID NO 56
<211> LENGTH: 7
<212> TYPE: PRT
<213> ORGANISM: Artificial Sequence
<220> FEATURE:
<223> OTHER INFORMATION: OD238  Light chain CDR2
<220> FEATURE:
<221> NAME/KEY: MISC_FEATURE
<222> LOCATION: (4)..(4)
<223> OTHER INFORMATION: unknown or other

<400> SEQUENCE: 56

Phe Ala Ser Xaa Arg Lys Ser
1               5

<210> SEQ ID NO 57
<211> LENGTH: 9
<212> TYPE: PRT
<213> ORGANISM: Artificial Sequence
<220> FEATURE:
<223> OTHER INFORMATION: OD238  Light chain CDR3

<400> SEQUENCE: 57

Gln Gln His Tyr Thr Thr Pro Trp Thr
1               5

-continued

<210> SEQ ID NO 58
<211> LENGTH: 12
<212> TYPE: PRT
<213> ORGANISM: Artificial Sequence
<220> FEATURE:
<223> OTHER INFORMATION: OD238 Heavy chain CDR1

<400> SEQUENCE: 58

Gly Phe Ser Leu Ser Thr Tyr Asp Ile Gly Val Gly
1 5 10

<210> SEQ ID NO 59
<211> LENGTH: 16
<212> TYPE: PRT
<213> ORGANISM: Artificial Sequence
<220> FEATURE:
<223> OTHER INFORMATION: OD238 Heavy chain CDR2

<400> SEQUENCE: 59

His Ile Trp Trp Asn Asp Asn Lys Tyr Tyr Asn Thr Ala Leu Lys Ser
1 5 10 15

<210> SEQ ID NO 60
<211> LENGTH: 17
<212> TYPE: PRT
<213> ORGANISM: Artificial Sequence
<220> FEATURE:
<223> OTHER INFORMATION: OD238 Heavy chain CDR3

<400> SEQUENCE: 60

Ile Gly Ser Tyr Tyr Tyr Gly Thr Ser Ser His Tyr Tyr Val Met Asp
1 5 10 15

Tyr

<210> SEQ ID NO 61
<211> LENGTH: 11
<212> TYPE: PRT
<213> ORGANISM: Artificial Sequence
<220> FEATURE:
<223> OTHER INFORMATION: OD243A Light chain CDR1

<400> SEQUENCE: 61

Arg Ala Ser Leu Asp Ile Ser Asn Tyr Leu Asn
1 5 10

<210> SEQ ID NO 62
<211> LENGTH: 7
<212> TYPE: PRT
<213> ORGANISM: Artificial Sequence
<220> FEATURE:
<223> OTHER INFORMATION: OD243A Light chain CDR2

<400> SEQUENCE: 62

Tyr Thr Ser Arg Leu His Ser
1 5

<210> SEQ ID NO 63
<211> LENGTH: 9
<212> TYPE: PRT
<213> ORGANISM: Artificial Sequence
<220> FEATURE:
<223> OTHER INFORMATION: OD243A Light chain CDR3

<400> SEQUENCE: 63

Gln Gln Gly Asn Thr Leu Pro Trp Thr
1 5

<210> SEQ ID NO 64
<211> LENGTH: 10
<212> TYPE: PRT
<213> ORGANISM: Artificial Sequence
<220> FEATURE:
<223> OTHER INFORMATION: OD243A Heavy chain CDR1

<400> SEQUENCE: 64

Gly Phe Thr Phe Ser Asp Tyr Trp Met Asn
1 5 10

<210> SEQ ID NO 65
<211> LENGTH: 19
<212> TYPE: PRT
<213> ORGANISM: Artificial Sequence
<220> FEATURE:
<223> OTHER INFORMATION: OD243A Heavy chain CDR2

<400> SEQUENCE: 65

Gln Ile Arg Asn Lys Pro Phe Asn Tyr Glu Thr Tyr Tyr Ser Asp Ser
1 5 10 15

Val Lys Gly

<210> SEQ ID NO 66
<211> LENGTH: 9
<212> TYPE: PRT
<213> ORGANISM: Artificial Sequence
<220> FEATURE:
<223> OTHER INFORMATION: OD243A Heavy chain CDR3

<400> SEQUENCE: 66

Ile Gly Tyr Asp Gly Ser Phe Ala Tyr
1 5

<210> SEQ ID NO 67
<211> LENGTH: 16
<212> TYPE: PRT
<213> ORGANISM: Artificial Sequence
<220> FEATURE:
<223> OTHER INFORMATION: OD256 Light chain CDR1

<400> SEQUENCE: 67

Arg Ser Ser Gln Ser Leu Val His Ser Asn Gly Asn Thr Tyr Leu His
1 5 10 15

<210> SEQ ID NO 68
<211> LENGTH: 7
<212> TYPE: PRT
<213> ORGANISM: Artificial Sequence
<220> FEATURE:
<223> OTHER INFORMATION: OD256 Light chain CDR2

<400> SEQUENCE: 68

Lys Val Ser Asn Arg Phe Ser
1 5

<210> SEQ ID NO 69
<211> LENGTH: 9
<212> TYPE: PRT
<213> ORGANISM: Artificial Sequence
<220> FEATURE:
<223> OTHER INFORMATION: OD256 Light chain CDR3

<400> SEQUENCE: 69

Ser Gln Ser Thr His Val Pro Phe Thr
1 5

<210> SEQ ID NO 70
<211> LENGTH: 10
<212> TYPE: PRT
<213> ORGANISM: Artificial Sequence
<220> FEATURE:
<223> OTHER INFORMATION: OD256 Heavy chain CDR1

<400> SEQUENCE: 70

Gly Tyr Thr Phe Thr Ser Tyr Val Met His
1 5 10

<210> SEQ ID NO 71
<211> LENGTH: 17
<212> TYPE: PRT
<213> ORGANISM: Artificial Sequence
<220> FEATURE:
<223> OTHER INFORMATION: OD256 Heavy chain CDR2

<400> SEQUENCE: 71

Tyr Ile Asn Pro Tyr Asn Asp Gly Thr Lys Tyr Asn Glu Lys Phe Lys
1 5 10 15

Gly

<210> SEQ ID NO 72
<211> LENGTH: 7
<212> TYPE: PRT
<213> ORGANISM: Artificial Sequence
<220> FEATURE:
<223> OTHER INFORMATION: OD256 Heavy chain CDR3

<400> SEQUENCE: 72

Gly Tyr Gly Leu Gly Asp Tyr
1 5

<210> SEQ ID NO 73
<211> LENGTH: 111
<212> TYPE: PRT
<213> ORGANISM: Artificial Sequence
<220> FEATURE:
<223> OTHER INFORMATION: OD40 Light chain

<400> SEQUENCE: 73

Phe Arg Lys Leu Asp Ile Gln Leu Thr Gln Ser Pro Ala Ser Leu Ser
1 5 10 15

Val Ser Val Gly Glu Thr Val Thr Ile Thr Cys Arg Ala Ser Glu Asn
20 25 30

Ile Tyr Ser His Leu Ala Trp Tyr Gln Glu Lys Gln Gly Lys Ser Pro
35 40 45

Gln Leu Leu Val Tyr Ala Ala Thr Asn Leu Ala Asp Gly Val Pro Ser
50 55 60

Arg Phe Ser Gly Ser Gly Ser Gly Thr Gln Tyr Ser Leu Lys Ile Asn
65 70 75 80

Arg Leu Gln Ser Glu Asp Phe Gly Ser Tyr Tyr Cys Gln His Phe Trp
85 90 95

Gly Thr Leu Pro Thr Phe Gly Gly Gly Pro Ser Glu Lys Ser Gly
100 105 110

<210> SEQ ID NO 74
<211> LENGTH: 124
<212> TYPE: PRT
<213> ORGANISM: Artificial Sequence
<220> FEATURE:

-continued

<223> OTHER INFORMATION: OD40 Heavy chain

<400> SEQUENCE: 74

```
Phe Arg Lys Phe Glu Val Gln Leu Gln Glu Ser Gly Pro Gly Ile Leu
1               5                   10                  15

Gln Pro Ser Gln Thr Leu Ser Leu Thr Cys Ser Phe Ser Gly Phe Ser
            20                  25                  30

Leu Ser Thr Tyr Gly Ile Gly Val Gly Trp Ile Arg Gln Pro Ser Gly
        35                  40                  45

Lys Gly Leu Glu Trp Leu Ala His Ile Trp Trp Asn Asp Asn Lys Tyr
    50                  55                  60

Tyr Asn Thr Ala Leu Lys Ser Arg Leu Thr Ile Ser Lys Asp Ile Ser
65                  70                  75                  80

Asn Asn Gln Val Phe Leu Lys Ile Val Ser Val Asp Thr Ala Asp Thr
                85                  90                  95

Ala Thr Tyr Tyr Cys Ala Arg Ile Leu Trp Leu Arg Arg Pro Met Asp
            100                 105                 110

Tyr Trp Gly Gln Gly Thr Ser Val Ile Val Ser Ser
        115                 120
```

<210> SEQ ID NO 75
<211> LENGTH: 117
<212> TYPE: PRT
<213> ORGANISM: Artificial Sequence
<220> FEATURE:
<223> OTHER INFORMATION: OD46 Light chain

<400> SEQUENCE: 75

```
Arg Lys Leu Asp Ile Gln Leu Thr Gln Ser Pro Ser Ser Leu Ala Met
1               5                   10                  15

Ser Val Gly Gln Lys Val Thr Met Ser Cys Lys Ser Ser Gln Ser Leu
            20                  25                  30

Leu Asn Ser Ser Asn Gln Lys Asn Tyr Leu Ala Trp Tyr Gln Gln Lys
        35                  40                  45

Pro Gly Gln Ser Pro Lys Leu Leu Val Tyr Phe Ala Ser Ala Arg Lys
    50                  55                  60

Ser Gly Val Pro Asp Arg Phe Ile Gly Ser Gly Ser Gly Thr Asp Phe
65                  70                  75                  80

Thr Leu Thr Ile Ser Ser Val Gln Ala Glu Asp Leu Ala Asp Tyr Phe
                85                  90                  95

Cys Gln Gln His Tyr Thr Thr Pro Trp Thr Phe Gly Gly Gly Thr Lys
            100                 105                 110

Leu Asn Gln Thr Gly
        115
```

<210> SEQ ID NO 76
<211> LENGTH: 123
<212> TYPE: PRT
<213> ORGANISM: Artificial Sequence
<220> FEATURE:
<223> OTHER INFORMATION: OD46 Heavy chain

<400> SEQUENCE: 76

```
Phe Arg Lys Ile Glu Val Gln Leu Gln Gln Ser Gly Ala Glu Leu Val
1               5                   10                  15

Arg Pro Gly Ser Ser Val Lys Ile Ser Cys Lys Ala Ser Gly Tyr Ala
            20                  25                  30

Phe Ser Ser Tyr Trp Met Asn Trp Val Lys Gln Arg Pro Gly Gln Gly
```

-continued

```
        35                  40                  45

Leu Glu Trp Ile Gly Gln Ile Tyr Pro Gly Asp Gly Asp Ser Asn Tyr
    50                  55                  60

Asn Gly Lys Phe Lys Gly Lys Ala Thr Leu Thr Ala Asp Lys Ser Ser
65                  70                  75                  80

Ser Ile Ala Tyr Met Gln Leu Ser Ser Leu Thr Ser Glu Asp Ser Ala
                85                  90                  95

Val Tyr Phe Cys Ala Arg Phe Gly Ser Thr Ala Thr Ala Asp Tyr Trp
            100                 105                 110

Gly Gln Gly Thr Thr Leu Thr Val Ser Ser Ala
        115                 120
```

<210> SEQ ID NO 77
<211> LENGTH: 106
<212> TYPE: PRT
<213> ORGANISM: Artificial Sequence
<220> FEATURE:
<223> OTHER INFORMATION: OD82B Light chain

<400> SEQUENCE: 77

```
Phe Arg Lys Leu Asp Ile Gln Leu Thr Gln Ser Pro Ala Leu Met Ser
1               5                   10                  15

Ala Ser Pro Gly Glu Lys Val Thr Met Thr Cys Ser Ala Ser Ser Ser
            20                  25                  30

Val Ser Tyr Met Asn Trp Tyr Gln Gln Lys Pro Arg Ser Ser Pro Lys
        35                  40                  45

Pro Trp Ile Tyr Leu Thr Ser Asn Leu Ala Ser Gly Val Pro Ala Arg
    50                  55                  60

Phe Ser Gly Ser Gly Ser Gly Thr Ser Tyr Ser Leu Thr Ile Ser Asn
65                  70                  75                  80

Met Glu Ala Glu Asp Ala Ala Thr Tyr Tyr Cys Gln Gln Trp Ser Ser
                85                  90                  95

Asn Pro Leu Thr Phe Gly Ala Gly Pro Ser
            100                 105
```

<210> SEQ ID NO 78
<211> LENGTH: 121
<212> TYPE: PRT
<213> ORGANISM: Artificial Sequence
<220> FEATURE:
<223> OTHER INFORMATION: OD82B Heavy chain

<400> SEQUENCE: 78

```
Leu Pro Glu Phe Gln Val Gln Leu Glu Gln Ser Gly Ala Glu Leu Ala
1               5                   10                  15

Lys Pro Gly Ala Ser Val Lys Met Ser Cys Lys Ala Ser Gly Tyr Thr
            20                  25                  30

Phe Ala Ser Tyr Trp Met His Trp Met Lys Gln Arg Pro Gly Gln Gly
        35                  40                  45

Leu Glu Trp Ile Gly Tyr Ile Asn Pro Ser Thr Val Tyr Thr Glu Tyr
    50                  55                  60

Asn Gln Lys Phe Lys Asp Lys Ala Ser Leu Thr Ala Asp Thr Ser Ser
65                  70                  75                  80

Ser Thr Ala Tyr Met Gln Leu Ser Ser Leu Thr Ser Glu Asp Ser Ala
                85                  90                  95

Val Tyr Tyr Cys Ala Arg Ser Arg Tyr Asp Gly Phe Ala Tyr Trp Gly
            100                 105                 110
```

```
Gln Gly Thr Leu Val Thr Ser Pro Ala
        115                 120


<210> SEQ ID NO 79
<211> LENGTH: 116
<212> TYPE: PRT
<213> ORGANISM: Artificial Sequence
<220> FEATURE:
<223> OTHER INFORMATION: OD142B Light chain

<400> SEQUENCE: 79

Asp Ile Gln Leu Thr Gln Ser Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Asn Thr Met Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg Ala Asp Ala Ala
            100                 105                 110

Pro Thr Val Ser
        115


<210> SEQ ID NO 80
<211> LENGTH: 124
<212> TYPE: PRT
<213> ORGANISM: Artificial Sequence
<220> FEATURE:
<223> OTHER INFORMATION: OD142B Heavy chain

<400> SEQUENCE: 80

Phe Arg Asn Phe Glu Val Gln Leu Gln Gln Ser Gly Gly Gly Leu Val
1               5                   10                  15

Lys Pro Gly Gly Ser Leu Lys Leu Ser Cys Ala Ala Ser Gly Phe Thr
            20                  25                  30

Phe Ser Ser Tyr Ala Met Ser Trp Val Arg Gln Thr Pro Glu Lys Arg
        35                  40                  45

Leu Glu Trp Val Ala Thr Ile Ser Ser Gly Gly Ser Tyr Thr Tyr Tyr
    50                  55                  60

Pro Asp Ser Val Lys Gly Arg Phe Thr Ile Ser Arg Asp Asn Ala Lys
65                  70                  75                  80

Asn Thr Leu Tyr Leu Gln Met Ser Ser Leu Arg Ser Glu Asp Thr Ala
                85                  90                  95

Met Tyr Tyr Cys Ala Arg Arg Ser Tyr Asp Gly Gly Gly Val Trp Phe
            100                 105                 110

Ala Tyr Trp Gly Gln Gly Thr Leu Val Thr Ser Leu
        115                 120


<210> SEQ ID NO 81
<211> LENGTH: 118
<212> TYPE: PRT
<213> ORGANISM: Artificial Sequence
<220> FEATURE:
<223> OTHER INFORMATION: OD142D light chain
```

<400> SEQUENCE: 81

Phe Arg Lys Leu Asp Ile Gln Leu Thr Gln Ser Pro Ser Ser Leu Ala
1 5 10 15

Met Ser Val Gly Gln Lys Val Thr Met Ser Cys Lys Ser Ser Gln Ser
20 25 30

Leu Leu Asn Ser Ser Asn Gln Lys Asn Tyr Leu Ala Trp Tyr Gln Gln
35 40 45

Lys Pro Gly Gln Ser Pro Lys Leu Leu Val Tyr Phe Ala Ser Ala Arg
50 55 60

Lys Ser Gly Val Pro Asp Arg Phe Ile Gly Ser Gly Ser Gly Thr Asp
65 70 75 80

Phe Thr Leu Thr Ile Ser Ser Val Gln Ala Glu Asp Leu Ala Asp Tyr
85 90 95

Phe Cys Gln Gln His Tyr Thr Thr Pro Trp Thr Phe Gly Gly Gly Thr
100 105 110

Lys Leu Asn Gln Ala Gly
115

<210> SEQ ID NO 82
<211> LENGTH: 124
<212> TYPE: PRT
<213> ORGANISM: Artificial Sequence
<220> FEATURE:
<223> OTHER INFORMATION: OD142D Heavy chain

<400> SEQUENCE: 82

Phe Arg Lys Phe Glu Val Gln Leu Gln Gln Ser Gly Gly Gly Leu Val
1 5 10 15

Lys Pro Gly Gly Ser Leu Lys Leu Ser Cys Ala Ala Ser Gly Phe Thr
20 25 30

Phe Ser Ser Tyr Ala Met Ser Trp Val Arg Gln Thr Pro Glu Lys Arg
35 40 45

Leu Glu Trp Val Ala Thr Ile Ser Ser Gly Gly Ser Tyr Thr Tyr Tyr
50 55 60

Pro Asp Ser Val Lys Gly Arg Phe Thr Ile Ser Arg Asp Asn Ala Lys
65 70 75 80

Asn Thr Leu Tyr Leu Gln Met Ser Ser Leu Arg Ser Glu Asp Thr Ala
85 90 95

Met Tyr Tyr Cys Ala Arg Arg Ser Tyr Asp Gly Gly Gly Val Trp Phe
100 105 110

Ala Tyr Trp Gly Gln Gly Thr Leu Val Thr Ser Leu
115 120

<210> SEQ ID NO 83
<211> LENGTH: 106
<212> TYPE: PRT
<213> ORGANISM: Artificial Sequence
<220> FEATURE:
<223> OTHER INFORMATION: OD149A Light chain

<400> SEQUENCE: 83

Arg Lys Leu Asp Ile Gln Leu Thr Gln Ser Pro Lys Phe Met Ser Thr
1 5 10 15

Ser Val Gly Asp Arg Val Ser Val Thr Cys Lys Ala Ser Gln Asn Val
20 25 30

Gly Thr Asn Val Ala Trp Tyr Gln Gln Lys Pro Gly Gln Ser Pro Lys
35 40 45

Ala Leu Ile Tyr Ser Ala Ser Tyr Arg Tyr Ser Gly Val Pro Asp Arg
    50                  55                  60

Phe Thr Gly Ser Gly Ser Gly Thr Asp Phe Thr Leu Thr Ile Ser Asn
65                  70                  75                  80

Val Gln Ser Glu Asp Leu Ala Glu Tyr Phe Cys Gln Gln Tyr Asn Ser
                85                  90                  95

Tyr Pro Leu Thr Phe Gly Ala Gly Pro Ser
            100                 105

<210> SEQ ID NO 84
<211> LENGTH: 120
<212> TYPE: PRT
<213> ORGANISM: Artificial Sequence
<220> FEATURE:
<223> OTHER INFORMATION: OD149A heavy chain

<400> SEQUENCE: 84

Phe Arg Asn Phe Glu Val Gln Leu Gln Glu Ser Gly Thr Glu Leu Val
1               5                   10                  15

Arg Pro Gly Ala Ser Val Lys Leu Ser Cys Lys Ala Leu Gly Tyr Thr
            20                  25                  30

Phe Ile Asp Tyr Glu Met His Trp Val Lys Gln Thr Pro Val His Gly
        35                  40                  45

Leu Glu Trp Ile Gly Ala Ile His Pro Gly Ser Gly Gly Thr Ala Tyr
    50                  55                  60

Asn Gln Asn Phe Lys Gly Lys Ala Thr Leu Thr Ala Asp Lys Ser Ser
65                  70                  75                  80

Ser Thr Ala Tyr Met Glu Leu Ser Ser Leu Thr Ser Glu Asp Ser Ala
                85                  90                  95

Val Tyr Tyr Cys Thr Thr Tyr Gly Asn Tyr Phe Asp Tyr Trp Gly Gln
            100                 105                 110

Gly Thr Thr Leu Thr Val Ser Leu
        115                 120

<210> SEQ ID NO 85
<211> LENGTH: 107
<212> TYPE: PRT
<213> ORGANISM: Artificial Sequence
<220> FEATURE:
<223> OTHER INFORMATION: OD218A Light chain

<400> SEQUENCE: 85

Tyr Arg Lys Leu Asp Ile Gln Leu Thr Gln Ser Pro Ala Ile Leu Ser
1               5                   10                  15

Ala Phe Pro Gly Glu Lys Val Thr Met Thr Cys Arg Ala Ser Ser Ser
            20                  25                  30

Val Ser Tyr Met Asn Trp Tyr Gln Gln Lys Pro Gly Ser Ser Pro Lys
        35                  40                  45

Pro Trp Ile Tyr Ala Thr Ser Asn Leu Ala Ser Gly Val Pro Ala Arg
    50                  55                  60

Phe Ser Gly Ser Gly Ser Gly Ala Ser Tyr Ser Leu Thr Ile Ser Arg
65                  70                  75                  80

Val Glu Ala Glu Asp Ala Ala Thr Tyr Tyr Cys Gln Gln Trp Ser Ser
                85                  90                  95

Asn Pro Pro Tyr Thr Phe Gly Gly Gly Pro Ser
            100                 105

<210> SEQ ID NO 86

<211> LENGTH: 123
<212> TYPE: PRT
<213> ORGANISM: Artificial Sequence
<220> FEATURE:
<223> OTHER INFORMATION: OD218A heavy chain

<400> SEQUENCE: 86

```
Leu Pro Glu Phe Gln Val Gln Leu Gln Glu Ser Gly Gly Gly Leu Glu
1               5                   10                  15

Gln Pro Gly Gly Ser Leu Lys Leu Ser Cys Ala Ala Ser Gly Phe Asp
            20                  25                  30

Phe Ser Arg Tyr Trp Met Asn Trp Val Arg Gln Ala Pro Gly Lys Gly
        35                  40                  45

Leu Glu Trp Ile Gly Glu Ile Asn Pro Asp Ser Ser Thr Ile Asn Tyr
    50                  55                  60

Thr Pro Ser Leu Lys Asp Lys Phe Ile Ile Ser Arg Asp Asn Ala Lys
65                  70                  75                  80

Asn Thr Leu Tyr Leu Gln Met Ser Lys Val Arg Ser Glu Asp Thr Ala
                85                  90                  95

Leu Tyr Tyr Cys Ala Arg Pro Met Gly Ile Thr Lys Gly Phe Ala Tyr
            100                 105                 110

Trp Gly Gln Gly Thr Leu Val Thr Ser Leu Ala
        115                 120
```

<210> SEQ ID NO 87
<211> LENGTH: 115
<212> TYPE: PRT
<213> ORGANISM: Artificial Sequence
<220> FEATURE:
<223> OTHER INFORMATION: OD218B Light chain

<400> SEQUENCE: 87

```
His Ser Ala Asp Pro Val Ser Lys Phe Met Ser Thr Ser Val Gly Asp
1               5                   10                  15

Arg Val Ser Ile Thr Cys Lys Ala Ser Gln Asp Val Ser Thr Thr Val
            20                  25                  30

Ala Trp Tyr Gln Gln Lys Pro Gly Gln Ser Pro Lys Leu Leu Ile Tyr
        35                  40                  45

Trp Ala Ser Thr Arg His Thr Gly Val Pro Asp Arg Phe Thr Gly Ser
    50                  55                  60

Gly Ser Gly Thr Asp Tyr Ser Leu Thr Ile Ser Ser Val Gln Ala Glu
65                  70                  75                  80

Asp Leu Ala Leu Tyr Tyr Cys Gln Gln His Tyr Ser Thr Pro Tyr Thr
                85                  90                  95

Phe Gly Gly Gly Thr Lys Leu Glu Ile Lys Arg Ala Asp Ala Ala Pro
            100                 105                 110

Thr Val Ser
        115
```

<210> SEQ ID NO 88
<211> LENGTH: 122
<212> TYPE: PRT
<213> ORGANISM: Artificial Sequence
<220> FEATURE:
<223> OTHER INFORMATION: OD218B heavy chain

<400> SEQUENCE: 88

```
Leu Pro Glu Phe Gln Val Gln Leu Gln Glu Ser Gly Gly Gly Leu Glu
1               5                   10                  15
```

-continued

```
Gln Pro Gly Gly Ser Leu Lys Leu Ser Cys Ala Ala Ser Gly Phe Asp
            20                  25                  30

Phe Ser Arg Tyr Trp Met Asn Trp Val Arg Gln Ala Pro Gly Lys Gly
        35                  40                  45

Leu Glu Trp Ile Gly Glu Ile Asn Pro Asp Ser Ser Thr Ile Asn Tyr
    50                  55                  60

Thr Pro Ser Leu Lys Asp Lys Phe Ile Ile Ser Arg Asp Asn Ala Lys
65                  70                  75                  80

Asn Thr Leu Tyr Leu Gln Met Ser Lys Val Arg Ser Glu Asp Thr Ala
                85                  90                  95

Leu Tyr Tyr Cys Ala Arg Pro Met Gly Ile Thr Lys Gly Phe Ala Tyr
            100                 105                 110

Trp Gly Gln Gly Thr Leu Val Thr Ser Leu
        115                 120
```

<210> SEQ ID NO 89
<211> LENGTH: 120
<212> TYPE: PRT
<213> ORGANISM: Artificial Sequence
<220> FEATURE:
<223> OTHER INFORMATION: OD228 Light chain

<400> SEQUENCE: 89

```
Asp Ile Val Leu Thr Gln Ser Pro Ala Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Trp Thr Phe Gly Gly Gly Thr Lys Leu Glu Ile Lys Arg
            100                 105                 110

Ala Asp Ala Ala Pro Thr Val Ser
        115                 120
```

<210> SEQ ID NO 90
<211> LENGTH: 123
<212> TYPE: PRT
<213> ORGANISM: Artificial Sequence
<220> FEATURE:
<223> OTHER INFORMATION: OD228  heavy chain

<400> SEQUENCE: 90

```
Phe Arg Lys Phe Glu Val Gln Leu Gln Gln Ser Gly Ala Glu Leu Val
1               5                   10                  15

Arg Pro Gly Ala Ser Val Lys Leu Ser Cys Lys Ala Ser Gly Tyr Thr
            20                  25                  30

Phe Thr Ser Tyr Trp Met Asn Trp Val Lys Gln Arg Pro Glu Gln Gly
        35                  40                  45

Leu Glu Trp Ile Gly Arg Ile Asp Pro Tyr Ala Gly Glu Thr Gln Phe
    50                  55                  60

Asn Glu Lys Phe Lys Asp Lys Ala Ile Leu Thr Val Asp Lys Ser Ser
65                  70                  75                  80
```

Ser Thr Ala Tyr Met Gln Leu Ser Ser Leu Thr Ser Glu Asp Ser Ala
85 90 95

Val Tyr Tyr Cys Ala Arg Pro Ser Leu Leu Arg Gly Ala Met Asp Tyr
100 105 110

Trp Gly Gln Gly Thr Ser Val Thr Val Ser Ser
115 120

<210> SEQ ID NO 91
<211> LENGTH: 119
<212> TYPE: PRT
<213> ORGANISM: Artificial Sequence
<220> FEATURE:
<223> OTHER INFORMATION: OD238 light chain
<220> FEATURE:
<221> NAME/KEY: MISC_FEATURE
<222> LOCATION: (63)..(63)
<223> OTHER INFORMATION: unknown or other

<400> SEQUENCE: 91

Ser Arg Lys Leu Asp Ile Gln Leu Thr Gln Ser Pro Ser Ser Leu Ala
1 5 10 15

Met Ser Val Gly Gln Lys Val Thr Met Ser Cys Lys Ser Ser Gln Ser
20 25 30

Leu Leu Asn Ser Ser Asn Gln Lys Asn Tyr Leu Ala Trp Tyr Gln Gln
35 40 45

Lys Pro Gly Gln Ser Pro Lys Leu Leu Val Tyr Phe Ala Ser Xaa Arg
50 55 60

Lys Ser Gly Val Pro Asp Arg Phe Ile Gly Ser Gly Ser Gly Thr Asp
65 70 75 80

Phe Thr Leu Thr Ile Ser Ser Val Gln Ala Glu Asp Leu Ala Asp Tyr
85 90 95

Phe Cys Gln Gln His Tyr Thr Thr Pro Trp Thr Phe Gly Gly Gly Thr
100 105 110

Lys Leu Asn Gln Ser Trp Met
115

<210> SEQ ID NO 92
<211> LENGTH: 127
<212> TYPE: PRT
<213> ORGANISM: Artificial Sequence
<220> FEATURE:
<223> OTHER INFORMATION: OD238 Heavy chain

<400> SEQUENCE: 92

Val Lys Leu Gln Glu Ser Gly Pro Gly Ile Leu Gln Pro Ser Gln Thr
1 5 10 15

Leu Ser Leu Thr Cys Ser Phe Ser Gly Phe Ser Leu Ser Thr Tyr Asp
20 25 30

Ile Gly Val Gly Trp Ile Arg Gln Pro Ser Gly Lys Gly Leu Glu Trp
35 40 45

Leu Ser His Ile Trp Trp Asn Asp Asn Lys Tyr Tyr Asn Thr Ala Leu
50 55 60

Lys Ser Arg Leu Thr Ile Ser Lys Asp Thr Ser Asn Asn Gln Val Phe
65 70 75 80

Leu Lys Ile Ala Ser Val Asp Thr Ala Asp Thr Ala Thr Tyr Tyr Cys
85 90 95

Ser Arg Ile Gly Ser Tyr Tyr Tyr Gly Thr Ser Ser His Tyr Tyr Val
100 105 110

Met Asp Tyr Trp Gly Gln Gly Thr Ser Val Thr Val Ser Ser Ala
115 120 125

<210> SEQ ID NO 93
<211> LENGTH: 116
<212> TYPE: PRT
<213> ORGANISM: Artificial Sequence
<220> FEATURE:
<223> OTHER INFORMATION: OD243A light chain

<400> SEQUENCE: 93

Asp Ile Gln Leu Thr Gln Ser Pro Ser Ser Leu Ser Ala Ser Leu Gly
1 5 10 15

Asp Arg Val Thr Ile Ser Cys Arg Ala Ser Leu Asp Ile Ser Asn Tyr
20 25 30

Leu Asn Trp Tyr Gln Gln Lys Pro Asp Gly Thr Val Lys Leu Leu Ile
35 40 45

Tyr Tyr Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Asp Gln
65 70 75 80

Glu Asp Phe Ala Thr Tyr Phe Cys Gln Gln Gly Asn Thr Leu Pro Trp
85 90 95

Thr Phe Gly Gly Gly Thr Lys Leu Glu Ile Lys Arg Ala Asp Ala Ala
100 105 110

Pro Thr Val Ser
115

<210> SEQ ID NO 94
<211> LENGTH: 124
<212> TYPE: PRT
<213> ORGANISM: Artificial Sequence
<220> FEATURE:
<223> OTHER INFORMATION: OD243A Heavy chain

<400> SEQUENCE: 94

Leu Ser Glu Phe Glu Val Gln Leu Gln Glu Ser Gly Gly Gly Leu Val
1 5 10 15

Gln Pro Gly Arg Pro Met Lys Leu Ser Cys Val Ala Ser Gly Phe Thr
20 25 30

Phe Ser Asp Tyr Trp Met Asn Trp Val Arg Gln Ser Pro Glu Lys Arg
35 40 45

Leu Glu Trp Val Ala Gln Ile Arg Asn Lys Pro Phe Asn Tyr Glu Thr
50 55 60

Tyr Tyr Ser Asp Ser Val Lys Gly Arg Phe Thr Ile Ser Arg Asp Asp
65 70 75 80

Ser Lys Ser Ser Val Tyr Leu Gln Met Asn Asn Leu Arg Ala Glu Asp
85 90 95

Met Gly Ile Tyr Tyr Cys Thr Ser Ile Gly Tyr Asp Gly Ser Phe Ala
100 105 110

Tyr Trp Gly Gln Gly Thr Leu Val Thr Ser Ala Gly
115 120

<210> SEQ ID NO 95
<211> LENGTH: 121
<212> TYPE: PRT
<213> ORGANISM: Artificial Sequence
<220> FEATURE:
<223> OTHER INFORMATION: OD256 light chain

<400> SEQUENCE: 95

Asp Ile Gln Leu Thr Gln Ser Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Asn Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Val Pro Phe Thr Phe Gly Ser Gly Thr Glu Leu Glu Ile Lys
100 105 110

Arg Ala Asp Ala Ala Pro Thr Val Ser
115 120

<210> SEQ ID NO 96
<211> LENGTH: 120
<212> TYPE: PRT
<213> ORGANISM: Artificial Sequence
<220> FEATURE:
<223> OTHER INFORMATION: OD256 Heavy chain

<400> SEQUENCE: 96

Phe Arg Lys Ile Glu Val Gln Leu Gln Glu Ser Gly Pro Glu Leu Val
1 5 10 15

Lys Pro Gly Ala Ser Val Lys Met Ser Cys Lys Ala Ser Gly Tyr Thr
20 25 30

Phe Thr Ser Tyr Val Met His Trp Val Lys Gln Lys Pro Gly Gln Gly
35 40 45

Leu Glu Trp Ile Gly Tyr Ile Asn Pro Tyr Asn Asp Gly Thr Lys Tyr
50 55 60

Asn Glu Lys Phe Lys Gly Lys Ala Thr Leu Thr Ser Asp Lys Ser Ser
65 70 75 80

Ser Thr Ala Tyr Met Glu Leu Ser Ser Leu Thr Ser Glu Asp Ser Ala
85 90 95

Val Tyr Tyr Cys Ala Arg Gly Tyr Gly Leu Gly Asp Tyr Trp Gly Gln
100 105 110

Gly Thr Ser Val Thr Val Ser Ser
115 120

<210> SEQ ID NO 97
<211> LENGTH: 335
<212> TYPE: DNA
<213> ORGANISM: Artificial Sequence
<220> FEATURE:
<223> OTHER INFORMATION: OD40 light chain

<400> SEQUENCE: 97
ttttcggaag cttgacattc agctgaccca gtctccagcc tccctatctg tatctgtggg 60
agaaactgtc accatcacat gtcgagcaag tgagaatatt tacagtcatt tagcatggta 120
tcaggagaaa cagggaaaat ctcctcagct cctggtctat gctgcaacaa acttagcaga 180
tggtgtgcca tcaaggttca gtggcagtgg atcaggcaca cagtattccc tcaagatcaa 240
cagattgcag tctgaagatt ttgggagtta ttactgtcaa catttttggg gtactcttcc 300
aacgttcgga gggggaccaa gtgaaaaaag cggtt 335

<210> SEQ ID NO 98
<211> LENGTH: 374
<212> TYPE: DNA
<213> ORGANISM: Artificial Sequence
<220> FEATURE:
<223> OTHER INFORMATION: OD40 heavy chain

<400> SEQUENCE: 98
tcttccggaa atttgaggtt cagctgcagg agtctggccc tgggatattg cagccctccc 60
agaccctcag tctgacttgt tctttctctg ggttttcact gagcacttat ggtataggag 120
taggctggat tcgtcagcct tcagggaagg gtctggagtg gctggcacac atttggtgga 180
atgataataa gtactataac acagccctga agagtcggct cacaatctcc aaggatatct 240
ccaacaacca ggtattcctc aagattgtca gtgtggacac tgcagatact gccacatatt 300
actgtgctcg aattctatgg ttacgacgac ctatggacta ctggggtcaa ggaacctcag 360
tcatcgtctc ctca 374

<210> SEQ ID NO 99
<211> LENGTH: 352
<212> TYPE: DNA
<213> ORGANISM: Artificial Sequence
<220> FEATURE:
<223> OTHER INFORMATION: OD46 light chain

<400> SEQUENCE: 99
cggaagcttg acattcagct gacccagtct ccatcctccc tggctatgtc agtaggacag 60
aaggtcacta tgagctgcaa gtccagtcag agccttttaa atagtagcaa tcaaaagaac 120
tatttggcct ggtaccagca gaaaccagga cagtctccta aacttctggt atactttgca 180
tccgctagga aatctggggt ccctgatcgc ttcataggca gtggatctgg gacagatttc 240
actcttacca tcagcagtgt gcaggctgaa gacctggcag attacttctg tcagcaacat 300
tataccactc cgtggacgtt cggtggaggc accaagctga atcaaacggg tt 352

<210> SEQ ID NO 100
<211> LENGTH: 383
<212> TYPE: DNA
<213> ORGANISM: Artificial Sequence
<220> FEATURE:
<223> OTHER INFORMATION: OD46 heavy chain

<400> SEQUENCE: 100
tcttccggaa aattgaggtt cagctgcagc agtctggggc tgagctggtg aggcctgggt 60
cctcagtgaa gatttcctgt aaggcttctg gctatgcatt cagtagctac tggatgaact 120
gggtgaagca gaggcctgga cagggtcttg agtggattgg acagatctat cctggagatg 180
gtgattctaa ctacaatgga aagttcaagg gtaaagccac actgactgca gacaaatcct 240
ccagtatagc ctacatgcag ctcagcagcc tgacgtctga ggactctgcg gtctatttct 300
gtgcaagatt cggttctacg gctacggctg actactgggg ccaaggcacc actctcacag 360
tctcctcagc caaaacaaca gcc 383

<210> SEQ ID NO 101
<211> LENGTH: 318
<212> TYPE: DNA
<213> ORGANISM: Artificial Sequence
<220> FEATURE:

<223> OTHER INFORMATION: OD82B light chain

<400> SEQUENCE: 101
tttcggaagc ttgacattca gctgacccag tctccagcac tcatgtctgc atctccaggg 60
gagaaggtca ccatgacctg cagtgccagc tcaagtgtaa gttacatgaa ctggtaccag 120
cagaagccaa gatcctcccc caaaccctgg atttatctca catccaacct ggcttctgga 180
gtccctgctc gcttcagtgg cagtgggtct gggacctctt actctctcac aatcagcaac 240
atggaggctg aagatgctgc cacttattac tgccagcagt ggagtagtaa cccgctcacg 300
ttcggtgctg gaccaagc 318

<210> SEQ ID NO 102
<211> LENGTH: 364
<212> TYPE: DNA
<213> ORGANISM: Artificial Sequence
<220> FEATURE:
<223> OTHER INFORMATION: OD82B heavy chain

<400> SEQUENCE: 102
tcttccggaa ttccaggttc agctggagca gtctggggct gaactggcaa aacctggggc 60
ctcagtgaag atgtcctgca aggcttctgg ctacaccttt gctagctatt ggatgcactg 120
gatgaaacag aggcctggac agggtctgga atggattggc tacattaatc ctagcactgt 180
ttatactgag tacaatcaga agttcaagga caaggcctca ttgactgcag acacatcctc 240
cagcacagcc tacatgcaac tgagcagcct gacatctgag gactctgcag tctattactg 300
tgcaagatct aggtacgacg ggtttgctta ctggggccaa gggactctgg tcacgtctcc 360
tgcc 364

<210> SEQ ID NO 103
<211> LENGTH: 337
<212> TYPE: DNA
<213> ORGANISM: Artificial Sequence
<220> FEATURE:
<223> OTHER INFORMATION: OD142B light chain

<400> SEQUENCE: 103
gacccagtct ccaaaattcc tgcttgtgtc agcaggggac agggttacca taacctgcaa 60
ggccagtcag agtgtgagta atgatgtagc ttggtaccaa cagaagccag gacagtctcc 120
taaactgctg atatactatg catccaatcg ctacactgga gtccctgatc gcttcactgg 180
cagtggatat gggacggatt tcactttcac catcaacact atgcaggctg aagacctggc 240
agtttatttc tgtcagcagg attatagctc tccgtacacg ttcggagggg ggaccaagct 300
ggaaataaaa cgggctgatg ctgcaccaac tgtatcc 337

<210> SEQ ID NO 104
<211> LENGTH: 375
<212> TYPE: DNA
<213> ORGANISM: Artificial Sequence
<220> FEATURE:
<223> OTHER INFORMATION: OD142B heavy chain

<400> SEQUENCE: 104
tctttcggaa ttttgaggtt cagctgcagc agtctggggg aggcttagtg aagcctggag 60
ggtccctgaa actctcctgt gcagcctctg gattcacttt cagtagctat gccatgtctt 120
gggttcgcca gactccggag aagaggctgg agtgggtcgc aaccattagt agtggtggta 180
gttacaccta ctatccagac agtgtgaagg gtcgattcac catctccaga gacaatgcca 240

-continued agaacaccct gtacctgcaa atgagcagtc tgaggtctga ggacacggcc atgtattact 300
gtgcaagacg gagttacgac gggggaggcg tctggtttgc ttactggggc caagggactc 360
tggtcacgtc tctga 375

<210> SEQ ID NO 105
<211> LENGTH: 351
<212> TYPE: DNA
<213> ORGANISM: Artificial Sequence
<220> FEATURE:
<223> OTHER INFORMATION: OD142D light chain

<400> SEQUENCE: 105
ttttcggaag cttgacattc agctgaccca gtctccatcc tccctggcta tgtcagtagg 60
acagaaggtc actatgagct gcaagtccag tcagagcctt ttaaatagta gcaatcaaaa 120
gaactatttg gcctggtacc agcagaaacc aggacagtct cctaaacttc tggtatactt 180
tgcatccgct aggaaatctg ggtccctga tcgcttcata ggcagtggat ctgggacaga 240
tttcactctt accatcagca gtgtgcaggc tgaagacctg gcagattact tctgtcagca 300
acattatacc actccgtgsa cgttcggtgg aggcaccaag ctgaatcaag c 351

<210> SEQ ID NO 106
<211> LENGTH: 374
<212> TYPE: DNA
<213> ORGANISM: Artificial Sequence
<220> FEATURE:
<223> OTHER INFORMATION: OD142D heavy chain

<400> SEQUENCE: 106
ttccggaaat ttgaggttca gctgcagcag tcagggggag gcttagtgaa gcctggaggg 60
tccctgaaac tctcctgtgc agcctctgga ttcactttca gtagctatgc catgtcttgg 120
gttcgccaga ctccggagaa gaggctggag tgggtcgcaa ccattagtag tggtggtagt 180
tacacctact atccagacag tgtgaagggt cgattcacca tctccagaga caatgccaag 240
aacaccctgt acctgcaaat gagcagtctg aggtctgagg acacggccat gtattactgt 300
gcaagacgga gttacgacgg gggaggcgtc tggtttgctt actggggcca agggactctg 360
gtcacgtctc tgca 374

<210> SEQ ID NO 107
<211> LENGTH: 334
<212> TYPE: DNA
<213> ORGANISM: Artificial Sequence
<220> FEATURE:
<223> OTHER INFORMATION: OD149A light chain

<400> SEQUENCE: 107
cggaagcttg acattcagct gacccagtct ccaaaattca tgtccacatc agtaggagac 60
agggtcagcg tcacctgcaa ggccagtcag aatgtgggta ctaatgttgc ctggtatcaa 120
cagaaaccag ggcaatctcc taaagcactg atttactcgg catcctaccg gtacagtgga 180
gtccctgatc gcttcacagg cagtggatct gggacagatt tcactctcac catcagcaat 240
gtgcagtctg aagacttggc agagtatttc tgtcagcaat ataacagcta tccgctcacg 300
ttcggtgctg gaccaagctg agcmaagtcg ggtt 334

<210> SEQ ID NO 108
<211> LENGTH: 363
<212> TYPE: DNA

-continued

<213> ORGANISM: Artificial Sequence
<220> FEATURE:
<223> OTHER INFORMATION: OD149A heavy chain

<400> SEQUENCE: 108
tcttccggaa ttttgaggtt cagctgcagg agtctgggac tgagctggtg aggcctgggg 60
cttcagtgaa gctgtcctgc aaggctttgg gctacacatt tattgactat gaaatgcact 120
gggtgaagca gacacctgtg catggcctgg aatggattgg agctattcat ccaggaagtg 180
gtggtactgc ctacaatcag aacttcaagg gcaaggccac actgactgca gacaaatcct 240
ccagcacagc ctacatggag ctcagcagcc tgacatctga ggactctgct gtctattact 300
gtacaacgta tggtaactac tttgactact ggggccaagg caccactctc acagtctccc 360
taa 363

<210> SEQ ID NO 109
<211> LENGTH: 336
<212> TYPE: DNA
<213> ORGANISM: Artificial sequence
<220> FEATURE:
<223> OTHER INFORMATION: OD218A light chain

<400> SEQUENCE: 109
tatcggaagc ttgacattca gctgacccag tctccagcaa tcctgtctgc atttccaggg 60
gagaaggtca caatgacttg cagggccagt tcaagtgtaa gttacatgaa ttggtaccag 120
cagaagccag gatcctcccc caaaccctgg atttatgcca catccaacct ggcttctgga 180
gtccctgctc gcttcagtgg cagtgggtct ggggcctctt actctctcac aatcagcaga 240
gtggaggctg aagatgctgc cacttattac tgccagcagt ggagtagtaa cccaccgtac 300
acgttcggag gggggaccaag ctgaaataat cgggtt 336

<210> SEQ ID NO 110
<211> LENGTH: 369
<212> TYPE: DNA
<213> ORGANISM: Artificial sequence
<220> FEATURE:
<223> OTHER INFORMATION: OD218A heavy chain

<400> SEQUENCE: 110
cttccggaat tccaggttca gctgcaggag tctggaggtg gcctggagca gcctggagga 60
tccctgaaac tctcctgtgc agcctcagga ttcgatttca gtagatactg gatgaattgg 120
gtccggcagg ctccagggaa agggctagaa tggattggag aaattaatcc agatagcagt 180
acgataaact atacgccatc tctaaaggat aaattcatca tctccagaga caacgccaaa 240
aatacgctgt acctgcaaat gagcaaagtg agatctgagg acacagccct ttattactgt 300
gcaagaccta tggggattac gaaggggttt gcttactggg gccaagggac tctggtcacg 360
tctcttgca 369

<210> SEQ ID NO 111
<211> LENGTH: 347
<212> TYPE: DNA
<213> ORGANISM: Artificial Sequence
<220> FEATURE:
<223> OTHER INFORMATION: OD218B light chain

<400> SEQUENCE: 111
gacattcagc tgacccagtc tccaaattca tgtccacatc agtaggagac agggtcagca 60
tcacctgcaa ggccagtcag gatgtgagta ctactgtagc ctggtatcaa caaaaaccag 120

```
gacaatctcc taaactactg atttactggg catccacccg gcacactgga gtccctgatc    180

gcttcacagg cagtggatct gggacagatt atagtctaac catcagcagt gtgcaggctg    240

aagacctggc actttattac tgtcagcaac attatagcac tccgtacacg ttcggagggg    300

ggaccaagct ggaaataaaa cgggctgatg ctgcaccaac tgtatcc                  347


<210> SEQ ID NO 112
<211> LENGTH: 369
<212> TYPE: DNA
<213> ORGANISM: Artificial Sequence
<220> FEATURE:
<223> OTHER INFORMATION: OD218B heavy chain

<400> SEQUENCE: 112

tcttccggaa ttccaggttc agctgcagga gtctggaggt ggcctggagc agcctggagg     60

atccctgaaa ctctcctgtg cagcctcagg attcgatttc agtagatact ggatgaattg    120

ggtccggcag gctccaggga aagggctaga atggattgga gaaattaatc cagatagcag    180

tacgataaac tatacgccat ctctaaagga taaattcatc atctccagag acaacgccaa    240

aaatacgctg tacctgcaaa tgagcaaagt gagatctgag gacacagccc tttattactg    300

tgcaagacct atggggatta cgaaggggtt tgcttactgg ggccaaggga ctctggtcac    360

gtctctgca                                                            369


<210> SEQ ID NO 113
<211> LENGTH: 360
<212> TYPE: DNA
<213> ORGANISM: Artificial Sequence
<220> FEATURE:
<223> OTHER INFORMATION: OD228 light chain

<400> SEQUENCE: 113

gacattgtgc tgacccaatc tccagcttct ctggctgtgt ctgcaggaga aaaggtcact     60

atgagctgta agtccagtca aagtgtttta tacagttcaa atcagaagaa ctacttggcc    120

tggtaccagc agaaaccagg gcagtctcct aaactgctga tctactgggc atccactagg    180

gaatctggtg tccctgatcg cttcacaggc agtggatctg ggacagattt tactcttacc    240

atcagcagtg tacaagctga agacctggca gtttattact gtcatcaata cctctcctgg    300

acgttcggtg gaggcaccaa gctggaaatc aaacgggctg atgctgcacc aactgtatcc    360


<210> SEQ ID NO 114
<211> LENGTH: 346
<212> TYPE: DNA
<213> ORGANISM: Artificial Sequence
<220> FEATURE:
<223> OTHER INFORMATION: OD228 heavy chain

<400> SEQUENCE: 114

gacattcagc tgacccagtc tccagcatcc ctgtccgtgg caacaggaga aaaagtcact     60

atcagatgca taagcagcac tgatattgat gatgatatga actggtaaca gcagaagcca    120

ggggaacctc caaaactcct tatttcagag ggcaatagtc ttcgtcctgg agtcccatcc    180

cgattctcca gcagtggcta tggcacagat gttgttttta caattgaaaa aacgctctca    240

gaagatgttg cagattacta ctgtttgcaa agtgataaca tgccacacgt tcggaggggg    300

gaccaagctg gaaataaaac gggctgatgc tgcaccaact gtatcc                   346


<210> SEQ ID NO 115
```

<211> LENGTH: 357
<212> TYPE: DNA
<213> ORGANISM: Artificial Sequence
<220> FEATURE:
<223> OTHER INFORMATION: OD238 light chain

<400> SEQUENCE: 115
tctcggaagc ttgacattca gctgacccag tctccatcct ccctggctat gtcagtagga 60
cagaaggtca ctatgagctg caagtccagt cagagccttt taaatagtag caatcaaaag 120
aactatttgg cctggtacca gcagaaacca ggacagtctc ctaaacttct ggtatacttt 180
gcatccgyta ggaaatctgg ggtccctgat cgcttcatag gcagtggatc tgggacagat 240
ttcactctta ccatcagcag tgtgcaggct gaagacctgg cagattactt ctgtcagcaa 300
cattatacca ctccgtggac gttcggtgga ggcaccaagc tgaatcaaag ctggatg 357

<210> SEQ ID NO 116
<211> LENGTH: 407
<212> TYPE: DNA
<213> ORGANISM: Artificial Sequence
<220> FEATURE:
<223> OTHER INFORMATION: OD238 heavy chain

<400> SEQUENCE: 116
caagtcaagc tgcaggagtc tggccctggg atattgcagc cctcccagac cctcagtctg 60
acttgttctt tctctgggtt ttcactgagc acttatgata taggagtagg ctggattcgt 120
cagccttcag ggaagggtct ggagtggctg tcacacattt ggtggaatga taataagtac 180
tataacacag ccctgaagag ccggctcaca atctccaagg atacctccaa caaccaggta 240
ttcctcaaga tcgccagtgt ggacactgca gacactgcca catactactg ttctcgaata 300
ggttcctatt actatggtac tagctcccat tactatgtta tggactactg gggtcaggaa 360
cctcagtcac cgtctcctca gccaaaacga cacccccatc tgtctat 407

<210> SEQ ID NO 117
<211> LENGTH: 348
<212> TYPE: DNA
<213> ORGANISM: Artificial Sequence
<220> FEATURE:
<223> OTHER INFORMATION: OD243A light chain

<400> SEQUENCE: 117
gacattcagc tgacccagtc tccatcctcc ctgtctgcct ctctgggaga cagagtcacc 60
atcagttgca gggcaagtct ggacattagc aattatttaa actggtatca gcagaagcca 120
gatggaactg ttaaactcct gatctactac acatcaagat tacactcagg agtcccatca 180
aggttcagtg gcagtgggtc tggaacagat tattctctca ccattagcaa cctggaccaa 240
gaagattttg ccacttactt ttgccaacag ggtaatacgc ttccgtggac gttcggtgga 300
ggcaccaagc tggaaatcaa acgggctgat gctgcaccaa ctgtatcc 348

<210> SEQ ID NO 118
<211> LENGTH: 374
<212> TYPE: DNA
<213> ORGANISM: Artificial Sequence
<220> FEATURE:
<223> OTHER INFORMATION: OD243A heavy chain

<400> SEQUENCE: 118
tctttcggaa tttgaggttc agctgcagga gtctggagga ggcctggtgc aacctgggag 60
gcccatgaaa ctctcctgtg ttgcctctgg attcactttt agtgactact ggatgaactg 120

-continued ggtccgccag tctccagaga aacgactgga gtgggtagca caaattagaa acaaaccttt 180
taattatgaa acatattatt cagattctgt gaaaggcaga ttcaccatct caagagatga 240
ttccaaaagt agtgtctacc tgcaaatgaa caacttaaga gctgaagaca tgggtatcta 300
ttactgtaca tccatagggt acgacgggtc gtttgcttac tggggccaag ggactctggt 360
cacgtctgct ggca 374

<210> SEQ ID NO 119
<211> LENGTH: 363
<212> TYPE: DNA
<213> ORGANISM: Artificial Sequence
<220> FEATURE:
<223> OTHER INFORMATION: OD256 light chain

<400> SEQUENCE: 119
gacattcagc tgacccagtc tccactctcc ctgcctgtca gtcttggaga tcaagcctcc 60
atctcttgca gatctagtca gagccttgta cacagtaatg gaaacaccta tttacattgg 120
tacctgcaga agccaggcca gtctccaaag ctcctgatct acaaagtttc caaccgattt 180
tctggggtcc cagacaggtt caatggcagt ggatcaggga cagatttcac actcaagatc 240
agcagggtgg aggctgagga tctgggagtt tatttctgct ctcaaagtac acatgttcct 300
ttcacgttcg gctcggggac agagttggaa ataaaacggg ctgatgctgc accaactgta 360
tcc 363

<210> SEQ ID NO 120
<211> LENGTH: 362
<212> TYPE: DNA
<213> ORGANISM: Artificial Sequence
<220> FEATURE:
<223> OTHER INFORMATION: OD256 heavy chain

<400> SEQUENCE: 120
tcttccggaa aatcgaggtt cagctgcagg agtctggacc tgagctggta aagcctgggg 60
cttcagtgaa gatgtcctgc aaggcttctg gatacacatt cactagctat gttatgcact 120
gggtgaagca gaagcctggg cagggccttg agtggattgg atatattaat ccttacaatg 180
atggtactaa gtacaatgag aagttcaaag gcaaggccac actgacttca gacaaatcct 240
ccagcacagc ctacatggag ctcagcagcc tgacctctga ggactctgcg gtctattact 300
gtgcaagggg ctatggcctc ggggactact ggggtcaagg aacctcagtc accgtctcct 360
ca 362

<210> SEQ ID NO 121
<211> LENGTH: 11
<212> TYPE: PRT
<213> ORGANISM: Artificial Sequence
<220> FEATURE:
<223> OTHER INFORMATION: OD7 Light chain CDR1

<400> SEQUENCE: 121

Arg Ala Ser Gln Ser Ile Ser Asn Asn Leu His
1               5                   10

<210> SEQ ID NO 122
<211> LENGTH: 7
<212> TYPE: PRT
<213> ORGANISM: Artificial Sequence
<220> FEATURE:
<223> OTHER INFORMATION: OD7 Light chain CDR2

<400> SEQUENCE: 122

Tyr Ala Ser Gln Ser Ile Ser
1 5

<210> SEQ ID NO 123
<211> LENGTH: 9
<212> TYPE: PRT
<213> ORGANISM: Artificial Sequence
<220> FEATURE:
<223> OTHER INFORMATION: OD7 Light chain CDR3

<400> SEQUENCE: 123

Gln Gln Ser Asn Ser Trp Pro Leu Thr
1 5

<210> SEQ ID NO 124
<211> LENGTH: 10
<212> TYPE: PRT
<213> ORGANISM: Artificial Sequence
<220> FEATURE:
<223> OTHER INFORMATION: OD7 Heavy chain CDR1

<400> SEQUENCE: 124

Gly Tyr Ser Phe Thr Ser Tyr Trp Met Asn
1 5 10

<210> SEQ ID NO 125
<211> LENGTH: 17
<212> TYPE: PRT
<213> ORGANISM: Artificial Sequence
<220> FEATURE:
<223> OTHER INFORMATION: OD7 Heavy chain CDR2

<400> SEQUENCE: 125

Met Ile His Pro Ser Asp Ser Glu Thr Arg Leu Asn Gln Lys Phe Lys
1 5 10 15

Asp

<210> SEQ ID NO 126
<211> LENGTH: 13
<212> TYPE: PRT
<213> ORGANISM: Artificial Sequence
<220> FEATURE:
<223> OTHER INFORMATION: OD7 Heavy chain CDR3

<400> SEQUENCE: 126

Pro Val Val Ala Thr Gly Arg Tyr Tyr Ser Met Asp Tyr
1 5 10

<210> SEQ ID NO 127
<211> LENGTH: 11
<212> TYPE: PRT
<213> ORGANISM: Artificial Sequence
<220> FEATURE:
<223> OTHER INFORMATION: OD111A Light chain CDR1

<400> SEQUENCE: 127

Arg Ala Ser Glu Asn Ile Tyr Ser Tyr Leu Ala
1 5 10

<210> SEQ ID NO 128
<211> LENGTH: 7
<212> TYPE: PRT
<213> ORGANISM: Artificial Sequence
<220> FEATURE:

<223> OTHER INFORMATION: OD111A Light chain CDR2

<400> SEQUENCE: 128

Asn Ala Lys Thr Leu Ala Glu
1 5

<210> SEQ ID NO 129
<211> LENGTH: 9
<212> TYPE: PRT
<213> ORGANISM: Artificial Sequence
<220> FEATURE:
<223> OTHER INFORMATION: OD111A Light chain CDR3

<400> SEQUENCE: 129

Gln His His Tyr Gly Thr Pro Leu Thr
1 5

<210> SEQ ID NO 130
<211> LENGTH: 10
<212> TYPE: PRT
<213> ORGANISM: Artificial Sequence
<220> FEATURE:
<223> OTHER INFORMATION: OD111A Heavy chain CDR1

<400> SEQUENCE: 130

Gly Tyr Thr Phe Ser Ser Tyr Trp Ile Glu
1 5 10

<210> SEQ ID NO 131
<211> LENGTH: 17
<212> TYPE: PRT
<213> ORGANISM: Artificial Sequence
<220> FEATURE:
<223> OTHER INFORMATION: OD111A Heavy chain CDR2

<400> SEQUENCE: 131

Glu Ile Leu Pro Gly Ser Gly Ser Thr Asn Tyr Asn Glu Lys Phe Lys
1 5 10 15

Gly

<210> SEQ ID NO 132
<211> LENGTH: 14
<212> TYPE: PRT
<213> ORGANISM: Artificial Sequence
<220> FEATURE:
<223> OTHER INFORMATION: OD111A Heavy chain CDR3

<400> SEQUENCE: 132

Arg Lys Trp Gly Asn Tyr Val Asn Tyr Tyr Ala Met Asp Tyr
1 5 10

<210> SEQ ID NO 133
<211> LENGTH: 10
<212> TYPE: PRT
<213> ORGANISM: Artificial Sequence
<220> FEATURE:
<223> OTHER INFORMATION: OD169B Light chain CDR1

<400> SEQUENCE: 133

Ser Ala Ser Ser Ser Val Ser Tyr Met His
1 5 10

<210> SEQ ID NO 134
<211> LENGTH: 7
<212> TYPE: PRT
<213> ORGANISM: Artificial Sequence -continued
<220> FEATURE:
<223> OTHER INFORMATION: OD169B Light chain CDR2

<400> SEQUENCE: 134

Asp Thr Ser Lys Leu Ala Ser
1               5

<210> SEQ ID NO 135
<211> LENGTH: 9
<212> TYPE: PRT
<213> ORGANISM: Artificial Sequence
<220> FEATURE:
<223> OTHER INFORMATION: OD169B Light chain CDR3

<400> SEQUENCE: 135

Gln Gln Trp Ser Ser Asn Pro Pro Thr
1               5

<210> SEQ ID NO 136
<211> LENGTH: 10
<212> TYPE: PRT
<213> ORGANISM: Artificial Sequence
<220> FEATURE:
<223> OTHER INFORMATION: OD169B Heavy chain CDR1

<400> SEQUENCE: 136

Gly Phe Ser Leu Thr Ser Tyr Gly Val Ser
1               5                   10

<210> SEQ ID NO 137
<211> LENGTH: 16
<212> TYPE: PRT
<213> ORGANISM: Artificial Sequence
<220> FEATURE:
<223> OTHER INFORMATION: OD169B Heavy chain CDR2

<400> SEQUENCE: 137

Val Ile Trp Gly Asp Gly Ser Thr Asn Tyr His Ser Ala Leu Ile Ser
1               5                   10                  15

<210> SEQ ID NO 138
<211> LENGTH: 4
<212> TYPE: PRT
<213> ORGANISM: Artificial Sequence
<220> FEATURE:
<223> OTHER INFORMATION: OD169B Heavy chain CDR3

<400> SEQUENCE: 138

Tyr Arg Gly Tyr
1

<210> SEQ ID NO 139
<211> LENGTH: 16
<212> TYPE: PRT
<213> ORGANISM: Artificial Sequence
<220> FEATURE:
<223> OTHER INFORMATION: OD184 Light chain CDR1

<400> SEQUENCE: 139

Arg Ser Ser Lys Ser Leu Leu His Ser Asn Gly Ile Thr Tyr Leu Tyr
1               5                   10                  15

<210> SEQ ID NO 140
<211> LENGTH: 7
<212> TYPE: PRT
<213> ORGANISM: Artificial Sequence
<220> FEATURE:

<223> OTHER INFORMATION: OD184 Light chain CDR2

<400> SEQUENCE: 140

Gln Met Ser Asn Leu Ala Ser
1 5

<210> SEQ ID NO 141
<211> LENGTH: 9
<212> TYPE: PRT
<213> ORGANISM: Artificial Sequence
<220> FEATURE:
<223> OTHER INFORMATION: OD184 Light chain CDR3

<400> SEQUENCE: 141

Ala Gln Asn Leu Glu Leu Pro Pro Thr
1 5

<210> SEQ ID NO 142
<211> LENGTH: 11
<212> TYPE: PRT
<213> ORGANISM: Artificial Sequence
<220> FEATURE:
<223> OTHER INFORMATION: OD184 Heavy chain CDR1

<400> SEQUENCE: 142

Asp Ser Glu Val Phe Pro Ile Ala Tyr Met Ser
1 5 10

<210> SEQ ID NO 143
<211> LENGTH: 17
<212> TYPE: PRT
<213> ORGANISM: Artificial Sequence
<220> FEATURE:
<223> OTHER INFORMATION: OD184 Heavy chain CDR2

<400> SEQUENCE: 143

Asp Ile Leu Pro Ser Ile Gly Arg Thr Ile Tyr Gly Glu Lys Phe Glu
1 5 10 15

Asp

<210> SEQ ID NO 144
<211> LENGTH: 12
<212> TYPE: PRT
<213> ORGANISM: Artificial Sequence
<220> FEATURE:
<223> OTHER INFORMATION: OD184 Heavy chain CDR3

<400> SEQUENCE: 144

Glu Gly Ser Ser Gly Tyr Gly Ala Trp Phe Ala Tyr
1 5 10

<210> SEQ ID NO 145
<211> LENGTH: 17
<212> TYPE: PRT
<213> ORGANISM: Artificial Sequence
<220> FEATURE:
<223> OTHER INFORMATION: OD185 Light chain CDR1

<400> SEQUENCE: 145

Lys Ser Ser Gln Ser Leu Leu Asn Ser Gly Asn Gln Lys Asn Tyr Leu
1 5 10 15

Ala

<210> SEQ ID NO 146
<211> LENGTH: 7

<212> TYPE: PRT
<213> ORGANISM: Artificial Sequence
<220> FEATURE:
<223> OTHER INFORMATION: OD185 Light chain CDR2

<400> SEQUENCE: 146

Gly Ala Ser Thr Arg Glu Ser
1 5

<210> SEQ ID NO 147
<211> LENGTH: 9
<212> TYPE: PRT
<213> ORGANISM: Artificial Sequence
<220> FEATURE:
<223> OTHER INFORMATION: OD185 Light chain CDR3

<400> SEQUENCE: 147

Gln Asn Asp His Ser Tyr Pro Tyr Thr
1 5

<210> SEQ ID NO 148
<211> LENGTH: 12
<212> TYPE: PRT
<213> ORGANISM: Artificial Sequence
<220> FEATURE:
<223> OTHER INFORMATION: OD185 Heavy chain CDR1

<400> SEQUENCE: 148

Gly Phe Ser Leu Ser Thr Ser Gly Met Gly Val Gly
1 5 10

<210> SEQ ID NO 149
<211> LENGTH: 16
<212> TYPE: PRT
<213> ORGANISM: Artificial Sequence
<220> FEATURE:
<223> OTHER INFORMATION: OD185 Heavy chain CDR2

<400> SEQUENCE: 149

His Ile Trp Trp Asp Asp Asp Lys Arg Tyr Asn Pro Ala Leu Lys Ser
1 5 10 15

<210> SEQ ID NO 150
<211> LENGTH: 12
<212> TYPE: PRT
<213> ORGANISM: Artificial Sequence
<220> FEATURE:
<223> OTHER INFORMATION: OD185 Heavy chain CDR3

<400> SEQUENCE: 150

Ile Glu Asp Ser Leu Leu Pro Leu Gly Phe Ala Tyr
1 5 10

<210> SEQ ID NO 151
<211> LENGTH: 11
<212> TYPE: PRT
<213> ORGANISM: Artificial Sequence
<220> FEATURE:
<223> OTHER INFORMATION: OD196 Light chain CDR1

<400> SEQUENCE: 151

Lys Ala Ser Gln Asn Val Gly Thr Asn Val Ala
1 5 10

<210> SEQ ID NO 152
<211> LENGTH: 7
<212> TYPE: PRT

<213> ORGANISM: Artificial Sequence
<220> FEATURE:
<223> OTHER INFORMATION: OD196 Light chain CDR2

<400> SEQUENCE: 152

Ser Ala Ser Tyr Arg Tyr Ser
1 5

<210> SEQ ID NO 153
<211> LENGTH: 9
<212> TYPE: PRT
<213> ORGANISM: Artificial Sequence
<220> FEATURE:
<223> OTHER INFORMATION: OD196 Light chain CDR3

<400> SEQUENCE: 153

Gln Gln Tyr Asn Ser Tyr Pro Tyr Thr
1 5

<210> SEQ ID NO 154
<211> LENGTH: 10
<212> TYPE: PRT
<213> ORGANISM: Artificial Sequence
<220> FEATURE:
<223> OTHER INFORMATION: OD196 Heavy chain CDR1

<400> SEQUENCE: 154

Gly Tyr Thr Phe Thr Glu Tyr Thr Met His
1 5 10

<210> SEQ ID NO 155
<211> LENGTH: 17
<212> TYPE: PRT
<213> ORGANISM: Artificial Sequence
<220> FEATURE:
<223> OTHER INFORMATION: OD196 Heavy chain CDR2

<400> SEQUENCE: 155

Gly Ile Asn Pro Asn Asn Gly Gly Thr Ser Tyr Asn Gln Lys Phe Lys
1 5 10 15

Gly

<210> SEQ ID NO 156
<211> LENGTH: 6
<212> TYPE: PRT
<213> ORGANISM: Artificial Sequence
<220> FEATURE:
<223> OTHER INFORMATION: OD196 Heavy chain CDR3

<400> SEQUENCE: 156

Gly Tyr Ala Met Asp Tyr
1 5

<210> SEQ ID NO 157
<211> LENGTH: 15
<212> TYPE: PRT
<213> ORGANISM: Artificial Sequence
<220> FEATURE:
<223> OTHER INFORMATION: OD210A Light chain CDR1

<400> SEQUENCE: 157

Arg Ala Ser Glu Ser Val Asp Asn Tyr Gly Ile Ser Phe Met Asn
1 5 10 15

<210> SEQ ID NO 158
<211> LENGTH: 7

<212> TYPE: PRT
<213> ORGANISM: Artificial Sequence
<220> FEATURE:
<223> OTHER INFORMATION: OD210A Light chain CDR2

<400> SEQUENCE: 158

Ala Ala Ser Asn Gln Gly Ser
1               5

<210> SEQ ID NO 159
<211> LENGTH: 9
<212> TYPE: PRT
<213> ORGANISM: Artificial Sequence
<220> FEATURE:
<223> OTHER INFORMATION: OD210A Light chain CDR3

<400> SEQUENCE: 159

Gln Gln Ser Lys Glu Val Pro Arg Thr
1               5

<210> SEQ ID NO 160
<211> LENGTH: 10
<212> TYPE: PRT
<213> ORGANISM: Artificial Sequence
<220> FEATURE:
<223> OTHER INFORMATION: OD210A Heavy chain CDR1

<400> SEQUENCE: 160

Gly Phe Asp Phe Ser Arg Tyr Trp Met Ser
1               5                   10

<210> SEQ ID NO 161
<211> LENGTH: 17
<212> TYPE: PRT
<213> ORGANISM: Artificial Sequence
<220> FEATURE:
<223> OTHER INFORMATION: OD210A Heavy chain CDR2

<400> SEQUENCE: 161

Glu Ile Asn Pro Asp Ser Ser Thr Ile Asn Tyr Thr Pro Ser Leu Lys
1               5                   10                  15

Asp

<210> SEQ ID NO 162
<211> LENGTH: 11
<212> TYPE: PRT
<213> ORGANISM: Artificial Sequence
<220> FEATURE:
<223> OTHER INFORMATION: OD210A Heavy chain CDR3

<400> SEQUENCE: 162

Arg Gly Ile Tyr Tyr Gly Asn Tyr Cys Asp Tyr
1               5                   10

<210> SEQ ID NO 163
<211> LENGTH: 17
<212> TYPE: PRT
<213> ORGANISM: Artificial Sequence
<220> FEATURE:
<223> OTHER INFORMATION: OD225 Light chain CDR1

<400> SEQUENCE: 163

Lys Ser Ser Gln Ser Leu Leu Asn Ser Gly Asn Gln Lys Asn Tyr Leu
1               5                   10                  15

Ala

<210> SEQ ID NO 164
<211> LENGTH: 7
<212> TYPE: PRT
<213> ORGANISM: Artificial Sequence
<220> FEATURE:
<223> OTHER INFORMATION: OD225 Light chain CDR2

<400> SEQUENCE: 164

Gly Ala Ser Thr Arg Glu Ser
1 5

<210> SEQ ID NO 165
<211> LENGTH: 9
<212> TYPE: PRT
<213> ORGANISM: Artificial Sequence
<220> FEATURE:
<223> OTHER INFORMATION: OD225 Light chain CDR3

<400> SEQUENCE: 165

Gln Asn Asp His Ser Tyr Pro Phe Thr
1 5

<210> SEQ ID NO 166
<211> LENGTH: 10
<212> TYPE: PRT
<213> ORGANISM: Artificial Sequence
<220> FEATURE:
<223> OTHER INFORMATION: OD225 Heavy chain CDR1

<400> SEQUENCE: 166

Gly Tyr Thr Phe Thr Ser Tyr Trp Met His
1 5 10

<210> SEQ ID NO 167
<211> LENGTH: 17
<212> TYPE: PRT
<213> ORGANISM: Artificial Sequence
<220> FEATURE:
<223> OTHER INFORMATION: OD225 Heavy chain CDR2

<400> SEQUENCE: 167

Asp Ile Tyr Pro Gly Ser Asp Ser Thr Asn Tyr Asn Glu Lys Phe Lys
1 5 10 15

Ser

<210> SEQ ID NO 168
<211> LENGTH: 9
<212> TYPE: PRT
<213> ORGANISM: Artificial Sequence
<220> FEATURE:
<223> OTHER INFORMATION: OD225 Heavy chain CDR3

<400> SEQUENCE: 168

Cys Asp Phe Tyr Trp Tyr Phe Asp Val
1 5

<210> SEQ ID NO 169
<211> LENGTH: 15
<212> TYPE: PRT
<213> ORGANISM: Artificial Sequence
<220> FEATURE:
<223> OTHER INFORMATION: OD234 Light chain CDR1

<400> SEQUENCE: 169

Arg Ala Ser Lys Ser Val Ser Thr Ser Gly Tyr Ser Tyr Met His
1 5 10 15

<210> SEQ ID NO 170
<211> LENGTH: 7
<212> TYPE: PRT
<213> ORGANISM: Artificial Sequence
<220> FEATURE:
<223> OTHER INFORMATION: OD234 Light chain CDR2

<400> SEQUENCE: 170

Leu Val Ser Asn Leu Glu Ser
1 5

<210> SEQ ID NO 171
<211> LENGTH: 9
<212> TYPE: PRT
<213> ORGANISM: Artificial Sequence
<220> FEATURE:
<223> OTHER INFORMATION: OD234 Light chain CDR3

<400> SEQUENCE: 171

Gln His Ile Arg Glu Leu Thr Arg Ser
1 5

<210> SEQ ID NO 172
<211> LENGTH: 10
<212> TYPE: PRT
<213> ORGANISM: Artificial Sequence
<220> FEATURE:
<223> OTHER INFORMATION: OD234 Heavy chain CDR1

<400> SEQUENCE: 172

Gly Tyr Ser Phe Thr Gly Tyr Thr Met Asn
1 5 10

<210> SEQ ID NO 173
<211> LENGTH: 17
<212> TYPE: PRT
<213> ORGANISM: Artificial Sequence
<220> FEATURE:
<223> OTHER INFORMATION: OD234 Heavy chain CDR2

<400> SEQUENCE: 173

Leu Ile Asn Pro Tyr Asn Gly Gly Thr Ser Tyr Asn Gln Lys Phe Lys
1 5 10 15

Gly

<210> SEQ ID NO 174
<211> LENGTH: 17
<212> TYPE: PRT
<213> ORGANISM: Artificial Sequence
<220> FEATURE:
<223> OTHER INFORMATION: OD234 Heavy chain CDR3

<400> SEQUENCE: 174

Val Arg Ala Tyr Tyr Gly Asn Tyr Glu Leu Phe Tyr Trp Tyr Phe Asp
1 5 10 15

Val

<210> SEQ ID NO 175
<211> LENGTH: 11
<212> TYPE: PRT
<213> ORGANISM: Artificial Sequence
<220> FEATURE:
<223> OTHER INFORMATION: OD241 Light chain CDR1

<400> SEQUENCE: 175

Ile Thr Ser Thr Asp Ile Asp Asp Asp Met Asn
1 5 10

<210> SEQ ID NO 176
<211> LENGTH: 7
<212> TYPE: PRT
<213> ORGANISM: Artificial Sequence
<220> FEATURE:
<223> OTHER INFORMATION: OD241 Light chain CDR2

<400> SEQUENCE: 176

Glu Gly Asn Thr Leu Arg Pro
1 5

<210> SEQ ID NO 177
<211> LENGTH: 9
<212> TYPE: PRT
<213> ORGANISM: Artificial Sequence
<220> FEATURE:
<223> OTHER INFORMATION: OD241 Light chain CDR3

<400> SEQUENCE: 177

Leu Gln Ser Asp Asn Met Pro Phe Thr
1 5

<210> SEQ ID NO 178
<211> LENGTH: 12
<212> TYPE: PRT
<213> ORGANISM: Artificial Sequence
<220> FEATURE:
<223> OTHER INFORMATION: OD241 Heavy chain CDR1

<400> SEQUENCE: 178

Gly Phe Ser Leu Ser Thr Ser Gly Met Ser Val Gly
1 5 10

<210> SEQ ID NO 179
<211> LENGTH: 16
<212> TYPE: PRT
<213> ORGANISM: Artificial Sequence
<220> FEATURE:
<223> OTHER INFORMATION: OD241 Heavy chain CDR2

<400> SEQUENCE: 179

His Ile Trp Trp Asn Asp Asp Lys Tyr Tyr Asn Pro Ala Leu Lys Ser
1 5 10 15

<210> SEQ ID NO 180
<211> LENGTH: 11
<212> TYPE: PRT
<213> ORGANISM: Artificial Sequence
<220> FEATURE:
<223> OTHER INFORMATION: OD241 Heavy chain CDR3

<400> SEQUENCE: 180

Ile Ala Arg Glu Val Arg Arg Tyr Phe Asp Val
1 5 10

<210> SEQ ID NO 181
<211> LENGTH: 10
<212> TYPE: PRT
<213> ORGANISM: Artificial Sequence
<220> FEATURE:
<223> OTHER INFORMATION: OD244 Light chain CDR1

<400> SEQUENCE: 181

```
Ser Ala Ser Ser Ser Val Ser Tyr Met Tyr
1               5                   10


<210> SEQ ID NO 182
<211> LENGTH: 7
<212> TYPE: PRT
<213> ORGANISM: Artificial Sequence
<220> FEATURE:
<223> OTHER INFORMATION: OD244 Light chain CDR2

<400> SEQUENCE: 182

Arg Thr Ser Asn Leu Ala Ser
1               5


<210> SEQ ID NO 183
<211> LENGTH: 10
<212> TYPE: PRT
<213> ORGANISM: Artificial Sequence
<220> FEATURE:
<223> OTHER INFORMATION: OD244 Light chain CDR3

<400> SEQUENCE: 183

Gln Gln Tyr His Ser Tyr Pro Met Tyr Thr
1               5                   10


<210> SEQ ID NO 184
<211> LENGTH: 10
<212> TYPE: PRT
<213> ORGANISM: Artificial Sequence
<220> FEATURE:
<223> OTHER INFORMATION: OD244 Heavy chain CDR1

<400> SEQUENCE: 184

Gly Tyr Thr Phe Thr Ser Tyr Trp Met His
1               5                   10


<210> SEQ ID NO 185
<211> LENGTH: 19
<212> TYPE: PRT
<213> ORGANISM: Artificial Sequence
<220> FEATURE:
<223> OTHER INFORMATION: OD244 Heavy chain CDR2

<400> SEQUENCE: 185

Ala Ile Tyr Pro Gly Asn Ser Asp Thr Ser Tyr Asn Gln Lys Phe Lys
1               5                   10                  15

Gly Lys Ala


<210> SEQ ID NO 186
<211> LENGTH: 10
<212> TYPE: PRT
<213> ORGANISM: Artificial Sequence
<220> FEATURE:
<223> OTHER INFORMATION: OD244 Heavy chain CDR3

<400> SEQUENCE: 186

Ser Gly Pro Pro Tyr Trp Tyr Phe Asp Val
1               5                   10


<210> SEQ ID NO 187
<211> LENGTH: 11
<212> TYPE: PRT
<213> ORGANISM: Artificial Sequence
<220> FEATURE:
<223> OTHER INFORMATION: OD270 Light chain CDR1

<400> SEQUENCE: 187
```

Lys Ala Ser Gln Asp Ile Asn Lys Tyr Ile Ala
1 5 10

<210> SEQ ID NO 188
<211> LENGTH: 7
<212> TYPE: PRT
<213> ORGANISM: Artificial Sequence
<220> FEATURE:
<223> OTHER INFORMATION: OD270 Light chain CDR2

<400> SEQUENCE: 188

Tyr Thr Ser Thr Leu Gln Pro
1 5

<210> SEQ ID NO 189
<211> LENGTH: 8
<212> TYPE: PRT
<213> ORGANISM: Artificial Sequence
<220> FEATURE:
<223> OTHER INFORMATION: OD270 Light chain CDR3

<400> SEQUENCE: 189

Leu Gln Tyr Asp Asn Leu Trp Thr
1 5

<210> SEQ ID NO 190
<211> LENGTH: 10
<212> TYPE: PRT
<213> ORGANISM: Artificial Sequence
<220> FEATURE:
<223> OTHER INFORMATION: OD270 Heavy chain CDR1

<400> SEQUENCE: 190

Gly Tyr Ser Phe Thr Ser Tyr Trp Met Asn
1 5 10

<210> SEQ ID NO 191
<211> LENGTH: 17
<212> TYPE: PRT
<213> ORGANISM: Artificial Sequence
<220> FEATURE:
<223> OTHER INFORMATION: OD270 Heavy chain CDR2

<400> SEQUENCE: 191

Met Ile His Pro Ser Asp Ser Glu Thr Arg Leu Asn Gln Lys Phe Lys
1 5 10 15

Asp

<210> SEQ ID NO 192
<211> LENGTH: 6
<212> TYPE: PRT
<213> ORGANISM: Artificial Sequence
<220> FEATURE:
<223> OTHER INFORMATION: OD270 Heavy chain CDR3

<400> SEQUENCE: 192

Gly Tyr Ala Met Asp Tyr
1 5

<210> SEQ ID NO 193
<211> LENGTH: 17
<212> TYPE: PRT
<213> ORGANISM: Artificial Sequence
<220> FEATURE:
<223> OTHER INFORMATION: OD296 Light chain CDR1

<400> SEQUENCE: 193

Lys Ser Ser Gln Ser Leu Leu Trp Ser Val Asn Gln Asn Asn Tyr Leu
1 5 10 15

Ser

<210> SEQ ID NO 194
<211> LENGTH: 7
<212> TYPE: PRT
<213> ORGANISM: Artificial Sequence
<220> FEATURE:
<223> OTHER INFORMATION: OD296 Light chain CDR2

<400> SEQUENCE: 194

Gly Ala Ser Ile Arg Glu Ser
1 5

<210> SEQ ID NO 195
<211> LENGTH: 11
<212> TYPE: PRT
<213> ORGANISM: Artificial Sequence
<220> FEATURE:
<223> OTHER INFORMATION: OD296 Light chain CDR3

<400> SEQUENCE: 195

Gln His Asn His Gly Ser Phe Leu Pro Leu Thr
1 5 10

<210> SEQ ID NO 196
<211> LENGTH: 10
<212> TYPE: PRT
<213> ORGANISM: Artificial Sequence
<220> FEATURE:
<223> OTHER INFORMATION: OD296 Heavy chain CDR1

<400> SEQUENCE: 196

Gly Tyr Thr Phe Thr Ser Tyr Val Met His
1 5 10

<210> SEQ ID NO 197
<211> LENGTH: 17
<212> TYPE: PRT
<213> ORGANISM: Artificial Sequence
<220> FEATURE:
<223> OTHER INFORMATION: OD296 Heavy chain CDR2

<400> SEQUENCE: 197

Tyr Ile Asn Pro Tyr Asn Asp Gly Thr Lys Tyr Asn Glu Lys Phe Lys
1 5 10 15

Gly

<210> SEQ ID NO 198
<211> LENGTH: 13
<212> TYPE: PRT
<213> ORGANISM: Artificial Sequence
<220> FEATURE:
<223> OTHER INFORMATION: OD296 Heavy chain CDR3

<400> SEQUENCE: 198

Arg Glu Lys Tyr Gly Asn Tyr Val Gly Ala Met Asp Tyr
1 5 10

<210> SEQ ID NO 199
<211> LENGTH: 11
<212> TYPE: PRT
<213> ORGANISM: Artificial Sequence
<220> FEATURE:
<223> OTHER INFORMATION: OD298 Light chain CDR1

<400> SEQUENCE: 199

Arg Ala Ser Gln Ser Ile Gly Thr Ser Ile His
1               5                   10

<210> SEQ ID NO 200
<211> LENGTH: 7
<212> TYPE: PRT
<213> ORGANISM: Artificial Sequence
<220> FEATURE:
<223> OTHER INFORMATION: OD298 Light chain CDR2

<400> SEQUENCE: 200

Tyr Ala Ser Glu Ser Ile Ser
1               5

<210> SEQ ID NO 201
<211> LENGTH: 9
<212> TYPE: PRT
<213> ORGANISM: Artificial Sequence
<220> FEATURE:
<223> OTHER INFORMATION: OD298 Light chain CDR3

<400> SEQUENCE: 201

Gln Gln Ser Asn Ser Trp Pro Tyr Thr
1               5

<210> SEQ ID NO 202
<211> LENGTH: 10
<212> TYPE: PRT
<213> ORGANISM: Artificial Sequence
<220> FEATURE:
<223> OTHER INFORMATION: OD298 Heavy chain CDR1

<400> SEQUENCE: 202

Gly Tyr Thr Phe Thr Asp Tyr Ala Met His
1               5                   10

<210> SEQ ID NO 203
<211> LENGTH: 17
<212> TYPE: PRT
<213> ORGANISM: Artificial Sequence
<220> FEATURE:
<223> OTHER INFORMATION: OD298 Heavy chain CDR2

<400> SEQUENCE: 203

Val Ile Ser Thr Tyr Ser Gly Asn Thr Asn Tyr Asn Gln Lys Phe Lys
1               5                   10                  15

Gly

<210> SEQ ID NO 204
<211> LENGTH: 10
<212> TYPE: PRT
<213> ORGANISM: Artificial Sequence
<220> FEATURE:
<223> OTHER INFORMATION: OD298 Heavy chain CDR3

<400> SEQUENCE: 204

Glu Ala Ser Gly Leu Cys Pro Phe Asp Tyr
1               5                   10

<210> SEQ ID NO 205
<211> LENGTH: 11
<212> TYPE: PRT

<213> ORGANISM: Artificial Sequence
<220> FEATURE:
<223> OTHER INFORMATION: OD340 Light chain CDR1

<400> SEQUENCE: 205

Arg Ala Ser Gly Asn Ile His Asn Tyr Leu Ala
1 5 10

<210> SEQ ID NO 206
<211> LENGTH: 7
<212> TYPE: PRT
<213> ORGANISM: Artificial Sequence
<220> FEATURE:
<223> OTHER INFORMATION: OD340 Light chain CDR2

<400> SEQUENCE: 206

Asn Ala Lys Thr Leu Ala Asp
1 5

<210> SEQ ID NO 207
<211> LENGTH: 9
<212> TYPE: PRT
<213> ORGANISM: Artificial Sequence
<220> FEATURE:
<223> OTHER INFORMATION: OD340 Light chain CDR3

<400> SEQUENCE: 207

Gln His Phe Trp Ser Thr Pro Leu Thr
1 5

<210> SEQ ID NO 208
<211> LENGTH: 10
<212> TYPE: PRT
<213> ORGANISM: Artificial Sequence
<220> FEATURE:
<223> OTHER INFORMATION: OD340 Heavy chain CDR1

<400> SEQUENCE: 208

Gly Tyr Thr Phe Thr Asp Tyr Asn Met His
1 5 10

<210> SEQ ID NO 209
<211> LENGTH: 17
<212> TYPE: PRT
<213> ORGANISM: Artificial Sequence
<220> FEATURE:
<223> OTHER INFORMATION: OD340 Heavy chain CDR2

<400> SEQUENCE: 209

Tyr Ile Tyr Pro Tyr Asn Gly Gly Thr Gly Tyr Asn Gln Lys Phe Lys
1 5 10 15

Ser

<210> SEQ ID NO 210
<211> LENGTH: 11
<212> TYPE: PRT
<213> ORGANISM: Artificial Sequence
<220> FEATURE:
<223> OTHER INFORMATION: OD340 Heavy chain CDR3

<400> SEQUENCE: 210

Ala Asp Gly Asn His Pro Tyr Tyr Phe Asp Tyr
1 5 10

<210> SEQ ID NO 211
<211> LENGTH: 107

<212> TYPE: PRT
<213> ORGANISM: Artificial Sequence
<220> FEATURE:
<223> OTHER INFORMATION: OD7 Light chain

<400> SEQUENCE: 211

Phe Arg Lys Leu Asp Ile Gln Leu Thr Gln Ser Pro Ala Thr Leu Ser
1               5                   10                  15

Val Thr Pro Gly Asp Ser Val Ser Leu Ser Cys Arg Ala Ser Gln Ser
            20                  25                  30

Ile Ser Asn Asn Leu His Trp Tyr Gln Gln Lys Ser His Glu Ser Pro
        35                  40                  45

Arg Leu Leu Ile Lys Tyr Ala Ser Gln Ser Ile Ser Gly Ile Pro Ser
    50                  55                  60

Arg Phe Ser Gly Ser Gly Ser Gly Thr Asp Phe Thr Leu Ser Ile Asn
65                  70                  75                  80

Ser Val Glu Thr Glu Asp Phe Gly Met Tyr Phe Cys Gln Gln Ser Asn
                85                  90                  95

Ser Trp Pro Leu Thr Phe Gly Ala Gly Pro Ser
            100                 105

<210> SEQ ID NO 212
<211> LENGTH: 120
<212> TYPE: PRT
<213> ORGANISM: Artificial Sequence
<220> FEATURE:
<223> OTHER INFORMATION: OD7 Heavy chain

<400> SEQUENCE: 212

Phe Arg Lys Phe Glu Val Gln Leu Gln Gln Ser Gly Ala Glu Leu Val
1               5                   10                  15

Arg Pro Gly Ala Ser Val Lys Leu Ser Cys Lys Ala Ser Gly Tyr Ser
            20                  25                  30

Phe Thr Ser Tyr Trp Met Asn Trp Val Lys Gln Arg Pro Gly Gln Gly
        35                  40                  45

Leu Glu Trp Ile Gly Met Ile His Pro Ser Asp Ser Glu Thr Arg Leu
    50                  55                  60

Asn Gln Lys Phe Lys Asp Lys Ala Thr Leu Thr Val Asp Lys Ser Ser
65                  70                  75                  80

Ser Thr Ala Tyr Met Gln Leu Ser Ser Pro Thr Ser Glu Asp Ser Ala
                85                  90                  95

Val Tyr Tyr Cys Ala Arg Pro Val Val Ala Thr Gly Arg Tyr Tyr Ser
            100                 105                 110

Met Asp Tyr Trp Gly Gln Gly Thr
        115                 120

<210> SEQ ID NO 213
<211> LENGTH: 116
<212> TYPE: PRT
<213> ORGANISM: Artificial Sequence
<220> FEATURE:
<223> OTHER INFORMATION: OD111A Light chain

<400> SEQUENCE: 213

Asp Ile Gln Leu Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val

```
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ala Gly Thr Lys Leu Glu Leu Lys Arg Ala Asp Ala Ala
            100                 105                 110

Pro Thr Val Ser
        115
```

<210> SEQ ID NO 214
<211> LENGTH: 126
<212> TYPE: PRT
<213> ORGANISM: Artificial Sequence
<220> FEATURE:
<223> OTHER INFORMATION: OD111A Heavy chain

<400> SEQUENCE: 214

```
Leu Pro Glu Phe Gln Val Gln Leu Gln Gln Ser Gly Ala Glu Leu Met
1               5                   10                  15

Lys Pro Gly Ala Ser Val Lys Ile Ser Cys Lys Ala Thr Gly Tyr Thr
            20                  25                  30

Phe Ser Ser Tyr Trp Ile Glu Trp Val Lys Gln Arg Pro Gly His Gly
        35                  40                  45

Leu Glu Trp Ile Gly Glu Ile Leu Pro Gly Ser Gly Ser Thr Asn Tyr
    50                  55                  60

Asn Glu Lys Phe Lys Gly Lys Ala Thr Phe Thr Ala Asp Thr Ser Ser
65                  70                  75                  80

Asn Thr Ala Tyr Met Gln Leu Ser Ser Leu Thr Ser Glu Asp Ser Ala
                85                  90                  95

Val Tyr Tyr Cys Ala Arg Arg Lys Trp Gly Asn Tyr Val Asn Tyr Tyr
            100                 105                 110

Ala Met Asp Tyr Trp Gly Gln Gly Thr Ser Val Thr Val Leu
        115                 120                 125
```

<210> SEQ ID NO 215
<211> LENGTH: 102
<212> TYPE: PRT
<213> ORGANISM: Artificial Sequence
<220> FEATURE:
<223> OTHER INFORMATION: OD169B Light chain

<400> SEQUENCE: 215

```
Met Gln Leu Thr Gln Ser Pro Ala Ile Met Ser Ala Ser Pro Gly Glu
1               5                   10                  15

Lys Val Thr Met Thr Cys Ser Ala Ser Ser Ser Val Ser Tyr Met His
            20                  25                  30

Trp Tyr Gln Gln Lys Ser Gly Thr Ser Pro Lys Arg Trp Ile Tyr Asp
        35                  40                  45

Thr Ser Lys Leu Ala Ser Gly Val Pro Ala Arg Phe Ser Gly Ser Gly
    50                  55                  60

Ser Gly Thr Ser Tyr Ser Leu Thr Ile Ser Ser Met Glu Ala Glu Asp
65                  70                  75                  80

Ala Ala Thr Tyr Tyr Cys Gln Gln Trp Ser Ser Asn Pro Pro Thr Phe
                85                  90                  95
```

Gly Ser Gly Gln Ser Glu
            100

<210> SEQ ID NO 216
<211> LENGTH: 115
<212> TYPE: PRT
<213> ORGANISM: Artificial Sequence
<220> FEATURE:
<223> OTHER INFORMATION: OD169B Heavy chain

<400> SEQUENCE: 216

Leu Pro Glu Phe Glu Val Gln Leu Glu Glu Ser Gly Pro Gly Leu Val
1               5                   10                  15

Ala Pro Ser Gln Ser Leu Ser Ile Thr Cys Thr Val Ser Gly Phe Ser
            20                  25                  30

Leu Thr Ser Tyr Gly Val Ser Trp Val Arg Gln Pro Pro Gly Lys Gly
        35                  40                  45

Leu Glu Trp Leu Gly Val Ile Trp Gly Asp Gly Ser Thr Asn Tyr His
    50                  55                  60

Ser Ala Leu Ile Ser Arg Leu Ser Ile Ser Lys Asp Asn Ser Lys Ser
65                  70                  75                  80

Gln Val Phe Leu Lys Leu Asn Ser Leu Gln Thr Asp Asp Thr Ala Thr
                85                  90                  95

Tyr Tyr Cys Ala Gly Tyr Arg Gly Tyr Trp Gly Gln Gly Thr Leu Val
            100                 105                 110

Thr Thr Pro
        115

<210> SEQ ID NO 217
<211> LENGTH: 121
<212> TYPE: PRT
<213> ORGANISM: Artificial Sequence
<220> FEATURE:
<223> OTHER INFORMATION: OD184 Light chain

<400> SEQUENCE: 217

Asp Ile Gln Leu Thr Gln Ser Pro Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
            100                 105                 110

Arg Ala Asp Ala Ala Pro Thr Val Ser
        115                 120

<210> SEQ ID NO 218
<211> LENGTH: 125
<212> TYPE: PRT
<213> ORGANISM: Artificial Sequence
<220> FEATURE:
<223> OTHER INFORMATION: OD184 Heavy chain

<400> SEQUENCE: 218

Leu Pro Glu Phe Gln Val Gln Leu Gln Gln Ser Gly Ser Glu Leu Arg
1 5 10 15

Ser Pro Gly Ser Ser Val Lys Leu Ser Cys Lys Asp Phe Asp Ser Glu
20 25 30

Val Phe Pro Ile Ala Tyr Met Ser Trp Val Arg Gln Lys Pro Gly His
35 40 45

Gly Phe Glu Trp Ile Gly Asp Ile Leu Pro Ser Ile Gly Arg Thr Ile
50 55 60

Tyr Gly Glu Lys Phe Glu Asp Lys Ala Thr Leu Asp Ala Asp Thr Val
65 70 75 80

Ser Asn Thr Ala Tyr Leu Glu Leu Asn Ser Leu Thr Ser Glu Asp Ser
85 90 95

Ala Ile Tyr Tyr Cys Ala Arg Glu Gly Ser Ser Gly Tyr Gly Ala Trp
100 105 110

Phe Ala Tyr Trp Gly Gln Gly Thr Leu Val Thr Leu Cys
115 120 125

<210> SEQ ID NO 219
<211> LENGTH: 112
<212> TYPE: PRT
<213> ORGANISM: Artificial Sequence
<220> FEATURE:
<223> OTHER INFORMATION: OD185 Light chain

<400> SEQUENCE: 219

Arg Lys Leu Asp Ile Gln Leu Thr Gln Ser Pro Ser Ser Leu Ser Val
1 5 10 15

Ser Ala Gly Glu Lys Val Thr Met Ser Cys Lys Ser Ser Gln Ser Leu
20 25 30

Leu Asn Ser Gly Asn Gln Lys Asn Tyr Leu Ala Trp Tyr Gln Gln Lys
35 40 45

Pro Gly Gln Pro Pro Lys Leu Leu Ile Tyr Gly Ala Ser Thr Arg Glu
50 55 60

Ser Gly Val Pro Asp Arg Phe Thr Gly Ser Gly Ser Gly Thr Asp Phe
65 70 75 80

Thr Leu Thr Ile Ser Ser Val Gln Ala Glu Asp Leu Ala Val Tyr Tyr
85 90 95

Cys Gln Asn Asp His Ser Tyr Pro Tyr Thr Phe Gly Gly Gly Pro Ser
100 105 110

<210> SEQ ID NO 220
<211> LENGTH: 125
<212> TYPE: PRT
<213> ORGANISM: Artificial Sequence
<220> FEATURE:
<223> OTHER INFORMATION: OD185 Heavy chain

<400> SEQUENCE: 220

Leu Pro Glu Phe Gln Val Gln Leu Glu Gln Ser Gly Pro Gly Ile Leu
1 5 10 15

Gln Pro Ser Gln Thr Leu Ser Leu Thr Cys Ser Phe Ser Gly Phe Ser
20 25 30

Leu Ser Thr Ser Gly Met Gly Val Gly Trp Ile Arg Gln Pro Ser Gly
35 40 45

Lys Gly Leu Glu Trp Leu Ala His Ile Trp Trp Asp Asp Asp Lys Arg
50 55 60

Tyr Asn Pro Ala Leu Lys Ser Arg Leu Thr Ile Ser Lys Asp Thr Ser
65 70 75 80

Ser Asn Gln Val Phe Leu Lys Ile Ala Ser Val Asp Thr Ala Asp Thr
85 90 95

Ala Thr Tyr Tyr Cys Ala Arg Ile Glu Asp Ser Leu Leu Pro Leu Gly
100 105 110

Phe Ala Tyr Trp Gly Gln Gly Thr Leu Val Thr Thr Leu
115 120 125

<210> SEQ ID NO 221
<211> LENGTH: 107
<212> TYPE: PRT
<213> ORGANISM: Artificial Sequence
<220> FEATURE:
<223> OTHER INFORMATION: OD196 Light chain

<400> SEQUENCE: 221

Cys Arg Lys Leu Asp Ile Gln Leu Thr Gln Ser Pro Lys Phe Met Ser
1 5 10 15

Thr Ser Val Gly Asp Arg Val Ser Val Thr Cys Lys Ala Ser Gln Asn
20 25 30

Val Gly Thr Asn Val Ala Trp Tyr Gln Gln Lys Pro Gly Gln Ser Pro
35 40 45

Lys Ala Leu Ile Tyr Ser Ala Ser Tyr Arg Tyr Ser Gly Val Pro Asp
50 55 60

Arg Phe Thr Gly Ser Gly Ser Gly Thr Asp Phe Thr Leu Thr Ile Ser
65 70 75 80

Asn Val Gln Ser Glu Asp Leu Ala Glu Tyr Phe Cys Gln Gln Tyr Asn
85 90 95

Ser Tyr Pro Tyr Thr Phe Gly Gly Gly Pro Ser
100 105

<210> SEQ ID NO 222
<211> LENGTH: 118
<212> TYPE: PRT
<213> ORGANISM: Artificial Sequence
<220> FEATURE:
<223> OTHER INFORMATION: OD196 Heavy chain

<400> SEQUENCE: 222

Leu Pro Glu Phe Glu Val Gln Leu Gln Glu Ser Gly Pro Glu Leu Val
1 5 10 15

Lys Pro Gly Ala Ser Val Lys Ile Ser Cys Lys Thr Ser Gly Tyr Thr
20 25 30

Phe Thr Glu Tyr Thr Met His Trp Val Lys Gln Ser His Gly Lys Ser
35 40 45

Leu Glu Trp Ile Gly Gly Ile Asn Pro Asn Asn Gly Gly Thr Ser Tyr
50 55 60

Asn Gln Lys Phe Lys Gly Lys Ala Thr Leu Thr Val Asp Lys Ser Ser
65 70 75 80

Ser Thr Ala Tyr Met Glu Leu Arg Ser Leu Thr Ser Glu Asp Ser Ala
85 90 95

Val Tyr Tyr Cys Ala Thr Gly Tyr Ala Met Asp Tyr Trp Gly Gln Gly
100 105 110

Thr Ser Val Thr Phe Ser
115

<210> SEQ ID NO 223

<211> LENGTH: 114
<212> TYPE: PRT
<213> ORGANISM: Artificial Sequence
<220> FEATURE:
<223> OTHER INFORMATION: OD210A Light chain

<400> SEQUENCE: 223

```
Lys Leu Asp Ile Val Leu Thr Gln Ser Pro Ala Ser Leu Ala Val Ser
1               5                   10                  15

Leu Gly Gln Arg Ala Thr Ile Ser Cys Arg Ala Ser Glu Ser Val Asp
            20                  25                  30

Asn Tyr Gly Ile Ser Phe Met Asn Trp Phe Gln Gln Lys Pro Gly Gln
        35                  40                  45

Pro Pro Lys Leu Leu Ile Tyr Ala Ala Ser Asn Gln Gly Ser Gly Val
    50                  55                  60

Pro Ala Arg Phe Ser Gly Ser Gly Ser Gly Thr Asp Phe Ser Leu Asn
65                  70                  75                  80

Ile His Pro Met Glu Glu Asp Asp Thr Ala Met Tyr Phe Cys Gln Gln
                85                  90                  95

Ser Lys Glu Val Pro Arg Thr Phe Gly Gly Gly Thr Lys Leu Asn Gln
            100                 105                 110

Ser Gly
```

<210> SEQ ID NO 224
<211> LENGTH: 124
<212> TYPE: PRT
<213> ORGANISM: Artificial Sequence
<220> FEATURE:
<223> OTHER INFORMATION: OD210A Heavy chain

<400> SEQUENCE: 224

```
Phe Arg Lys Phe Gln Val Gln Leu Gln Gln Ser Gly Gly Gly Leu Val
1               5                   10                  15

Gln Pro Gly Gly Ser Leu Lys Leu Ser Cys Ala Ala Ser Gly Phe Asp
            20                  25                  30

Phe Ser Arg Tyr Trp Met Ser Trp Val Arg Gln Ala Pro Gly Lys Gly
        35                  40                  45

Leu Glu Trp Ile Gly Glu Ile Asn Pro Asp Ser Ser Thr Ile Asn Tyr
    50                  55                  60

Thr Pro Ser Leu Lys Asp Lys Phe Ile Ile Ser Arg Asp Asn Ala Lys
65                  70                  75                  80

Asn Thr Leu Tyr Leu Gln Met Ser Lys Val Arg Ser Glu Asp Thr Ala
                85                  90                  95

Leu Tyr Tyr Cys Ala Arg Arg Gly Ile Tyr Tyr Gly Asn Tyr Cys Asp
            100                 105                 110

Tyr Trp Gly Gln Gly Thr Thr Leu Thr Val Pro Cys
        115                 120
```

<210> SEQ ID NO 225
<211> LENGTH: 112
<212> TYPE: PRT
<213> ORGANISM: Artificial Sequence
<220> FEATURE:
<223> OTHER INFORMATION: OD225 Light chain

<400> SEQUENCE: 225

```
Lys Leu Asp Ile Gln Leu Thr Gln Ser Pro Ser Ser Leu Ser Val Ser
1               5                   10                  15

Ala Gly Glu Lys Val Thr Met Ser Cys Lys Ser Ser Gln Ser Leu Leu
```

```
            20                  25                  30

Asn Ser Gly Asn Gln Lys Asn Tyr Leu Ala Trp Tyr Gln Gln Lys Pro
        35                  40                  45

Gly Gln Pro Pro Lys Leu Leu Ile Tyr Gly Ala Ser Thr Arg Glu Ser
    50                  55                  60

Gly Val Pro Asp Arg Phe Thr Gly Ser Gly Ser Gly Thr Asp Phe Thr
65                  70                  75                  80

Leu Thr Ile Ser Ser Val Gln Ala Glu Asp Leu Ala Val Tyr Tyr Cys
                85                  90                  95

Gln Asn Asp His Ser Tyr Pro Phe Thr Phe Gly Ser Gly Gln Ser Glu
            100                 105                 110


<210> SEQ ID NO 226
<211> LENGTH: 121
<212> TYPE: PRT
<213> ORGANISM: Artificial Sequence
<220> FEATURE:
<223> OTHER INFORMATION: OD225 Heavy chain

<400> SEQUENCE: 226

Leu Pro Glu Phe Gln Val Gln Leu Gln Gln Ser Gly Ala Glu Leu Val
1               5                   10                  15

Lys Pro Gly Thr Ser Val Lys Met Ser Cys Lys Ala Ser Gly Tyr Thr
            20                  25                  30

Phe Thr Ser Tyr Trp Met His Trp Val Lys Gln Arg Pro Gly Gln Gly
        35                  40                  45

Leu Glu Trp Ile Gly Asp Ile Tyr Pro Gly Ser Asp Ser Thr Asn Tyr
    50                  55                  60

Asn Glu Lys Phe Lys Ser Lys Ala Thr Leu Thr Val Asp Thr Ser Ser
65                  70                  75                  80

Ser Thr Ala Tyr Met Gln Leu Ser Ser Leu Thr Ser Glu Asp Ser Ala
                85                  90                  95

Val Tyr Tyr Cys Ala Arg Cys Asp Phe Tyr Trp Tyr Phe Asp Val Trp
            100                 105                 110

Gly Ala Gly Pro Arg Ser Pro Ser Leu
        115                 120


<210> SEQ ID NO 227
<211> LENGTH: 108
<212> TYPE: PRT
<213> ORGANISM: Artificial Sequence
<220> FEATURE:
<223> OTHER INFORMATION: OD234  Light chain

<400> SEQUENCE: 227

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95
```

```
Glu Leu Thr Arg Ser Glu Gly Gly Pro Ser Trp Lys
            100                 105


<210> SEQ ID NO 228
<211> LENGTH: 127
<212> TYPE: PRT
<213> ORGANISM: Artificial Sequence
<220> FEATURE:
<223> OTHER INFORMATION: OD234 Heavy chain

<400> SEQUENCE: 228

Leu Ser Glu Phe Glu Val Gln Leu Gln Gln Ser Gly Pro Glu Leu Val
1               5                   10                  15

Lys Pro Gly Ala Ser Met Lys Ile Ser Cys Lys Ala Ser Gly Tyr Ser
            20                  25                  30

Phe Thr Gly Tyr Thr Met Asn Trp Val Ser His Gly Lys Asn Leu Glu
        35                  40                  45

Trp Ile Gly Leu Ile Asn Pro Tyr Asn Gly Gly Thr Ser Tyr Asn Gln
    50                  55                  60

Lys Phe Lys Gly Lys Ala Thr Leu Thr Val Asp Lys Ser Ser Ser Thr
65                  70                  75                  80

Ala Tyr Met Glu Leu Leu Ser Leu Thr Ser Glu Asp Ser Ala Val Tyr
                85                  90                  95

Tyr Cys Ala Arg Val Arg Ala Tyr Tyr Gly Asn Tyr Glu Leu Phe Tyr
            100                 105                 110

Trp Tyr Phe Asp Val Trp Gly Ala Gly Pro Arg Ser Pro Ser Pro
        115                 120                 125


<210> SEQ ID NO 229
<211> LENGTH: 116
<212> TYPE: PRT
<213> ORGANISM: Artificial Sequence
<220> FEATURE:
<223> OTHER INFORMATION: OD241 Light chain

<400> SEQUENCE: 229

Asp Ile Gln Leu Thr Gln Ser Pro Ala Ser Leu Ser Val Ala Thr Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Thr Leu Ser
65                  70                  75                  80

Glu Asp Val Ala Asp Tyr Tyr Cys Leu Gln Ser Asp Asn Met Pro Phe
                85                  90                  95

Thr Phe Gly Ser Gly Thr Lys Leu Glu Ile Arg Arg Ala Asp Ala Ala
            100                 105                 110

Pro Thr Val Ser
        115


<210> SEQ ID NO 230
<211> LENGTH: 124
<212> TYPE: PRT
<213> ORGANISM: Artificial Sequence
<220> FEATURE:
<223> OTHER INFORMATION: OD241 Heavy chain
```

<400> SEQUENCE: 230

Phe Arg Lys Phe Gln Val Gln Leu Gln Glu Ser Gly Pro Gly Ile Leu
1 5 10 15

Gln Pro Ser Gln Thr Leu Ser Leu Thr Cys Ser Phe Ser Gly Phe Ser
20 25 30

Leu Ser Thr Ser Gly Met Ser Val Gly Trp Ile Arg Gln Pro Ser Gly
35 40 45

Lys Gly Leu Glu Trp Leu Ala His Ile Trp Trp Asn Asp Asp Lys Tyr
50 55 60

Tyr Asn Pro Ala Leu Lys Ser Arg Leu Thr Ile Ser Lys Asp Thr Ser
65 70 75 80

Asn Asn Gln Val Phe Leu Lys Ile Ala Ser Val Val Thr Ala Asp Thr
85 90 95

Ala Thr Tyr Tyr Cys Ala Arg Ile Ala Arg Glu Val Arg Arg Tyr Phe
100 105 110

Asp Val Trp Gly Ala Gly Pro Arg Ser Pro Ser Leu
115 120

<210> SEQ ID NO 231
<211> LENGTH: 107
<212> TYPE: PRT
<213> ORGANISM: Artificial Sequence
<220> FEATURE:
<223> OTHER INFORMATION: OD244 Light chain

<400> SEQUENCE: 231

Tyr Arg Lys Leu Asp Ile Gln Leu Thr Gln Ser Pro Ala Ile Met Ser
1 5 10 15

Ala Ser Pro Gly Glu Lys Val Thr Ile Ser Cys Ser Ala Ser Ser Ser
20 25 30

Val Ser Tyr Met Tyr Trp Tyr Gln Gln Lys Pro Gly Ser Ser Pro Lys
35 40 45

Pro Trp Ile Tyr Arg Thr Ser Asn Leu Ala Ser Gly Val Pro Ala Arg
50 55 60

Phe Ser Gly Ser Gly Ser Gly Thr Ser Tyr Ser Leu Thr Ile Ser Ser
65 70 75 80

Met Glu Ala Glu Asp Ala Ala Thr Tyr Tyr Cys Gln Gln Tyr His Ser
85 90 95

Tyr Pro Met Tyr Thr Phe Gly Gly Gly Pro Ser
100 105

<210> SEQ ID NO 232
<211> LENGTH: 122
<212> TYPE: PRT
<213> ORGANISM: Artificial Sequence
<220> FEATURE:
<223> OTHER INFORMATION: OD244 Heavy chain

<400> SEQUENCE: 232

Leu Pro Glu Ile Glu Val Gln Leu Gln Gln Ser Gly Thr Val Leu Ala
1 5 10 15

Arg Pro Gly Ala Ser Val Lys Met Ser Cys Lys Ala Ser Gly Tyr Thr
20 25 30

Phe Thr Ser Tyr Trp Met His Trp Val Lys Gln Arg Pro Gly Gln Gly
35 40 45

Leu Glu Trp Ile Gly Ala Ile Tyr Pro Gly Asn Ser Asp Thr Ser Tyr
50 55 60

Asn Gln Lys Phe Lys Gly Lys Ala Lys Leu Thr Ala Val Thr Ser Thr
65 70 75 80

Ser Thr Ala Tyr Met Glu Leu Ser Ser Leu Thr Asn Glu Asp Ser Ala
85 90 95

Val Tyr Tyr Cys Thr Arg Ser Gly Pro Pro Tyr Trp Tyr Phe Asp Val
100 105 110

Trp Gly Ala Gly Pro Arg Ser Pro Pro Tyr
115 120

<210> SEQ ID NO 233
<211> LENGTH: 111
<212> TYPE: PRT
<213> ORGANISM: Artificial Sequence
<220> FEATURE:
<223> OTHER INFORMATION: OD270 Light chain

<400> SEQUENCE: 233

Ser Arg Lys Leu Cys Ile Gln Leu Thr Gln Ser Pro Ser Ser Leu Ser
1 5 10 15

Ala Ser Leu Gly Gly Lys Val Thr Ile Thr Cys Lys Ala Ser Gln Asp
20 25 30

Ile Asn Lys Tyr Ile Ala Trp Tyr Gln His Lys Pro Gly Lys Gly Pro
35 40 45

Arg Leu Leu Ile His Tyr Thr Ser Thr Leu Gln Pro Gly Ile Pro Ser
50 55 60

Arg Phe Ser Gly Ser Gly Ser Gly Arg Asp Tyr Ser Phe Ser Ile Ser
65 70 75 80

Asn Leu Glu Pro Glu Asp Ile Ala Thr Tyr Tyr Cys Leu Gln Tyr Asp
85 90 95

Asn Leu Trp Thr Phe Gly Gly Gly Thr Lys Leu Asn Gln Ala Gly
100 105 110

<210> SEQ ID NO 234
<211> LENGTH: 118
<212> TYPE: PRT
<213> ORGANISM: Artificial Sequence
<220> FEATURE:
<223> OTHER INFORMATION: OD270 Heavy chain

<400> SEQUENCE: 234

Phe Arg Lys Phe Glu Val Gln Leu Gln Glu Ser Gly Ala Glu Leu Val
1 5 10 15

Arg Pro Gly Ala Ser Val Lys Leu Ser Cys Lys Ala Ser Gly Tyr Ser
20 25 30

Phe Thr Ser Tyr Trp Met Asn Trp Val Lys Gln Arg Pro Gly Gln Gly
35 40 45

Leu Glu Trp Ile Gly Met Ile His Pro Ser Asp Ser Glu Thr Arg Leu
50 55 60

Asn Gln Lys Phe Lys Asp Lys Ala Thr Leu Thr Val Asp Lys Ser Ser
65 70 75 80

Ser Thr Ala Tyr Met Gln Leu Ser Ser Pro Thr Ser Glu Asp Ser Ala
85 90 95

Val Tyr Tyr Cys Val Asp Gly Tyr Ala Met Asp Tyr Trp Gly Gln Gly
100 105 110

Thr Ser Val Thr Val Pro
115

<210> SEQ ID NO 235

```
<211> LENGTH: 114
<212> TYPE: PRT
<213> ORGANISM: Artificial Sequence
<220> FEATURE:
<223> OTHER INFORMATION: OD296 Light chain

<400> SEQUENCE: 235

Arg Lys Leu Asp Ile Gln Leu Thr Gln Ser Pro Ser Ser Leu Ala Val
1               5                   10                  15

Thr Ala Gly Glu Lys Val Thr Met Arg Cys Lys Ser Ser Gln Ser Leu
            20                  25                  30

Leu Trp Ser Val Asn Gln Asn Asn Tyr Leu Ser Trp Tyr Gln Gln Lys
        35                  40                  45

Gln Gly Gln Pro Pro Lys Leu Leu Ile Tyr Gly Ala Ser Ile Arg Glu
    50                  55                  60

Ser Trp Val Pro Asp Arg Phe Thr Gly Ser Gly Ser Gly Thr Asp Phe
65                  70                  75                  80

Thr Leu Thr Ile Ser Asn Val His Ala Glu Asp Leu Ala Val Tyr Tyr
                85                  90                  95

Cys Gln His Asn His Gly Ser Phe Leu Pro Leu Thr Phe Gly Ala Gly
            100                 105                 110

Pro Ser


<210> SEQ ID NO 236
<211> LENGTH: 125
<212> TYPE: PRT
<213> ORGANISM: Artificial Sequence
<220> FEATURE:
<223> OTHER INFORMATION: OD296 Heavy chain

<400> SEQUENCE: 236

Phe Arg Lys Phe Glu Val Gln Leu Gln Glu Ser Gly Pro Glu Leu Val
1               5                   10                  15

Lys Pro Gly Ala Ser Val Lys Met Ser Cys Lys Ala Ser Gly Tyr Thr
            20                  25                  30

Phe Thr Ser Tyr Val Met His Trp Val Lys Gln Lys Pro Gly Gln Gly
        35                  40                  45

Leu Glu Trp Ile Gly Tyr Ile Asn Pro Tyr Asn Asp Gly Thr Lys Tyr
    50                  55                  60

Asn Glu Lys Phe Lys Gly Lys Ala Thr Leu Thr Ser Asp Lys Ser Ser
65                  70                  75                  80

Ser Thr Ala Tyr Met Glu Leu Ser Ser Leu Thr Ser Glu Asp Ser Ala
                85                  90                  95

Val Tyr Tyr Cys Ala Arg Arg Glu Lys Tyr Gly Asn Tyr Val Gly Ala
            100                 105                 110

Met Asp Tyr Trp Gly Gln Gly Thr Ser Val Thr Val Leu
        115                 120                 125


<210> SEQ ID NO 237
<211> LENGTH: 107
<212> TYPE: PRT
<213> ORGANISM: Artificial Sequence
<220> FEATURE:
<223> OTHER INFORMATION: OD298 Light chain

<400> SEQUENCE: 237

Tyr Arg Lys Leu Asp Ile Gln Leu Thr Gln Ser Pro Ala Ile Leu Ser
1               5                   10                  15

Val Ser Pro Gly Glu Arg Val Ser Phe Ser Cys Arg Ala Ser Gln Ser
```

```
            20                  25                  30

Ile Gly Thr Ser Ile His Trp Tyr Gln Gln Arg Thr Asn Gly Ser Pro
        35                  40                  45

Arg Leu Leu Ile Lys Tyr Ala Ser Glu Ser Ile Ser Gly Ile Pro Ser
    50                  55                  60

Arg Phe Ser Gly Ser Gly Ser Gly Thr Asp Phe Thr Leu Ser Ile Asn
65                  70                  75                  80

Ser Val Glu Ser Glu Asp Ile Ala Asp Tyr Tyr Cys Gln Gln Ser Asn
                85                  90                  95

Ser Trp Pro Tyr Thr Phe Gly Gly Gly Pro Ser
            100                 105
```

<210> SEQ ID NO 238
<211> LENGTH: 122
<212> TYPE: PRT
<213> ORGANISM: Artificial Sequence
<220> FEATURE:
<223> OTHER INFORMATION: OD298 Heavy chain

<400> SEQUENCE: 238

```
Phe Arg Glu Ile Gln Val Gln Leu Gln Glu Ser Gly Pro Glu Leu Val
1               5                   10                  15

Arg Pro Gly Val Ser Val Lys Ile Ser Cys Lys Gly Ser Gly Tyr Thr
            20                  25                  30

Phe Thr Asp Tyr Ala Met His Trp Val Lys Gln Ser His Ala Lys Ser
        35                  40                  45

Leu Glu Trp Ile Gly Val Ile Ser Thr Tyr Ser Gly Asn Thr Asn Tyr
    50                  55                  60

Asn Gln Lys Phe Lys Gly Lys Ala Thr Met Thr Val Asp Lys Ser Ser
65                  70                  75                  80

Ser Thr Ala Tyr Met Glu Leu Ala Arg Leu Thr Ser Glu Asp Ser Ala
                85                  90                  95

Ile Tyr Tyr Cys Ala Arg Glu Ala Ser Gly Leu Cys Pro Phe Asp Tyr
            100                 105                 110

Trp Gly Gln Gly Thr Thr Leu Thr Val Pro
        115                 120
```

<210> SEQ ID NO 239
<211> LENGTH: 107
<212> TYPE: PRT
<213> ORGANISM: Artificial Sequence
<220> FEATURE:
<223> OTHER INFORMATION: OD340 Light chain

<400> SEQUENCE: 239

```
Arg Ser Glu Ala Cys Ile Gln Leu Thr Gln Ser Pro Ala Ser Leu Tyr
1               5                   10                  15

Ala Ser Val Gly Glu Thr Val Thr Ile Thr Cys Arg Ala Ser Gly Asn
            20                  25                  30

Ile His Asn Tyr Leu Ala Trp Tyr Gln Gln Lys Gln Gly Lys Ser Pro
        35                  40                  45

Gln Leu Leu Val Tyr Asn Ala Lys Thr Leu Ala Asp Gly Val Pro Ser
    50                  55                  60

Arg Phe Ser Gly Ser Gly Ser Gly Thr Gln Tyr Ser Leu Lys Ile Asn
65                  70                  75                  80

Ser Leu Gln Pro Glu Asp Phe Gly Ser Tyr Tyr Cys Gln His Phe Trp
                85                  90                  95
```

```
Ser Thr Pro Leu Thr Phe Gly Ala Gly Pro Ser
            100                 105


<210> SEQ ID NO 240
<211> LENGTH: 123
<212> TYPE: PRT
<213> ORGANISM: Artificial Sequence
<220> FEATURE:
<223> OTHER INFORMATION: OD340 Heavy chain

<400> SEQUENCE: 240

Leu Pro Glu Ile Glu Val Gln Leu Gln Glu Ser Gly Pro Glu Leu Val
1               5                   10                  15

Lys Pro Gly Ala Ser Val Lys Ile Ser Cys Lys Ala Ser Gly Tyr Thr
            20                  25                  30

Phe Thr Asp Tyr Asn Met His Trp Val Lys Gln Ser His Gly Lys Ser
        35                  40                  45

Leu Glu Trp Ile Gly Tyr Ile Tyr Pro Tyr Asn Gly Gly Thr Gly Tyr
    50                  55                  60

Asn Gln Lys Phe Lys Ser Lys Ala Thr Leu Thr Val Asp Asn Ser Ser
65                  70                  75                  80

Ser Thr Ala Tyr Met Glu Leu Arg Ser Leu Thr Ser Glu Asp Ser Ala
                85                  90                  95

Val Tyr Tyr Cys Ala Arg Ala Asp Gly Asn His Pro Tyr Tyr Phe Asp
            100                 105                 110

Tyr Trp Gly Gln Gly Thr Thr Leu Thr Val Leu
        115                 120


<210> SEQ ID NO 241
<211> LENGTH: 335
<212> TYPE: DNA
<213> ORGANISM: Artificial Sequence
<220> FEATURE:
<223> OTHER INFORMATION: OD7 Light chain

<400> SEQUENCE: 241

tttcggaagc ttgacattca gctgacccag tctccagcca ccctgtctgt gactccagga     60

gatagcgtca gtctttcctg cagggccagc caaagtatta gcaacaacct acactggtat    120

caacaaaaat cacatgagtc tccaaggctt ctcatcaagt atgcttccca gtccatctct    180

gggatcccct ccaggttcag tggcagtgga tcagggacag atttcactct cagtatcaac    240

agtgtggaga ctgaagattt tggaatgtat ttctgtcaac agagtaacag ctggccgctc    300

acgttcggtg ctggaccaag ctgagcmaaa cggtt                               335


<210> SEQ ID NO 242
<211> LENGTH: 379
<212> TYPE: DNA
<213> ORGANISM: Artificial Sequence
<220> FEATURE:
<223> OTHER INFORMATION: OD7 Heavy chain

<400> SEQUENCE: 242

tcttccggaa atttgaggtt cagctgcagc agtctggggc tgagctggtg aggcctggag     60

cttcagtgaa gctgtcctgc aaggcttctg gctactcctt caccagctac tggatgaact    120

gggtgaagca gaggcctgga caaggccttg agtggattgg catgattcat ccttccgata    180

gtgaaactag gttaaatcag aagttcaagg acaaggccac attgactgta gacaaatcct    240

ccagcacagc ctacatgcaa ctcagcagcc cgacatctga ggactctgcg gtctattact    300
```

gtgcaagacc ggtagtagct acagggaggt actattctat ggactactgg ggtcaaggaa 360
cctcagtcac cgtcccccc 379

<210> SEQ ID NO 243
<211> LENGTH: 348
<212> TYPE: DNA
<213> ORGANISM: Artificial Sequence
<220> FEATURE:
<223> OTHER INFORMATION: OD111A Light chain

<400> SEQUENCE: 243
gacattcagc tgacccagtc tccagcctcc ctatctgcat ctgtgggaga aactgtcacc 60
atcacatgtc gagcaagtga gaatatttac agttatttag catggtatca gcagaaacag 120
ggaaaatctc ctcagctcct ggtctataat gcaaaaacct tagcagaagg tgtgccatca 180
aggttcagtg gcagtggatc aggcacacag ttttctctga agatcaacag cctgcagcct 240
gaagattttg ggagttatta ctgtcaacat cattatggta ctccgctcac gttcggtgct 300
gggaccaagc tggagctgaa acgggctgat gctgcaccaa ctgtatcc 348

<210> SEQ ID NO 244
<211> LENGTH: 381
<212> TYPE: DNA
<213> ORGANISM: Artificial Sequence
<220> FEATURE:
<223> OTHER INFORMATION: OD111A Heavy chain

<400> SEQUENCE: 244
tcttccggaa ttccaggttc agctgcagca gtctggagct gagctgatga agcctggggc 60
ctcagtgaag atatcctgca aggctactgg ctacacattc agtagctact ggatagagtg 120
ggtaaagcag aggcctggac atggccttga gtggattgga gagattttac ctggaagtgg 180
tagtactaac tacaatgaga agttcaaggg caaggccaca ttcactgcag atacatcctc 240
caacacagcc tacatgcaac tcagcagcct gacatctgag gactctgccg tctattactg 300
tgcaagaagg aaatggggta actacgttaa ttactatgct atggactact ggggtcaagg 360
aacctcagtc accgttctcc c 381

<210> SEQ ID NO 245
<211> LENGTH: 330
<212> TYPE: DNA
<213> ORGANISM: Artificial Sequence
<220> FEATURE:
<223> OTHER INFORMATION: OD169B Light chain

<400> SEQUENCE: 245
tctcggaagc ttgaattcag ctgacccagt ctccagcaat catgtctgca tctccagggg 60
agaaggtcac catgacctgc agtgccagct caagtgtaag ttacatgcac tggtaccagc 120
agaagtcagg cacctccccc aaaagatgga tttatgacac atccaaactg gcttctggag 180
tccctgctcg cttcagtggc agtgggtctg ggacctctta ctctctcaca atcagcagca 240
tggaggctga agatgctgcc acttattact gccagcagtg gagtagtaac ccacccacgt 300
tcggctcggg acaaagtgaa taagccggtt 330

<210> SEQ ID NO 246
<211> LENGTH: 348
<212> TYPE: DNA
<213> ORGANISM: Artificial Sequence
<220> FEATURE:
<223> OTHER INFORMATION: OD169B Heavy chain -continued

<400> SEQUENCE: 246

```
tcttccggaa ttcgaggttc agctggagga gtctggacct ggcctggtgg cgccctcaca     60
gagcctgtcc atcacatgca ctgtctcagg gttctcatta accagctatg gtgtaagctg    120
ggttcgccag cctccaggaa agggtctgga gtggctggga gtaatatggg gtgacgggag    180
cacaaattat cattcagctc tcatatccag actgagcatc agcaaggata actccaagag    240
ccaagttttc ttaaaactga acagtctgca aactgatgac acagccacgt actactgtgc    300
cggttaccgc ggttactggg gccaagggac tctggtcacg actccgac                 348
```

<210> SEQ ID NO 247
<211> LENGTH: 363
<212> TYPE: DNA
<213> ORGANISM: Artificial Sequence
<220> FEATURE:
<223> OTHER INFORMATION: OD184 Light chain

<400> SEQUENCE: 247

```
gacattcagc tgacccagtc tccattctcc aatccagtca ctcttggaac atcagcttcc     60
atctcctgca ggtctagtaa gagtctccta catagtaatg gcatcactta tttgtattgg    120
tatctgcaga agccaggcca gtctcctcag ctcctgattt atcagatgtc caaccttgcc    180
tcaggagtcc cagacaggtt cagtagcagt gggtcaggaa ctgatttcac actgagaatc    240
agcagagtgg aggctgagga tgtgggtgtt tattactgtg ctcaaaatct agaacttcct    300
ccgacgttcg gtggaggcac caagctggaa atcaaacggg ctgatgctgc accaactgta    360
tcc                                                                  363
```

<210> SEQ ID NO 248
<211> LENGTH: 377
<212> TYPE: DNA
<213> ORGANISM: Artificial Sequence
<220> FEATURE:
<223> OTHER INFORMATION: OD184 Heavy chain

<400> SEQUENCE: 248

```
tcttccggaa ttccaggttc agctgcagca gtctggttct gaactgagga gtcctgggtc     60
ttcagtaaag ctttcatgca aggattttga ttcagaagtc ttccctattg cttatatgag    120
ttgggttagg cagaagcctg ggcatggatt tgaatggatt ggagacatac tcccaagtat    180
tggtagaaca atctatggag agaagtttga ggacaaagcc acactggatg cagacacagt    240
gtccaacaca gcctacttgg agctcaacag tctgacatct gaggactctg ctatctacta    300
ctgtgcaagg gagggcagct cgggctacgg ggcctggttt gcttactggg gccaagggac    360
tctggtcact ctctgcc                                                   377
```

<210> SEQ ID NO 249
<211> LENGTH: 351
<212> TYPE: DNA
<213> ORGANISM: Artificial Sequence
<220> FEATURE:
<223> OTHER INFORMATION: OD185 Light chain

<400> SEQUENCE: 249

```
tcggaagctt gacattcagc tgacccagtc tccatcctcc ctgagtgtgt cagcaggaga     60
gaaggtcact atgagctgca agtccagtca gagtctgtta aacagtggaa atcaaaagaa    120
ctacttggcc tggtaccagc agaaaccagg gcagcctcct aaactgttga tctacggggc    180
```

atccactagg gaatctgggg tccctgatcg cttcacaggc agtggatctg gaaccgattt 240
cactcttacc atcagcagtg tgcaggctga agacctggca gtttattact gtcagaatga 300
tcatagttat ccgtacacgt tyggaggggg accaagctga aataataggt t 351

<210> SEQ ID NO 250
<211> LENGTH: 351
<212> TYPE: DNA
<213> ORGANISM: Artificial Sequence
<220> FEATURE:
<223> OTHER INFORMATION: OD185 Heavy chain

<400> SEQUENCE: 250
tcggaagctt gacattcagc tgacccagtc tccatcctcc ctgagtgtgt cagcaggaga 60
gaaggtcact atgagctgca agtccagtca gagtctgtta aacagtggaa atcaaaagaa 120
ctacttggcc tggtaccagc agaaaccagg gcagcctcct aaactgttga tctacggggc 180
atccactagg gaatctgggg tccctgatcg cttcacaggc agtggatctg gaaccgattt 240
cactcttacc atcagcagtg tgcaggctga agacctggca gtttattact gtcagaatga 300
tcatagttat ccgtacacgt tyggaggggg accaagctga aataataggt t 351

<210> SEQ ID NO 251
<211> LENGTH: 335
<212> TYPE: DNA
<213> ORGANISM: Artificial Sequence
<220> FEATURE:
<223> OTHER INFORMATION: OD196 Light chain

<400> SEQUENCE: 251
tgtcggaagc ttgacattca gctgacccag tctccaaaat tcatgtccac atcagtagga 60
gacagggtca gcgtcacctg caaggccagt cagaatgtgg gtactaatgt agcctggtat 120
caacagaaac cagggcaatc tcctaaagca ctgatttact cggcatccta ccggtacagt 180
ggagtccctg atcgcttcac aggcagtgga tctgggacag atttcactct caccatcagc 240
aatgtgcagt ctgaagactt ggcagagtat ttctgtcagc aatataacag ctatccgtac 300
acgttcggag ggggaccaag ctgaataaac gggtt 335

<210> SEQ ID NO 252
<211> LENGTH: 355
<212> TYPE: DNA
<213> ORGANISM: Artificial Sequence
<220> FEATURE:
<223> OTHER INFORMATION: OD196 Heavy chain

<400> SEQUENCE: 252
tcttccggaa ttcgaggttc agctgcagga gtctggacct gagctggtga agcctggggc 60
ttcagtgaag atatcctgca agacttctgg atacacattc actgaataca ccatgcactg 120
ggtgaagcag agccatggaa agagccttga gtggattgga ggtattaatc ctaacaatgg 180
tggtactagc tacaaccaga agttcaaggg caaggccaca ttgactgtag acaagtcctc 240
cagcacagcc tacatggagc tccgcagcct gacatctgag gattctgcag tctattactg 300
tgcaactggg tatgctatgg actactgggg tcaaggaacc tcagtcacct tctcc 355

<210> SEQ ID NO 253
<211> LENGTH: 351
<212> TYPE: DNA
<213> ORGANISM: Artificial Sequence
<220> FEATURE:
<223> OTHER INFORMATION: OD210A Light chain

<400> SEQUENCE: 253 tttttggaa gcttgacatt gtgctgaccc aatctccagc ttctttggct gtgtctctag 60
ggcagagggc caccatctcc tgcagagcca gcgaaagtgt tgataattat ggcattagtt 120
ttatgaactg gttccaacag aaaccaggac agccacccaa actcctcatc tatgctgcat 180
ccaaccaagg atccggggtc cctgccaggt ttagtggcag tgggtctggg acagacttca 240
gcctcaacat ccatcctatg gaggaggatg atactgcaat gtatttctgt cagcaaagta 300
aggaggttcc tcggacgttc ggtggaggca ccaagctgaa tcaaagcggt t 351

<210> SEQ ID NO 254
<211> LENGTH: 375
<212> TYPE: DNA
<213> ORGANISM: Artificial Sequence
<220> FEATURE:
<223> OTHER INFORMATION: OD210A Heavy chain

<400> SEQUENCE: 254
tcttccggaa attccaggtt cagctgcagc agtctggagg tggcctggtg cagcctggag 60
gatccctgaa actctcctgt gcagcctcag gattcgattt tagtagatac tggatgagtt 120
gggtccggca ggctccaggg aaagggctag aatggattgg agaaattaat ccagatagca 180
gtacgataaa ctatacgcca tctctaaagg ataaattcat catctccaga gacaacgcca 240
aaaatacgct gtacctgcaa atgagcaaag tgagatctga ggacacagcc ctttattact 300
gtgcaagacg gggaatctac tatggtaact actgtgacta ctggggccaa ggcaccactc 360
tcacagttcc ctgcc 375

<210> SEQ ID NO 255
<211> LENGTH: 349
<212> TYPE: DNA
<213> ORGANISM: Artificial Sequence
<220> FEATURE:
<223> OTHER INFORMATION: OD225 Light chain

<400> SEQUENCE: 255
ggaagcttga cattcagctg acccagtctc catcctccct gagtgtgtca gcaggagaga 60
aggtcactat gagctgcaag tccagtcaga gtctgttaaa cagtggaaat caaaagaact 120
acttggcctg gtaccagcag aaaccagggc agcctcctaa actgttgatc tacggggcat 180
ccactaggga atctggggtc cctgatcgct tcacaggcag tggatctgga accgatttca 240
ctcttaccat cagcagtgtg caggctgaag acctggcagt ttattactgt cagaatgatc 300
atagttatcc attcacgttc ggctcgggac aaagtgaata aagcgggtt 349

<210> SEQ ID NO 256
<211> LENGTH: 365
<212> TYPE: DNA
<213> ORGANISM: Artificial Sequence
<220> FEATURE:
<223> OTHER INFORMATION: OD225 Heavy chain

<400> SEQUENCE: 256
tcttccggaa tttcaggttc agctgcagca gtctggggct gaactggtga agcctgggac 60
ttcagtgaaa atgtcctgca aggcttctgg ctacaccttc accagctact ggatgcactg 120
ggtgaagcag aggccgggac aaggccttga gtggattgga gatatttatc ctggtagtga 180
tagtactaac tacaatgaga agttcaagag caaggccaca ctgactgtag acacatcctc 240

-continued cagcacagcc tacatgcaac tcagcagcct gacatctgag gactctgcgg tctattactg 300
tgcaaggtgc gacttttact ggtacttcga tgtctggggc gcaggaccac ggtcaccgtc 360
cctag 365

<210> SEQ ID NO 257
<211> LENGTH: 356
<212> TYPE: DNA
<213> ORGANISM: Artificial Sequence
<220> FEATURE:
<223> OTHER INFORMATION: OD234 Light chain

<400> SEQUENCE: 257
gacattgtgc tgacccaatc tccagcttct ttagctgtat ctctggggca gagggccacc 60
atctcataca gggccagcaa aagtgtcagt acatctggct atagttatat gcactggaac 120
caacagaaac caggacagcc acccagactc ctcatctatc ttgtatccaa cctagaatct 180
ggggtccctg ccaggttcag tggcagtggg tctgggacag acttcaccct caacatccat 240
cctgtggagg aggaggatgc tgcaacctat tactgtcagc acattaggga gcttacacgt 300
tcggaggggg gaccaagctg gaaataaaac gggctgatgc tgcaccaact gtatcc 356

<210> SEQ ID NO 258
<211> LENGTH: 383
<212> TYPE: DNA
<213> ORGANISM: Artificial Sequence
<220> FEATURE:
<223> OTHER INFORMATION: OD234 Heavy chain

<400> SEQUENCE: 258
tctttcggaa tttgaggtcc agctgcagca gtcaggacct gagctggtga agcctggagc 60
ttcaatgaag atatcctgca aggcttctgg ttactcattc actggctaca ccatgaactg 120
ggtgagccat ggaaagaacc ttgagtggat tggacttatt aatccttaca atggtggtac 180
tagctacaac cagaagttca agggcaaggc cacattaact gtagacaagt catccagcac 240
agcctacatg gagctcctca gtctgacatc tgaggactct gcagtctatt actgtgcaag 300
agttagggcc tactatggta actacgagct tttttactgg tacttcgatg tctggggcgc 360
aggaccacgg tcaccgtccc ccc 383

<210> SEQ ID NO 259
<211> LENGTH: 348
<212> TYPE: DNA
<213> ORGANISM: Artificial Sequence
<220> FEATURE:
<223> OTHER INFORMATION: OD241 Light chain

<400> SEQUENCE: 259
gacattcagc tgacccagtc tccagcatcc ctgtccgtgg ctacaggaga aaaagtcact 60
atcagatgca taaccagcac tgatattgat gatgatatga actggtacca gcagaagcca 120
ggggaacctc ctaagctcct tatttcagaa ggcaatactc ttcgtcctgg agtcccatcc 180
cgattctcca gcagtggcta tggcacagat tttgttttta caattgaaaa cacgctctca 240
gaagatgttg cagattacta ctgtttgcaa agtgataaca tgccattcac gttcggctcg 300
gggacaaagt tggaaataag acgggctgat gctgcaccaa ctgtatcc 348

<210> SEQ ID NO 260
<211> LENGTH: 376
<212> TYPE: DNA
<213> ORGANISM: Artificial Sequence
<220> FEATURE:
<223> OTHER INFORMATION: OD241 Heavy chain

<400> SEQUENCE: 260
tcttccggaa attccaggtt cagctgcagg agtctggccc tgggatattg cagccctccc 60
agaccctcag tctgacttgt tctttctctg ggttttcact gagcacttct ggtatgagtg 120
taggctggat tcgtcagcct tcagggaagg gtctggagtg gctggcacac atttggtgga 180
atgatgataa gtactataac ccagccctga aaagccggct cacaatctcc aaggatacct 240
ccaacaacca ggtattcctc aagatcgcca gtgtggtcac tgcagatact gccacatact 300
actgtgctcg aatagctagg gaggtacgac ggtacttcga tgtctggggc gcaggaccac 360
ggtcaccttc cctccc 376

<210> SEQ ID NO 261
<211> LENGTH: 335
<212> TYPE: DNA
<213> ORGANISM: Artificial Sequence
<220> FEATURE:
<223> OTHER INFORMATION: OD244 Light chain

<400> SEQUENCE: 261
tatcggaagc ttgacattca gctgacccag tctccagcaa tcatgtctgc atctccaggg 60
gagaaggtca ccatatcctg cagtgccagc tcaagtgtaa gttacatgta ctggtaccag 120
cagaagccag gatcctcccc caaaccctgg atttatcgca catccaacct ggcttctgga 180
gtccctgctc gcttcagtgg cagtgggtct gggacctctt actctctcac aatcagcagc 240
atggaggctg aagatgctgc cacttattac tgccagcagt atcatagtta ccccatgtac 300
acgttcggag gggaccaag ctgaaataaa cggtt 335

<210> SEQ ID NO 262
<211> LENGTH: 367
<212> TYPE: DNA
<213> ORGANISM: Artificial Sequence
<220> FEATURE:
<223> OTHER INFORMATION: OD244 Heavy chain

<400> SEQUENCE: 262
tcttccggaa attgaggttc agctgcagca gtctgggact gtgctggcaa ggcctggggc 60
ttcagtgaag atgtcctgca aggcttctgg ctacaccttt accagctact ggatgcactg 120
ggtaaaacag aggcctggac agggtctgga atggattggc gctatttatc ctggaaatag 180
tgatactagc tacaaccaga agttcaaggg caaggccaaa ctgactgcag tcacatccac 240
cagcactgcc tacatggagc tcagcagcct gacaaatgag gactctgcgg tctattactg 300
tacaagatcc gggcccccat actggtactt cgatgtctgg ggcgcaggac cacggtcacc 360
tccctac 367

<210> SEQ ID NO 263
<211> LENGTH: 334
<212> TYPE: DNA
<213> ORGANISM: Artificial Sequence
<220> FEATURE:
<223> OTHER INFORMATION: OD270 Light chain

<400> SEQUENCE: 263
tctcggaagc tttgcattca gctgacccag tctccatcct cactgtctgc atctctggga 60
ggcaaagtca ccatcacttg caaggcaagc caagacatta acaagtatat agcttggtac 120
caacacaagc ctggaaaagg tcctaggctg ctcatacatt acacatctac attacagcca 180
ggcatcccat caaggttcag tggaagtggg tctgggagag attattcctt cagcatcagc 240
aacctggagc ctgaagatat tgcaacttat tattgtctac agtatgataa tctgtggacg 300
ttcggtggag gcaccaagct gaatcaagcg ggtt 334

<210> SEQ ID NO 264
<211> LENGTH: 360
<212> TYPE: DNA
<213> ORGANISM: Artificial Sequence
<220> FEATURE:
<223> OTHER INFORMATION: OD270 Heavy chain

<400> SEQUENCE: 264
tctcttccgg aaatttgagg ttcagctgca ggagtctggg gctgagctgg tgaggcctgg 60
agcttcagtg aagctgtcct gcaaggcttc tggctactcc ttcaccagct actggatgaa 120
ctgggtgaag cagaggcctg gacaaggcct tgagtggatt ggcatgattc atccttccga 180
tagtgaaact aggttaaatc agaagttcaa ggacaaggcc acattgactg tagacaaatc 240
ctccagcaca gcctacatgc aactcagcag cccgacatct gaggactctg cggtctatta 300
ctgtgttgat ggctatgcta tggactactg gggtcaagga acctcagtca ccgttcctcc 360

<210> SEQ ID NO 265
<211> LENGTH: 358
<212> TYPE: DNA
<213> ORGANISM: Artificial Sequence
<220> FEATURE:
<223> OTHER INFORMATION: OD296 Light chain

<400> SEQUENCE: 265
tcggaagctt gacattcagc tgacccagtc tccatcctcc ctggctgtga cagcaggaga 60
gaaggtcact atgagatgca agtccagtca gagtcttttg tggagtgtaa accaaaataa 120
ctacttatcc tggtaccagc agaaacaagg gcagcctcct aaactgctta tctatggggc 180
atccattaga gaatcttggg tccctgatcg attcacagga agtggatctg ggacagactt 240
cactctcacc attagcaatg tgcatgctga agacctagca gtttattact gtcagcacaa 300
tcatggcagc tttctccccc tcacgttcgg tgctggacca agctgagcma agcgggtt 358

<210> SEQ ID NO 266
<211> LENGTH: 378
<212> TYPE: DNA
<213> ORGANISM: Artificial Sequence
<220> FEATURE:
<223> OTHER INFORMATION: OD296 Heavy chain

<400> SEQUENCE: 266
tcttccggaa atttgaggtt cagctgcagg agtctggacc tgagctggta aagcctgggg 60
cttcagtgaa gatgtcctgc aaggcttctg gatacacatt cactagctat gttatgcact 120
gggtgaagca gaagcctggg cagggccttg agtggattgg atatattaat ccttacaatg 180
atggtactaa gtacaatgag aagttcaaag gcaaggccac actgacttca gacaaatcct 240
ccagcacagc ctacatggag ctcagcagcc tgacctctga ggactctgcg gtctattact 300
gtgcaagaag ggaaaagtat ggtaactacg tgggggctat ggactactgg ggtcaaggaa 360
cctcagtcac cgtcctcc 378

<210> SEQ ID NO 267
<211> LENGTH: 335

<212> TYPE: DNA
<213> ORGANISM: Artificial Sequence
<220> FEATURE:
<223> OTHER INFORMATION: OD298 Light chain

<400> SEQUENCE: 267
tatcggaagc ttgacattca gctgacccag tctccagcca tcctgtctgt gagtccagga 60
gaaagagtca gtttctcctg cagggccagt cagagcattg gcacaagcat acactggtat 120
cagcaaagaa caaatggttc tccaaggctt ctcataaagt atgcttctga gtctatctct 180
gggatccctt ccaggtttag tggcagtgga tcagggacag attttactct tagcatcaac 240
agtgtggagt ctgaagatat tgcagattat tactgtcaac aaagtaatag ctggccgtac 300
acgttcggag gggggaccaag ctgaataagc gggtt 335

<210> SEQ ID NO 268
<211> LENGTH: 370
<212> TYPE: DNA
<213> ORGANISM: Artificial Sequence
<220> FEATURE:
<223> OTHER INFORMATION: OD298 Heavy chain

<400> SEQUENCE: 268
tcttccggga aattcaggtt cagctgcagg agtctgggcc tgagctggtg aggcctgggg 60
tctcagtgaa gatttcctgc aagggttccg gctacacatt cactgattat gctatgcact 120
gggtgaagca gagtcatgca aagagtctag agtggattgg agttattagt acttactctg 180
gtaatacaaa ctacaaccag aagtttaagg gcaaggccac aatgactgta gacaaatcct 240
ccagcacagc ctatatggaa cttgccagat tgacatctga ggattctgcc atctattact 300
gtgcaagaga ggcatccgga ctatgccctt ttgactactg gggccaaggc accactctca 360
cagtccctcc 370

<210> SEQ ID NO 269
<211> LENGTH: 335
<212> TYPE: DNA
<213> ORGANISM: Artificial Sequence
<220> FEATURE:
<223> OTHER INFORMATION: OD340 Light chain

<400> SEQUENCE: 269
cggtcggaag cttgcattca gctgacccag tctccagcct ccctatatgc atctgtggga 60
gaaactgtca ccatcacatg tcgagcaagt gggaatattc acaattattt agcatggtat 120
cagcagaaac agggaaaatc tcctcagctc ctggtttata atgcaaaaac cttagcagat 180
ggtgtgccat caaggttcag tggcagtgga tcaggaacac aatattctct caagatcaac 240
agcctgcagc ctgaagattt tgggagttat tactgtcaac atttttggag tactccgctc 300
acgttcggtg ctggaccaag ctgagctaat cggat 335

<210> SEQ ID NO 270
<211> LENGTH: 372
<212> TYPE: DNA
<213> ORGANISM: Artificial Sequence
<220> FEATURE:
<223> OTHER INFORMATION: OD340 Heavy chain

<400> SEQUENCE: 270
tcttccggaa attgaggtgc agctgcagga gtcaggacct gagctggtga aacctggggc 60
ctcagtgaag atatcctgca aggcttctgg atacacattc actgactaca acatgcactg 120

```
ggtgaagcag agccatggaa agagccttga gtggattgga tatatttatc cttacaatgg    180

tggtactggc tacaaccaga agttcaagag caaggccaca ttgactgtag acaattcctc    240

cagcacagcc tacatggagc tccgcagcct gacatctgag gactctgcag tctattactg    300

tgcaagagcg gatggtaacc acccctacta ctttgactac tggggccaag gcaccactct    360

cacagtcctg ac                                                        372


<210> SEQ ID NO 271
<211> LENGTH: 20
<212> TYPE: DNA
<213> ORGANISM: Artificial Sequence
<220> FEATURE:
<223> OTHER INFORMATION: heavy chain 5'MH1 primer
<220> FEATURE:
<221> NAME/KEY: misc_feature
<222> LOCATION: (6)..(6)
<223> OTHER INFORMATION: a or g or c or t/u

<400> SEQUENCE: 271

sargtnmagc tgsagsagtc                                                 20


<210> SEQ ID NO 272
<211> LENGTH: 23
<212> TYPE: DNA
<213> ORGANISM: Artificial Sequence
<220> FEATURE:
<223> OTHER INFORMATION: heavy chain 5'MH2 primer
<220> FEATURE:
<221> NAME/KEY: misc_feature
<222> LOCATION: (6)..(6)
<223> OTHER INFORMATION: a or g or c or t/u unknown, or other

<400> SEQUENCE: 272

sargtnmagc tgsagsagtc wgg                                             23


<210> SEQ ID NO 273
<211> LENGTH: 24
<212> TYPE: DNA
<213> ORGANISM: Artificial Sequence
<220> FEATURE:
<223> OTHER INFORMATION: heavy chain IgA primer

<400> SEQUENCE: 273

gatggtggga tttctcgcag actc                                            24


<210> SEQ ID NO 274
<211> LENGTH: 25
<212> TYPE: DNA
<213> ORGANISM: Artificial Sequence
<220> FEATURE:
<223> OTHER INFORMATION: heavy chain IgE primer

<400> SEQUENCE: 274

taaggggtag agctgagggt tcctg                                           25


<210> SEQ ID NO 275
<211> LENGTH: 24
<212> TYPE: DNA
<213> ORGANISM: Artificial Sequence
<220> FEATURE:
<223> OTHER INFORMATION: heavy chain IgM primer

<400> SEQUENCE: 275

gacatttggg aaggactgac tctc                                            24
```

<210> SEQ ID NO 276
<211> LENGTH: 27
<212> TYPE: DNA
<213> ORGANISM: Artificial Sequence
<220> FEATURE:
<223> OTHER INFORMATION: heavy chain IgG1 primer

<400> SEQUENCE: 276
atagacagat gggggtgtcg ttttggc 27

<210> SEQ ID NO 277
<211> LENGTH: 23
<212> TYPE: DNA
<213> ORGANISM: Artificial Sequence
<220> FEATURE:
<223> OTHER INFORMATION: heavy chain IgG2a primer

<400> SEQUENCE: 277
cttgaccagg catcctagag tca 23

<210> SEQ ID NO 278
<211> LENGTH: 24
<212> TYPE: DNA
<213> ORGANISM: Artificial Sequence
<220> FEATURE:
<223> OTHER INFORMATION: heavy chain IgG2b primer

<400> SEQUENCE: 278
aggggccagt ggatagactg atgg 24

<210> SEQ ID NO 279
<211> LENGTH: 24
<212> TYPE: DNA
<213> ORGANISM: Artificial Sequence
<220> FEATURE:
<223> OTHER INFORMATION: heavy chain IgG3 primer

<400> SEQUENCE: 279
agggaccaag ggatagacag atgg 24

<210> SEQ ID NO 280
<211> LENGTH: 24
<212> TYPE: DNA
<213> ORGANISM: Artificial Sequence
<220> FEATURE:
<223> OTHER INFORMATION: light chain 5'MK primer

<400> SEQUENCE: 280
gayattgtgm tsacmcarwc tmca 24

<210> SEQ ID NO 281
<211> LENGTH: 21
<212> TYPE: DNA
<213> ORGANISM: Artificial Sequence
<220> FEATURE:
<223> OTHER INFORMATION: light chain 3'CK primer

<400> SEQUENCE: 281
ggatacagtt ggtgcagcat c 21

<210> SEQ ID NO 282
<211> LENGTH: 30
<212> TYPE: DNA
<213> ORGANISM: Artificial Sequence
<220> FEATURE:
<223> OTHER INFORMATION: light chain primer 6

<400> SEQUENCE: 282
gacattgtgc tgacccaatc tccagcttct 30

<210> SEQ ID NO 283
<211> LENGTH: 24
<212> TYPE: DNA
<213> ORGANISM: Artificial Sequence
<220> FEATURE:
<223> OTHER INFORMATION: light chain primer 7

<400> SEQUENCE: 283
gacattcagc tgacccagtc tcca 24

<210> SEQ ID NO 284
<211> LENGTH: 20
<212> TYPE: DNA
<213> ORGANISM: Artificial Sequence
<220> FEATURE:
<223> OTHER INFORMATION: heavy chain 5'MH1 primer
<220> FEATURE:
<221> NAME/KEY: misc_feature
<222> LOCATION: (6)..(6)
<223> OTHER INFORMATION: a or g or c or t/u unknown, or other

<400> SEQUENCE: 284
sargtnmagc tgsagsagtc 20

<210> SEQ ID NO 285
<211> LENGTH: 23
<212> TYPE: DNA
<213> ORGANISM: Artificial Sequence
<220> FEATURE:
<223> OTHER INFORMATION: heavy chain 5'MH2 primer
<220> FEATURE:
<221> NAME/KEY: misc_feature
<222> LOCATION: (6)..(6)
<223> OTHER INFORMATION: a or g or c or t/u unknown, or other

<400> SEQUENCE: 285
sargtnmagc tgsagsagtc wgg 23

<210> SEQ ID NO 286
<211> LENGTH: 24
<212> TYPE: DNA
<213> ORGANISM: Artificial Sequence
<220> FEATURE:
<223> OTHER INFORMATION: heavy chain IgA primer

<400> SEQUENCE: 286
gatggtggga tttctcgcag actc 24

<210> SEQ ID NO 287
<211> LENGTH: 25
<212> TYPE: DNA
<213> ORGANISM: Artificial Sequence
<220> FEATURE:
<223> OTHER INFORMATION: heavy chain IgE primer

<400> SEQUENCE: 287
taaggggtag agctgagggt tcctg 25

<210> SEQ ID NO 288
<211> LENGTH: 24
<212> TYPE: DNA
<213> ORGANISM: Artificial Sequence
<220> FEATURE:
<223> OTHER INFORMATION: heavy chain IgM primer

<400> SEQUENCE: 288
gacatttggg aaggactgac tctc 24

<210> SEQ ID NO 289
<211> LENGTH: 27
<212> TYPE: DNA
<213> ORGANISM: Artificial Sequence
<220> FEATURE:
<223> OTHER INFORMATION: heavy chain IgM1 primer

<400> SEQUENCE: 289
atagacagat gggggtgtcg ttttggc 27

<210> SEQ ID NO 290
<211> LENGTH: 23
<212> TYPE: DNA
<213> ORGANISM: Artificial Sequence
<220> FEATURE:
<223> OTHER INFORMATION: heavy chain IgM2a primer

<400> SEQUENCE: 290
cttgaccagg catcctagag tca 23

<210> SEQ ID NO 291
<211> LENGTH: 24
<212> TYPE: DNA
<213> ORGANISM: Artificial Sequence
<220> FEATURE:
<223> OTHER INFORMATION: heavy chain IgM2b primer

<400> SEQUENCE: 291
aggggccagt ggatagactg atgg 24

<210> SEQ ID NO 292
<211> LENGTH: 24
<212> TYPE: DNA
<213> ORGANISM: Artificial Sequence
<220> FEATURE:
<223> OTHER INFORMATION: heavy chain IgM3 primer

<400> SEQUENCE: 292
agggaccaag ggatagacag atgg 24

<210> SEQ ID NO 293
<211> LENGTH: 24
<212> TYPE: DNA
<213> ORGANISM: Artificial Sequence
<220> FEATURE:
<223> OTHER INFORMATION: light chain 5'MK primer

<400> SEQUENCE: 293
gayattgtgm tsacmcarwc tmca 24

<210> SEQ ID NO 294
<211> LENGTH: 21
<212> TYPE: DNA
<213> ORGANISM: Artificial Sequence
<220> FEATURE:
<223> OTHER INFORMATION: light chain 3'CK primer

<400> SEQUENCE: 294
ggatacagtt ggtgcagcat c 21

<210> SEQ ID NO 295

<211> LENGTH: 30
<212> TYPE: DNA
<213> ORGANISM: Artificial Sequence
<220> FEATURE:
<223> OTHER INFORMATION: light chain primer6

<400> SEQUENCE: 295
gacattgtgc tgacccaatc tccagcttct 30

<210> SEQ ID NO 296
<211> LENGTH: 24
<212> TYPE: DNA
<213> ORGANISM: Artificial Sequence
<220> FEATURE:
<223> OTHER INFORMATION: light chain primer7

<400> SEQUENCE: 296
gacattcagc tgacccagtc tcca 24

<210> SEQ ID NO 297
<211> LENGTH: 19
<212> TYPE: DNA
<213> ORGANISM: Artificial Sequence
<220> FEATURE:
<223> OTHER INFORMATION: Scleraxis forward primer

<400> SEQUENCE: 297
agaaagttga gcaaggacc 19

<210> SEQ ID NO 298
<211> LENGTH: 18
<212> TYPE: DNA
<213> ORGANISM: Artificial Sequence
<220> FEATURE:
<223> OTHER INFORMATION: Scleraxis Reverse primer

<400> SEQUENCE: 298
ctgtctgtac gtccgtct 18

<210> SEQ ID NO 299
<211> LENGTH: 18
<212> TYPE: DNA
<213> ORGANISM: Artificial Sequence
<220> FEATURE:
<223> OTHER INFORMATION: Runx2 forward primer

<400> SEQUENCE: 299
gtctcactgc ctctcact 18

<210> SEQ ID NO 300
<211> LENGTH: 20
<212> TYPE: DNA
<213> ORGANISM: Artificial Sequence
<220> FEATURE:
<223> OTHER INFORMATION: Runx2 reverse primer

<400> SEQUENCE: 300
tacacacatc tcctcccttc 20

<210> SEQ ID NO 301
<211> LENGTH: 18
<212> TYPE: DNA
<213> ORGANISM: Artificial Sequence
<220> FEATURE:
<223> OTHER INFORMATION: hCOL alpha 1 forward primer

<400> SEQUENCE: 301
ggaggagagt caggaagg 18

<210> SEQ ID NO 302
<211> LENGTH: 20
<212> TYPE: DNA
<213> ORGANISM: Artificial Sequence
<220> FEATURE:
<223> OTHER INFORMATION: hCOL alpha 1 reverse primer

<400> SEQUENCE: 302
tcagcaacac agttacacaa 20

<210> SEQ ID NO 303
<211> LENGTH: 20
<212> TYPE: DNA
<213> ORGANISM: Artificial Sequence
<220> FEATURE:
<223> OTHER INFORMATION: Osteopontin forward primer

<400> SEQUENCE: 303
ctgttgcctg tctctaaacc 20

<210> SEQ ID NO 304
<211> LENGTH: 20
<212> TYPE: DNA
<213> ORGANISM: Artificial Sequence
<220> FEATURE:
<223> OTHER INFORMATION: Osteopontin reverse primer

<400> SEQUENCE: 304
caccatcatc aaattctcct 20

<210> SEQ ID NO 305
<211> LENGTH: 20
<212> TYPE: DNA
<213> ORGANISM: Artificial Sequence
<220> FEATURE:
<223> OTHER INFORMATION: Ostrerix forward primer

<400> SEQUENCE: 305
ttgacatgta cccctttctg 20

<210> SEQ ID NO 306
<211> LENGTH: 20
<212> TYPE: DNA
<213> ORGANISM: Artificial Sequence
<220> FEATURE:
<223> OTHER INFORMATION: Ostrerix reverse primer

<400> SEQUENCE: 306
caatacccct gatgaagagg 20

<210> SEQ ID NO 307
<211> LENGTH: 20
<212> TYPE: DNA
<213> ORGANISM: Artificial Sequence
<220> FEATURE:
<223> OTHER INFORMATION: DMP-1 forward primer

<400> SEQUENCE: 307
gactctcaag aagacagcaa 20

<210> SEQ ID NO 308
<211> LENGTH: 18
<212> TYPE: DNA

<213> ORGANISM: Artificial Sequence
<220> FEATURE:
<223> OTHER INFORMATION: DMP-1 reverse primer

<400> SEQUENCE: 308
gactcactca ccacctct 18

<210> SEQ ID NO 309
<211> LENGTH: 20
<212> TYPE: DNA
<213> ORGANISM: Artificial Sequence
<220> FEATURE:
<223> OTHER INFORMATION: BSP forward primer

<400> SEQUENCE: 309
taccgagcct atgaagatga 20

<210> SEQ ID NO 310
<211> LENGTH: 20
<212> TYPE: DNA
<213> ORGANISM: Artificial Sequence
<220> FEATURE:
<223> OTHER INFORMATION: BSP reverse primer

<400> SEQUENCE: 310
cttcctgagt tgaacttcga 20

<210> SEQ ID NO 311
<211> LENGTH: 27
<212> TYPE: DNA
<213> ORGANISM: Artificial Sequence
<220> FEATURE:
<223> OTHER INFORMATION: DSPP forward primer

<400> SEQUENCE: 311
cagtacagga tgagttaaat gccagtg 27

<210> SEQ ID NO 312
<211> LENGTH: 23
<212> TYPE: DNA
<213> ORGANISM: Artificial Sequence
<220> FEATURE:
<223> OTHER INFORMATION: DSPP reverse primer

<400> SEQUENCE: 312
ccattccctt ctcccttgtg acc 23

<210> SEQ ID NO 313
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 313
gtatgacaac agcctcaaga t 21

-continued

```
<210> SEQ ID NO 314
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 314

ccttccacga taccaaagtt                                             20
```

IGG TYPE MONOCLONAL ANTIBODIES SPECIFICALLY BINDING TO ODONTOBLAST SURFACE

The ASCII text file "Sequence.txt" created on Dec. 21, 2017, having the size of 127 KB, is incorporated by reference into the specification.

TECHNICAL FIELD

The present invention relates to a composition for the differentiation of a dental pulp stem cell into an odontoblast. Further, the present invention relates to an IgG or IgM type monoclonal antibody that specifically binds to the surface of the differentiated odontoblast from the dental pulp stem cell and a composition and method for identifying the differentiation of the odontoblast, isolating the odontoblast and screening an odontoblast differentiation promoting substance using the same.

BACKGROUND ART

Human-derived dental pulp stem cells (hDPSCs) can be obtained from pulp tissue inside the teeth. Dental pulp stem cells are cells having a multi-differentiation ability such as mesenchymal stem cells (MSC), which can be differentiated into bone tissue, blood vessels, dental pulp connective tissues, and nerves in addition to dentin that forms teeth.

Meanwhile, teeth make dentin through odontogenesis in odontoblast. Dentin is one of the highly calcified hard tissues that form teeth together with enamel and cementum. Dentin is formed by inducing mineralization of the surrounding matrix due to signal molecules and proteins that are released from the odontoblast precursor cells. However, if the tissues are damaged due to tooth decay or trauma, it is very difficult to regenerate. Therefore, the current dental treatment is based on filling the teeth with dental materials having properties similar to teeth hard tissues. Thus, there is a need to study the optimal differentiation conditions for obtaining an odontoblast from a dental pulp stem cell, which can especially differentiate into only dentin.

There are many known results suggesting that 10 different cytokines belonging to the TGF-β family are likely to be involved in the process of inducing differentiation from a dental pulp stem cell into an odontoblast. But there is no clearly known mechanism. For these reasons, the only one factor is currently used, which is BMP2, which is known as a bone differentiation promoting factor for the regeneration of injured teeth and surrounding tissues in clinical and pre-clinical experiments.

BMPs belong to the TGF-β family, which are known to play a critical role in the regeneration process. TGF-β family has FGF-2 and TGF±-1 in addition to BMP, and they are known to participate in teeth and bone regeneration. However, the main differentiation factors and efficient differentiation conditions have not yet been established. In other words, the key differentiation factors and effective differentiation conditions for inducing a human dental pulp stem cell that has been primarily cultured from a dental pulp tissue in human teeth, into an odontoblast that can be efficiently differentiated into dentin have not yet been established. Thus, it is necessary to study the efficient differentiation of a dental pulp stem cell into an odontoblast capable of differentiating into dentin.

Although the dental pulp stem cell is effectively differentiated into odontoblast, it has been difficult to isolate and purify the odontoblast. Currently, 2-3 specific protein types, which are specific for cytoplasmic or extracellular matrix have been found to be a specific marker for odontoblast. However, it is difficult to effectively isolate and purify the odontoblast using them. Thus, it is difficult to use the odontoblast for tissue regeneration and differentiation. Therefore, there is a need for studies on the cell surface expression antigens that can effectively isolate and purify the odontoblast, and further, there is a need for studies to isolate the odontoblast using this.

DISCLOSURE

Technical Problem

Accordingly, the present inventors have studied the optimum conditions for differentiating a dental pulp stem cell into an odontoblast which may differentiate into dentin. As a result, they have found that a bone morphogenetic protein 2 (BMP2) and bone morphogenetic protein 4 (BMP4) are used to efficiently differentiate into an odontoblast, thereby completing the present invention.

Further, while the present inventors have continued their research to effectively isolate and purify induced to be differentiated odontoblast, they identified the antibody specifically binds to the surface of odontoblast and confirmed that the antibody makes the odontoblast to be effectively isolated and purified, thereby completing the present invention.

Accordingly, an object of the present invention is to provide a composition for inducing the differentiation of a dental pulp stem cell into an odontoblast, the composition including bone morphogenetic protein 2 (BMP2) and bone morphogenetic protein 4 (BMP4).

Another object of the present invention is to provide a method for inducing the differentiation of a dental pulp stem cell into an odontoblast, the method including treating the dental pulp stem cell with bone morphogenetic protein 2 (BMP2) and bone morphogenetic protein 4 (BMP4).

Still another object of the present invention is to provide a kit for inducing the differentiation of a dental pulp stem cell into an odontoblast, the kit including bone morphogenetic protein 2 (BMP2) and bone morphogenetic protein 4 (BMP4).

Further, an object of the present invention is to provide a total of 12 kinds of odontoblast-specific IgG monoclonal antibodies or a total of 15 kinds of odontoblast-specific IgM monoclonal antibodies and a composition, kit and method for identifying the differentiated odontoblast using the same and isolating the odontoblast.

Further, another object of the present invention is to provide a composition, kit and method for screening a differentiation-promoting substance that promotes the differentiation of undifferentiated dental pulp stem cell into an odontoblast.

Technical Solution

In order to achieve the objects, the present invention provides a composition for inducing the differentiation of a dental pulp stem cell into an odontoblast, the composition including bone morphogenetic protein 2 (BMP2) and bone morphogenetic protein 4 (BMP4).

Further, the present invention provides a method for inducing the differentiation of a dental pulp stem cell into an odontoblast, the method including treating the dental pulp stem cell with bone morphogenetic protein 2 (BMP2) and bone morphogenetic protein 4 (BMP4).

Further, the present invention provides a kit for inducing the differentiation of a dental pulp stem cell into an odontoblast, the kit including bone morphogenetic protein 2 (BMP2) and bone morphogenetic protein 4 (BMP4).

Further, the present invention provides a total of 12 kinds of odontoblast-specific IgG monoclonal antibodies.

Further, the present invention provides a hybridoma cell line producing the 12 kinds of odontoblast-specific IgG monoclonal antibodies.

Further, the present invention provides a composition and a kit for identifying the differentiated odontoblast, the composition and kit including the 12 kinds of odontoblast-specific IgG monoclonal antibodies.

Further, the present invention provides a method for identifying the differentiated odontoblast, the method including treating a sample with the 12 kinds of odontoblast-specific IgG monoclonal antibodies.

Further, the present invention provides a composition and a kit for isolating an odontoblast, the composition and kit including the 12 kinds of odontoblast-specific IgG monoclonal antibodies.

Further, the present invention provides a method for isolating an odontoblast, the method including a) treating a sample with the 12 kinds of odontoblast-specific IgG monoclonal antibodies and b) isolating the antibody combined with the odontoblast.

Further, the present invention provides a composition and a kit for screening a differentiation-promoting substance that promotes differentiation of an undifferentiated dental pulp stem cell into an odontoblast, the composition and the kit including the 12 kinds of odontoblast-specific IgG monoclonal antibodies.

Further, the present invention provides a method for screening a substance which differentiates an undifferentiated dental pulp stem cell into an odontoblast, the method including a) treating the undifferentiated dental pulp stem cell with the 12 kinds of odontoblast-specific IgG monoclonal antibodies, b) treating the undifferentiated dental pulp stem cell with a candidate substance, and c) treating the sample of b) step with 12 kinds of odontoblast-specific IgG monoclonal antibodies and comparing a binding reaction of a) step.

Further, the present invention provides a total of 15 odontoblast-specific IgM monoclonal antibodies.

Further, the present invention provides a hybridoma cell line producing the 15 kinds of odontoblast-specific IgM monoclonal antibodies.

Further, the present invention provides a composition and a kit for identifying the differentiated odontoblast, the composition and kit including the 15 kinds of odontoblast-specific IgM monoclonal antibodies.

Further, the present invention provides a method for identifying the differentiated odontoblast, the method including treating a sample with the 15 kinds of odontoblast-specific IgM monoclonal antibodies.

Further, the present invention provides a composition and a kit for isolating an odontoblast, the composition and kit including the 15 kinds of odontoblast-specific IgM monoclonal antibodies.

Further, the present invention provides a method for isolating an odontoblast, the method including a) treating a sample with the 15 kinds of odontoblast-specific IgM monoclonal antibodies and b) isolating the antibody combined with odontoblast.

Further, the present invention provides a composition and a kit for screening a differentiation-promoting substance that promotes differentiation of an undifferentiated dental pulp stem cell into an odontoblast, the composition and the kit including the 15 kinds of odontoblast-specific IgM monoclonal antibodies.

Further, the present invention provides a method for screening a substance which differentiates an undifferentiated dental pulp stem cell into an odontoblast, the method including a) treating the undifferentiated dental pulp stem cell with the 15 kinds of odontoblast-specific IgM monoclonal antibodies, b) treating the undifferentiated dental pulp stem cell with a candidate substance, and c) treating the sample of b) step with the 15 kinds of odontoblast-specific IgM monoclonal antibodies and comparing a binding reaction of a) step.

Advantageous Effects

According to the present invention, BMP2 and BMP4 are optimally combined to significantly increase the differentiation efficiency of dental pulp stem cells into odontoblasts, to induce the mineralization of the matrix, and to improve the differentiation ability of odontoblasts into dentin. Therefore, it can be used for a composition or kit for inducing the differentiation of dental pulp stem cells into odontoblasts so that it is possible to regenerate dentin to restore the damage of dental pulp and dentin. Further, IgG or IgM monoclonal antibody specifically binding to the surface of odontoblasts according to the present invention is used to effectively isolate and purify odontoblasts, which are useful for tissue regeneration and differentiation, and the IgG or IgM monoclonal antibody is useful for screening substances that efficiently promote differentiation of dental pulp stem cells into odontoblasts.

DESCRIPTION OF DRAWINGS

FIG. 1 is a view of illustrating the results of qRT-PCR for the gene expression levels in human-derived dental pulp stem cells treated with a cytokine.

FIG. 2 is a view of illustrating the results of qRT-PCR for the gene expression levels in human dental pulp stem cells treated with BMP2 and BMP4.

FIG. 3 is a view of illustrating the results of qRT-PCR for the gene expression levels in human dental pulp stem cells treated with BMP2 100 ng/ml and BMP4 10 ng/ml.

FIG. 4 is a view of illustrating the results of observing the morphology of cells after treatment dental pulp stem cells with BMP2 and BMP4.

FIG. 5 is a view of illustrating the results of observing the morphology and differentiation level of the cells at 0, 7th and 14th day after treatment dental pulp stem cells with BMP2 and BMP4 and then treatment of a differentiation inducer for mineralization.

FIG. 6 is a view of illustrating the quantitative results of observing the morphology and differentiation level of the cells at 0, 7th and 14th day after treatment dental pulp stem cells with BMP2 and BMP4 and then treatment of a differentiation inducer for mineralization.

FIG. 7 is a view of illustrating the results of confirming ALP activity in dental pulp cells and differentiated odontoblasts.

FIG. 8 is a view of illustrating the difference in marker expression of odontoblasts and hDPSCs differentiated by treatment with rhBMP2 and rhBMP4.

FIG. 9 is a schematic view of illustrating a method of preparing an odontoblast-specific antibody according to the present invention.

FIG. 10 is a view of illustrating sequence information of an odontoblast-specific IgG type antibody.

FIG. 11 is a view of illustrating the results of confirming the dental pulp tissue and odontoblast binding ability and binding positions of OD40, OD46, OD82B, OD142B, OD142D, OD149A, OD218A, OD218B, OD228, OD238, OD243A, and OD256 of the present invention.

FIG. 12 is a view of illustrating sequence information of odontoblast-specific IgM type antibodies.

BEST MODE

Hereinafter, the present invention is described in detail.

The present invention provides a composition for the differentiation of a dental pulp stem cell into an odontoblast, the composition including bone morphogenetic protein 2 (BMP2) and bone morphogenetic protein 4 (BMP4).

An odontoblast contacts dentin and is a columnar cell that forms dentin, which functions to directly make dentin which is the main component of teeth. This cell itself is one constituent of pulp tissues positioned inside the dentin and exists to be arranged in the wall of the pulp cavity inside the teeth. Dentin occupies most of the teeth, which is formed from odontoblasts. Dentin is an important component of teeth, and it constitutes most of the dental crown and root. After the eruption of the teeth, dentin functions to protect the pulp by forming secondary dentin in response to external stimuli.

In the present invention, dental pulp stem cells are a type of dental origin mesenchymal stem cells. The dental origin mesenchymal stem cells refer to (a portion of) stem cells affected by dental origin epithelial cells and are the mesodermal origin, which mean stem cells distributed in the dental pulp inside teeth and surrounding tissue of the teeth. For example, there are a dental pulp stem cell (DPSC), a stem cell from exfoliated deciduous teeth (SHED), a periodontal ligament stem cell (PDLSC), a stem cell from the apical papilla (SCAP), and a dental follicle precursor cell (DFPC).

In the present invention, dental pulp stem cells may be cells derived from an animal, preferably a mammal, more preferably a human.

Dental pulp stem cells of the present invention may be autologous, allogenic or xenogenic cells.

Dental pulp stem cells are present in the dental pulp inside teeth and in the tissues around the teeth, and the process of isolating and culturing them is well known in the art.

Treatment of bone morphogenetic protein 2 (BMP2) and bone morphogenetic protein 4 (BMP4) in the present invention significantly increases the differentiation efficiency of dental pulp stem cells into odontoblasts, induces mineralization of the matrix, and improves the differentiation ability into dentin. Accordingly, they may be used for a composition or kit for differentiation of dental pulp stem cells into odontoblasts, and they may regenerate dentin, thereby having effects of restoring damage to dental pulp and dentin.

Preferably, the weight ratio of BMP2 and BMP4 contained in the composition in the present invention is 10-20:1 more preferably 10:1, but is not limited thereto.

The composition of the present invention may include medium. The medium of the present invention includes all conventional media used in the art, which are suitable for culturing cells. Medium and culture conditions can be selected depending on the type of cells. The medium used for the culture is preferably a cell culture minimum medium (CCMM), which generally includes a carbon source, a nitrogen source, and a trace element component. For example, the cell culture minimum medium may include Dulbecco's Modified Eagle's Medium (DMEM), Minimal Essential Medium (MEM), Basal Medium Eagle (BME), RPMI 1640, F-10, F-12, α Minimal Essential Medium (αMEM), Glasgow's Minimal Essential Medium (GMEM), Iscove's Modified Dulbecco's Medium, and the like, but is not limited thereto. The medium may include antibiotics such as penicillin, streptomycin, and gentamicin.

The composition of the present invention may further include at least one conventionally known differentiation inducing substance into an odontoblast in addition to BMP2 and BMP4, such as fibroblast growth factor 2 (FGF2) or transforming growth factor β (TGFβ).

Further, the present invention provides a method for differentiation of dental pulp stem cells into odontoblasts, the method including treating dental pulp stem cells into odontoblasts with bone morphogenetic protein 2 (BMP2) and bone morphogenetic protein 4 (BMP4).

Odontoblasts differentiated in vitro may be isolated according to the method of differentiation of the present invention and then be used themselves, or they may be isolated by a method of isolation using a flow cytometer or the like and then be used as an active ingredient of a cell therapeutic agent or a pharmaceutical composition for regenerating the teeth.

The term "cell therapeutic agent" refers to a drug used for the purpose of treatment, diagnosis and prevention by a series of methods such as growing or selecting a living autologous, allogenic or xenogenic cell in vitro or changing biological characteristics of cells through another method so as to restore the functions of cells and tissues.

The dentin or dental pulp tissue regeneration effect of a cell therapeutic agent or a pharmaceutical composition according to the present invention allows the treatment of various dental pulp diseases. The dental pulp is a soft connective tissue that fills the dental pulp cavity inside the teeth, in which nerves and blood vessels are abundantly distributed. Dental pulp disease refers to a lesion in the dental pulp tissue up to the surface of the dentin. When physiochemical or bacterial stimuli are applied to a dental pulp, the blood vessels of the dental pulp are enlarged at first to show hyperemia (dental pulp hyperemia). If these stimuli continue, the dental pulp has inflammation (pulpitis). There is a difference in the degree of inflammation according to the intensity of stimulation and the presence or absence of bacterial infection. When the inflammation occurs due to the anatomical characteristics in which the pulp is surrounded by hard dentin, the circulatory disorder is likely to occur, and if left as it is, the dental pulp is prone to necrosis. Causes of dental pulp disease are very diverse, but most cases are caused by bacterial infections due to tooth decay and infection inside the dental pulp through the perforation, fractures and cracks of the teeth and paradental cyst. The dental pulp disease can also be caused by trauma, abrasion, tooth cracking, heat and friction from dental instruments during treatment and the like. Pulpitis caused by bacterial infection may be extended to periapical disease and periodontal disease.

The scope of the present invention includes the dental pulp diseases that exhibit these various causes and symptoms. Examples of dental pulp diseases include, but are not limited to, dentin hypersensitivity, pulp hyperemia, pulpitis, pulp degeneration, necrosis and gangrene of pulp.

Dental pulp stem cells can be treated with BMP2 and BMP4 of the present invention for preferably 5 days to 20 days, more preferably 7 days to 14 days, to promote differentiation into odontoblasts.

BMP2 and BMP4 of the present invention can be used by treating them directly at the lesion. It also affects the differentiation of endogenous dental pulp stem cells in patients, thereby having effects in the dental pulp or dentin regeneration treatment.

Further, the present invention provides a kit for the differentiation of a dental pulp stem cell into an odontoblast, the kit including bone morphogenetic protein 2 (BMP2) and bone morphogenetic protein 4 (BMP4).

The kit is not limited thereto and may include other reagents or devices. For example, the kit may include a culture plate for culturing a target cell to induce differentiation into an odontoblast, or a reagent (for example, alizarin red, etc.) capable of evaluating the state of the differentiation into an odontoblast, and may include dental pulp stem cells to be cultured.

The form of the kit according to the present invention may be provided by a single container containing additives for differentiation-inducing medium or BMP2 and BMP4 or a cytokine, phospholipid, or basal medium and other reagents in appropriate dosages and/or forms or may be provided by different containers, respectively.

The kit according to the present invention may include instructions describing the order in which the method according to the present invention is carried out.

Further, the present invention provides an odontoblast-specific IgG or IgM monoclonal antibody.

The IgG or IgM monoclonal antibody according to the present invention can bind specifically to odontoblasts differentiated from human dental pulp stem cells, so that the antibody may be useful to isolate and purify odontoblasts.

The present invention provides an odontoblast-specific IgG monoclonal antibody selected from the group consisting of a) an odontoblast-specific OD40 IgG antibody including a light chain variable region including a light chain CDR1 represented by SEQ ID NO: 1, a light chain CDR2 represented by SEQ ID NO: 2 and a light chain CDR3 represented by SEQ ID NO: 3 and a heavy chain variable region including a heavy chain CDR1 represented by SEQ ID NO: 4, a heavy chain CDR2 represented by SEQ ID NO: 5 and a heavy chain CDR3 represented by SEQ ID NO: 6, b) an odontoblast-specific OD46 IgG antibody including a light chain variable region including a light chain CDR1 represented by SEQ ID NO: 7, a light chain CDR2 represented by SEQ ID NO: 8 and a light chain CDR3 represented by SEQ ID NO: 9 and a heavy chain variable region including a heavy chain CDR1 represented by SEQ ID NO: 10, a heavy chain CDR2 represented by SEQ ID NO: 11 and a heavy chain CDR3 represented by SEQ ID NO: 12, c) an odontoblast-specific OD82B IgG antibody including a light chain variable region including a light chain CDR1 represented by SEQ ID NO: 13, a light chain CDR2 represented by SEQ ID NO: 14 and a light chain CDR3 represented by SEQ ID NO: 15 and a heavy chain variable region including a heavy chain CDR1 represented by SEQ ID NO: 16, a heavy chain CDR2 represented by SEQ ID NO: 17 and a heavy chain CDR3 represented by SEQ ID NO: 18, d) an odontoblast-specific OD142B IgG antibody including a light chain variable region including a light chain CDR1 represented by SEQ ID NO: 19, a light chain CDR2 represented by SEQ ID NO: 20 and a light chain CDR3 represented by SEQ ID NO: 21 and a heavy chain variable region including a heavy chain CDR1 represented by SEQ ID NO: 22, a heavy chain CDR2 represented by SEQ ID NO: 23 and a heavy chain CDR3 represented by SEQ ID NO: 24, e) an odontoblast-specific OD142D IgG antibody including a light chain variable region including a light chain CDR1 represented by SEQ ID NO: 25, a light chain CDR2 represented by SEQ ID NO: 26 and a light chain CDR3 represented by SEQ ID NO: 27 and a heavy chain variable region including a heavy chain CDR1 represented by SEQ ID NO: 28, a heavy chain CDR2 represented by SEQ ID NO: 29 and a heavy chain CDR3 represented by SEQ ID NO: 30, f) an odontoblast-specific OD149A IgG antibody including a light chain variable region including a light chain CDR1 represented by SEQ ID NO: 31, a light chain CDR2 represented by SEQ ID NO: 32 and a light chain CDR3 represented by SEQ ID NO: 33 and a heavy chain variable region including a heavy chain CDR1 represented by SEQ ID NO: 34, a heavy chain CDR2 represented by SEQ ID NO: 35 and a heavy chain CDR3 represented by SEQ ID NO: 36, g) an odontoblast-specific OD218A IgG antibody including a light chain variable region including a light chain CDR1 represented by SEQ ID NO: 37, a light chain CDR2 represented by SEQ ID NO: 38 and a light chain CDR3 represented by SEQ ID NO: 39 and a heavy chain variable region including a heavy chain CDR1 represented by SEQ ID NO: 40, a heavy chain CDR2 represented by SEQ ID NO: 41 and a heavy chain CDR3 represented by SEQ ID NO: 42, h) an odontoblast-specific OD218B IgG antibody including a light chain variable region including a light chain CDR1 represented by SEQ ID NO: 43, a light chain CDR2 represented by SEQ ID NO: 44 and a light chain CDR3 represented by SEQ ID NO: 45 and a heavy chain variable region including a heavy chain CDR1 represented by SEQ ID NO: 46, a heavy chain CDR2 represented by SEQ ID NO: 47 and a heavy chain CDR3 represented by SEQ ID NO: 48, i) an odontoblast-specific OD228 IgG antibody including a light chain variable region including a light chain CDR1 represented by SEQ ID NO: 49, a light chain CDR2 represented by SEQ ID NO: 50 and a light chain CDR3 represented by SEQ ID NO: 51 and a heavy chain variable region including a heavy chain CDR1 represented by SEQ ID NO: 52, a heavy chain CDR2 represented by SEQ ID NO: 53 and a heavy chain CDR3 represented by SEQ ID NO: 54, j) an odontoblast-specific OD238 IgG antibody including a light chain variable region including a light chain CDR1 represented by SEQ ID NO: 55, a light chain CDR2 represented by SEQ ID NO: 56 and a light chain CDR3 represented by SEQ ID NO: 57 and a heavy chain variable region including a heavy chain CDR1 represented by SEQ ID NO: 58, a heavy chain CDR2 represented by SEQ ID NO: 59 and a heavy chain CDR3 represented by SEQ ID NO: 60, k) an odontoblast-specific OD243A IgG antibody including a light chain variable region including a light chain CDR1 represented by SEQ ID NO: 61, a light chain CDR2 represented by SEQ ID NO: 62 and a light chain CDR3 represented by SEQ ID NO: 63 and a heavy chain variable region including a heavy chain CDR1 represented by SEQ ID NO: 64, a heavy chain CDR2 represented by SEQ ID NO: 65 and a heavy chain CDR3 represented by SEQ ID NO: 66, and l) an odontoblast-specific OD256 IgG antibody including a light chain variable region including a light chain CDR1 represented by SEQ ID NO: 67, a light chain CDR2 represented by SEQ ID NO: 68 and a light chain CDR3 represented by SEQ ID NO: 69 and a heavy chain variable region including a heavy chain CDR1 represented by SEQ ID NO:

70, a heavy chain CDR2 represented by SEQ ID NO: 71 and a heavy chain CDR3 represented by SEQ ID NO: 72.

The "odontoblast-specific IgG monoclonal antibody" of the present invention is an antibody that binds to factors specifically expressing only on the surface of odontoblasts differentiated from the dental pulp stem cells, which refers to an antibody including light and heavy chain variable regions as defined above.

The antibodies of the present invention can be obtained by performing decoy immunization using differentiation-induced odontoblasts as immunogens, and monoclonal antibodies against molecules that express only on the surface of differentiated odontoblasts through the decoy immunization can be obtained.

The present invention provides a total of 12 kinds of IgG monoclonal antibodies obtained by the method described above, which are named as OD40, OD46, OD82B, OD142B, OD142D, OD149A, OD218A, OD218B, OD228, OD238, OD243A, and OD256, respectively, in the present invention.

In the present invention, IgG monoclonal antibodies include the light and heavy chain variable regions as follows.

The OD40 IgG antibody may include a light chain variable region including a light chain CDR1 represented by SEQ ID NO: 1, a light chain CDR2 represented by SEQ ID NO: 2 and a light chain CDR3 represented by SEQ ID NO: 3 and a heavy chain variable region including a heavy chain CDR1 represented by SEQ ID NO: 4, a heavy chain CDR2 represented by SEQ ID NO: 5 and a heavy chain CDR3 represented by SEQ ID NO: 6, and the OD40 IgG antibody may be preferably characterized by including a light chain variable region represented by SEQ ID NO: 73 and a heavy chain variable region represented by SEQ ID NO: 74.

The light chain variable region of the OD40 IgG antibody may be characterized by being encoded by a nucleotide sequence represented by SEQ ID NO: 97, and the heavy chain variable region thereof may be characterized by being encoded by a nucleotide sequence represented by SEQ ID NO: 98.

The OD46 IgG antibody may include a light chain variable region including a light chain CDR1 represented by SEQ ID NO: 7, a light chain CDR2 represented by SEQ ID NO: 8 and a light chain CDR3 represented by SEQ ID NO: 9 and a heavy chain variable region including a heavy chain CDR1 represented by SEQ ID NO: 10, a heavy chain CDR2 represented by SEQ ID NO: 11 and a heavy chain CDR3 represented by SEQ ID NO: 12, and the OD46 IgG antibody may be preferably characterized by including a light chain variable region represented by SEQ ID NO: 75 and a heavy chain variable region represented by SEQ ID NO: 76.

The light chain variable region of the OD46 IgG antibody may be characterized by being encoded by a nucleotide sequence represented by SEQ ID NO: 99, and the heavy chain variable region thereof may be characterized by being encoded by a nucleotide sequence represented by SEQ ID NO: 100.

The OD82 IgG antibody may include a light chain variable region including a light chain CDR1 represented by SEQ ID NO: 13, a light chain CDR2 represented by SEQ ID NO: 14 and a light chain CDR3 represented by SEQ ID NO: 15 and a heavy chain variable region including a heavy chain CDR1 represented by SEQ ID NO: 16, a heavy chain CDR2 represented by SEQ ID NO: 17 and a heavy chain CDR3 represented by SEQ ID NO: 18, and the OD82B IgG antibody may be preferably characterized by including a light chain variable region represented by SEQ ID NO: 77 and a heavy chain variable region represented by SEQ ID NO: 78.

The light chain variable region of the OD82 IgG antibody may be characterized by being encoded by a nucleotide sequence represented by SEQ ID NO: 101, and the heavy chain variable region thereof may be characterized by being encoded by a nucleotide sequence represented by SEQ ID NO: 102.

The OD142B IgG antibody may include a light chain variable region including a light chain CDR1 represented by SEQ ID NO: 19, a light chain CDR2 represented by SEQ ID NO: 20 and a light chain CDR3 represented by SEQ ID NO: 21 and a heavy chain variable region including a heavy chain CDR1 represented by SEQ ID NO: 22, a heavy chain CDR2 represented by SEQ ID NO: 23 and a heavy chain CDR3 represented by SEQ ID NO: 24, and the OD142B IgG antibody may be preferably characterized by including a light chain variable region represented by SEQ ID NO: 79 and a heavy chain variable region represented by SEQ ID NO: 80.

The light chain variable region of the OD142B IgG antibody may be characterized by being encoded by a nucleotide sequence represented by SEQ ID NO: 103, and the heavy chain variable region thereof may be characterized by being encoded by a nucleotide sequence represented by SEQ ID NO: 104

The OD142D IgG antibody may include a light chain variable region including a light chain CDR1 represented by SEQ ID NO: 25, a light chain CDR2 represented by SEQ ID NO: 26 and a light chain CDR3 represented by SEQ ID NO: 27 and a heavy chain variable region including a heavy chain CDR1 represented by SEQ ID NO: 28, a heavy chain CDR2 represented by SEQ ID NO: 29 and a heavy chain CDR3 represented by SEQ ID NO: 30, and the OD142D IgG antibody may be preferably characterized by including a light chain variable region represented by SEQ ID NO: 81 and a heavy chain variable region represented by SEQ ID NO: 82.

The light chain variable region of the OD142D IgG antibody may be characterized by being encoded by a nucleotide sequence represented by SEQ ID NO: 105, and the heavy chain variable region thereof may be characterized by being encoded by a nucleotide sequence represented by SEQ ID NO: 106.

The OD149A IgG antibody may include a light chain variable region including a light chain CDR1 represented by SEQ ID NO: 31, a light chain CDR2 represented by SEQ ID NO: 32 and a light chain CDR3 represented by SEQ ID NO: 33 and a heavy chain variable region including a heavy chain CDR1 represented by SEQ ID NO: 34, a heavy chain CDR2 represented by SEQ ID NO: 35 and a heavy chain CDR3 represented by SEQ ID NO: 36, and the OD149A IgG antibody may be preferably characterized by including a light chain variable region represented by SEQ ID NO: 83 and a heavy chain variable region represented by SEQ ID NO: 84.

The light chain variable region of the OD149A IgG antibody may be characterized by being encoded by a nucleotide sequence represented by SEQ ID NO: 107, and the heavy chain variable region thereof may be characterized by being encoded by a nucleotide sequence represented by SEQ ID NO: 108.

The OD218A IgG antibody may include a light chain variable region including a light chain CDR1 represented by SEQ ID NO: 37, a light chain CDR2 represented by SEQ ID NO: 38 and a light chain CDR3 represented by SEQ ID NO:

39 and a heavy chain variable region including a heavy chain CDR1 represented by SEQ ID NO: 40, a heavy chain CDR2 represented by SEQ ID NO: 41 and a heavy chain CDR3 represented by SEQ ID NO: 42, and the OD218A IgG antibody may be preferably characterized by including a light chain variable region represented by SEQ ID NO: 85 and a heavy chain variable region represented by SEQ ID NO: 86.

The light chain variable region of the OD218A IgG antibody may be characterized by being encoded by a nucleotide sequence represented by SEQ ID NO: 109, and the heavy chain variable region thereof may be characterized by being encoded by a nucleotide sequence represented by SEQ ID NO: 110.

The OD218B IgG antibody may include a light chain variable region including a light chain CDR1 represented by SEQ ID NO: 43, a light chain CDR2 represented by SEQ ID NO: 44 and a light chain CDR3 represented by SEQ ID NO: 45 and a heavy chain variable region including a heavy chain CDR1 represented by SEQ ID NO: 46, a heavy chain CDR2 represented by SEQ ID NO: 47 and a heavy chain CDR3 represented by SEQ ID NO: 48, and the OD218B IgG antibody may be preferably characterized by including a light chain variable region represented by SEQ ID NO: 87 and a heavy chain variable region represented by SEQ ID NO: 88.

The light chain variable region of the OD218B IgG antibody may be characterized by being encoded by a nucleotide sequence represented by SEQ ID NO: 111, and the heavy chain variable region thereof may be characterized by being encoded by a nucleotide sequence represented by SEQ ID NO: 112.

The OD228 IgG antibody may include a light chain variable region including a light chain CDR1 represented by SEQ ID NO: 49, a light chain CDR2 represented by SEQ ID NO: 50 and a light chain CDR3 represented by SEQ ID NO: 51 and a heavy chain variable region including a heavy chain CDR1 represented by SEQ ID NO: 52, a heavy chain CDR2 represented by SEQ ID NO: 53 and a heavy chain CDR3 represented by SEQ ID NO: 54, and the OD228 IgG antibody may be preferably characterized by including a light chain variable region represented by SEQ ID NO: 89 and a heavy chain variable region represented by SEQ ID NO: 90.

The light chain variable region of the OD228 IgG antibody may be characterized by being encoded by a nucleotide sequence represented by SEQ ID NO: 113, and the heavy chain variable region thereof may be characterized by being encoded by a nucleotide sequence represented by SEQ ID NO: 114.

The OD238 IgG antibody may include a light chain variable region including a light chain CDR1 represented by SEQ ID NO: 55, a light chain CDR2 represented by SEQ ID NO: 56 and a light chain CDR3 represented by SEQ ID NO: 57 and a heavy chain variable region including a heavy chain CDR1 represented by SEQ ID NO: 58, a heavy chain CDR2 represented by SEQ ID NO: 59 and a heavy chain CDR3 represented by SEQ ID NO: 60, and the OD238 IgG antibody may be preferably characterized by including a light chain variable region represented by SEQ ID NO: 91 and a heavy chain variable region represented by SEQ ID NO: 92.

The light chain variable region of the OD238 IgG antibody may be characterized by being encoded by a nucleotide sequence represented by SEQ ID NO: 115, and the heavy chain variable region thereof may be characterized by being encoded by a nucleotide sequence represented by SEQ ID NO: 116.

The OD243A IgG antibody may include a light chain variable region including a light chain CDR1 represented by SEQ ID NO: 61, a light chain CDR2 represented by SEQ ID NO: 62 and a light chain CDR3 represented by SEQ ID NO: 63 and a heavy chain variable region including a heavy chain CDR1 represented by SEQ ID NO: 64, a heavy chain CDR2 represented by SEQ ID NO: 65 and a heavy chain CDR3 represented by SEQ ID NO: 66, and the OD243A IgG antibody may be preferably characterized by including a light chain variable region represented by SEQ ID NO: 93 and a heavy chain variable region represented by SEQ ID NO: 94.

The light chain variable region of the OD243A IgG antibody may be characterized by being encoded by a nucleotide sequence represented by SEQ ID NO: 117, and the heavy chain variable region thereof may be characterized by being encoded by a nucleotide sequence represented by SEQ ID NO: 118.

The OD256 IgG antibody may include a light chain variable region including a light chain CDR1 represented by SEQ ID NO: 67, a light chain CDR2 represented by SEQ ID NO: 68 and a light chain CDR3 represented by SEQ ID NO: 69 and a heavy chain variable region including a heavy chain CDR1 represented by SEQ ID NO: 70, a heavy chain CDR2 represented by SEQ ID NO: 71 and a heavy chain CDR3 represented by SEQ ID NO: 72, and the OD256 IgG antibody may be preferably characterized by including a light chain variable region represented by SEQ ID NO: 95 and a heavy chain variable region represented by SEQ ID NO: 96.

The light chain variable region of the OD256 IgG antibody may be characterized by being encoded by a nucleotide sequence represented by SEQ ID NO: 119, and the heavy chain variable region thereof may be characterized by being encoded by a nucleotide sequence represented by SEQ ID NO: 120.

Further, the present invention provides an odontoblast-specific IgM monoclonal antibody.

The IgM monoclonal antibody according to the present invention can bind specifically to odontoblasts differentiated from human dental pulp stem cells, so that the antibody may be useful to isolate and purify odontoblasts.

The present invention provides an odontoblast-specific IgM monoclonal antibody selected from the group consisting of a) an odontoblast-specific OD7 IgM antibody including a light chain variable region including a light chain CDR1 represented by SEQ ID NO: 121, a light chain CDR2 represented by SEQ ID NO: 122 and a light chain CDR3 represented by SEQ ID NO: 123 and a heavy chain variable region including a heavy chain CDR1 represented by SEQ ID NO: 124, a heavy chain CDR2 represented by SEQ ID NO: 125 and a heavy chain CDR3 represented by SEQ ID NO: 126, b) an odontoblast-specific OD111A IgM antibody including a light chain variable region including a light chain CDR1 represented by SEQ ID NO: 127, a light chain CDR2 represented by SEQ ID NO: 128 and a light chain CDR3 represented by SEQ ID NO: 129 and a heavy chain variable region including a heavy chain CDR1 represented by SEQ ID NO: 130, a heavy chain CDR2 represented by SEQ ID NO: 131 and a heavy chain CDR3 represented by SEQ ID NO: 132, c) an odontoblast-specific OD169B IgM antibody including a light chain variable region including a light chain CDR1 represented by SEQ ID NO: 133, a light chain CDR2 represented by SEQ ID NO: 134 and a light chain CDR3 represented by SEQ ID NO: 135 and a heavy chain variable region including a heavy chain CDR1 represented by SEQ ID NO: 136, a heavy chain CDR2 represented by SEQ ID NO: 137 and a heavy chain CDR3 represented by SEQ ID NO: 138, d) an odontoblast-specific OD184 IgM antibody including a light chain variable region including a light chain CDR1 represented by SEQ ID NO: 139, a light chain CDR2 represented by SEQ ID NO: 140 and a light chain CDR3 represented by SEQ ID NO: 141 and a heavy chain variable region including a heavy chain CDR1 represented by SEQ ID NO: 142, a heavy chain CDR2 represented by SEQ ID NO: 143 and a heavy chain CDR3 represented by SEQ ID NO: 144, e) an odontoblast-specific OD185 IgM antibody including a light chain variable region including a light chain CDR1 represented by SEQ ID NO: 145, a light chain CDR2 represented by SEQ ID NO: 146 and a light chain CDR3 represented by SEQ ID NO: 147 and a heavy chain variable region including a heavy chain CDR1 represented by SEQ ID NO: 148, a heavy chain CDR2 represented by SEQ ID NO: 149 and a heavy chain CDR3 represented by SEQ ID NO: 150, f) an odontoblast-specific OD196 IgM antibody including a light chain variable region including a light chain CDR1 represented by SEQ ID NO: 151, a light chain CDR2 represented by SEQ ID NO: 152 and a light chain CDR3 represented by SEQ ID NO: 153 and a heavy chain variable region including a heavy chain CDR1 represented by SEQ ID NO: 154, a heavy chain CDR2 represented by SEQ ID NO: 155 and a heavy chain CDR3 represented by SEQ ID NO: 156, g) an odontoblast-specific OD210A IgM antibody including a light chain variable region including a light chain CDR1 represented by SEQ ID NO: 157, a light chain CDR2 represented by SEQ ID NO: 158 and a light chain CDR3 represented by SEQ ID NO: 159 and a heavy chain variable region including a heavy chain CDR1 represented by SEQ ID NO: 160, a heavy chain CDR2 represented by SEQ ID NO: 161 and a heavy chain CDR3 represented by SEQ ID NO: 162, h) an odontoblast-specific OD225 IgM antibody including a light chain variable region including a light chain CDR1 represented by SEQ ID NO: 163, a light chain CDR2 represented by SEQ ID NO: 164 and a light chain CDR3 represented by SEQ ID NO: 165 and a heavy chain variable region including a heavy chain CDR1 represented by SEQ ID NO: 166, a heavy chain CDR2 represented by SEQ ID NO: 167 and a heavy chain CDR3 represented by SEQ ID NO: 168, i) an odontoblast-specific OD234 IgM antibody including a light chain variable region including a light chain CDR1 represented by SEQ ID NO: 169, a light chain CDR2 represented by SEQ ID NO: 170 and a light chain CDR3 represented by SEQ ID NO: 171 and a heavy chain variable region including a heavy chain CDR1 represented by SEQ ID NO: 172, a heavy chain CDR2 represented by SEQ ID NO: 173 and a heavy chain CDR3 represented by SEQ ID NO: 174, j) an odontoblast-specific OD241 IgM antibody including a light chain variable region including a light chain CDR1 represented by SEQ ID NO: 175, a light chain CDR2 represented by SEQ ID NO: 176 and a light chain CDR3 represented by SEQ ID NO: 177 and a heavy chain variable region including a heavy chain CDR1 represented by SEQ ID NO: 178, a heavy chain CDR2 represented by SEQ ID NO: 179 and a heavy chain CDR3 represented by SEQ ID NO: 180, k) an odontoblast-specific OD244 IgM antibody including a light chain variable region including a light chain CDR1 represented by SEQ ID NO: 181, a light chain CDR2 represented by SEQ ID NO: 182 and a light chain CDR3 represented by SEQ ID NO: 183 and a heavy chain variable region including a heavy chain CDR1 represented by SEQ ID NO: 184, a heavy chain CDR2 represented by SEQ ID NO: 185 and a heavy chain CDR3 represented by SEQ ID NO: 186, l) an odontoblast-specific OD270 IgM antibody including a light chain variable region including a light chain CDR1 represented by SEQ ID NO: 187, a light chain CDR2 represented by SEQ ID NO: 188 and a light chain CDR3 represented by SEQ ID NO: 189 and a heavy chain variable region including a heavy chain CDR1 represented by SEQ ID NO: 190, a heavy chain CDR2 represented by SEQ ID NO: 191 and a heavy chain CDR3 represented by SEQ ID NO: 192, m) an odontoblast-specific OD296 IgM antibody including a light chain variable region including a light chain CDR1 represented by SEQ ID NO: 193, a light chain CDR2 represented by SEQ ID NO: 194 and a light chain CDR3 represented by SEQ ID NO: 195 and a heavy chain variable region including a heavy chain CDR1 represented by SEQ ID NO: 196, a heavy chain CDR2 represented by SEQ ID NO: 197 and a heavy chain CDR3 represented by SEQ ID NO: 198, n) an odontoblast-specific OD298 IgM antibody including a light chain variable region including a light chain CDR1 represented by SEQ ID NO: 199, a light chain CDR2 represented by SEQ ID NO: 200 and a light chain CDR3 represented by SEQ ID NO: 201 and a heavy chain variable region including a heavy chain CDR1 represented by SEQ ID NO: 202, a heavy chain CDR2 represented by SEQ ID NO: 203 and a heavy chain CDR3 represented by SEQ ID NO: 204, and o) an odontoblast-specific OD340 IgM antibody including a light chain variable region including a light chain CDR1 represented by SEQ ID NO: 205, a light chain CDR2 represented by SEQ ID NO: 206 and a light chain CDR3 represented by SEQ ID NO: 207 and a heavy chain variable region including a heavy chain CDR1 represented by SEQ ID NO: 208, a heavy chain CDR2 represented by SEQ ID NO: 209 and a heavy chain CDR3 represented by SEQ ID NO: 210.

The “odontoblast-specific IgM monoclonal antibody” of the present invention is an antibody that binds to factors specifically expressing only on the surface of odontoblasts differentiated from the dental pulp stem cells, which refers to an antibody including light and heavy chain variable regions as defined above.

The antibodies of the present invention can be obtained by performing decoy immunization using differentiation-induced odontoblasts as immunogens, and monoclonal antibodies against molecules that express only on the surface of differentiated odontoblasts through the decoy immunization can be obtained.

The present invention provides a total of 15 IgM kinds of monoclonal antibodies obtained by the method described above, which are named as OD7, OD111A, OD169B, OD184, OD185, OD196, OD210A, OD225, OD234, OD241, OD244, OD270, OD296, OD298, and OD340, respectively, in the present invention.

In the present invention, IgM monoclonal antibodies include the light and heavy chain variable regions as follows.

The OD7 IgM antibody may include a light chain variable region including a light chain CDR1 represented by SEQ ID NO: 121, a light chain CDR2 represented by SEQ ID NO: 122 and a light chain CDR3 represented by SEQ ID NO: 123 and a heavy chain variable region including a heavy chain CDR1 represented by SEQ ID NO: 124, a heavy chain CDR2 represented by SEQ ID NO: 125 and a heavy chain CDR3 represented by SEQ ID NO: 126, and the OD7 IgM antibody may be preferably characterized by including a light chain variable region represented by SEQ ID NO: 211 and a heavy chain variable region represented by SEQ ID NO: 212.

The light chain variable region of the OD7 IgM antibody may be characterized by being encoded by a nucleotide sequence represented by SEQ ID NO: 241, and the heavy chain variable region thereof may be characterized by being encoded by a nucleotide sequence represented by SEQ ID NO: 242.

The OD111A IgM antibody may include a light chain variable region including a light chain CDR1 represented by SEQ ID NO: 127, a light chain CDR2 represented by SEQ ID NO: 128 and a light chain CDR3 represented by SEQ ID NO: 129 and a heavy chain variable region including a heavy chain CDR1 represented by SEQ ID NO: 130, a heavy chain CDR2 represented by SEQ ID NO: 131 and a heavy chain CDR3 represented by SEQ ID NO: 132, and the OD111A IgM antibody may be preferably characterized by including a light chain variable region represented by SEQ ID NO: 213, and a heavy chain variable region represented by SEQ ID NO: 214.

The light chain variable region of the OD111A IgM antibody may be characterized by being encoded by a nucleotide sequence represented by SEQ ID NO: 243, and the heavy chain variable region thereof may be characterized by being encoded by a nucleotide sequence represented by SEQ ID NO: 244.

The OD169B IgM antibody may include a light chain variable region including a light chain CDR1 represented by SEQ ID NO: 133, a light chain CDR2 represented by SEQ ID NO: 134 and a light chain CDR3 represented by SEQ ID NO: 135 and a heavy chain variable region including a heavy chain CDR1 represented by SEQ ID NO: 136, a heavy chain CDR2 represented by SEQ ID NO: 137 and a heavy chain CDR3 represented by SEQ ID NO: 138, and the OD169B IgM antibody may be preferably characterized by including a light chain variable region represented by SEQ ID NO: 215, and a heavy chain variable region represented by SEQ ID NO: 216.

The light chain variable region of the OD169B IgM antibody may be characterized by being encoded by a nucleotide sequence represented by SEQ ID NO: 245, and the heavy chain variable region thereof may be characterized by being encoded by a nucleotide sequence represented by SEQ ID NO: 246.

The OD184 IgM antibody may include a light chain variable region including a light chain CDR1 represented by SEQ ID NO: 139, a light chain CDR2 represented by SEQ ID NO: 140 and a light chain CDR3 represented by SEQ ID NO: 141 and a heavy chain variable region including a heavy chain CDR1 represented by SEQ ID NO: 142, a heavy chain CDR2 represented by SEQ ID NO: 143 and a heavy chain CDR3 represented by SEQ ID NO: 144, and the OD184 IgM antibody may be preferably characterized by including a light chain variable region represented by SEQ ID NO: 217, and a heavy chain variable region represented by SEQ ID NO: 218.

The light chain variable region of the OD184 IgM antibody may be characterized by being encoded by a nucleotide sequence represented by SEQ ID NO: 247, and the heavy chain variable region thereof may be characterized by being encoded by a nucleotide sequence represented by SEQ ID NO: 248.

The OD185 IgM antibody may include a light chain variable region including a light chain CDR1 represented by SEQ ID NO: 145, a light chain CDR2 represented by SEQ ID NO: 146 and a light chain CDR3 represented by SEQ ID NO: 147 and a heavy chain variable region including a heavy chain CDR1 represented by SEQ ID NO: 148, a heavy chain CDR2 represented by SEQ ID NO: 149 and a heavy chain CDR3 represented by SEQ ID NO: 150, and the OD185 IgM antibody may be preferably characterized by including a light chain variable region represented by SEQ ID NO: 219, and a heavy chain variable region represented by SEQ ID NO: 220.

The light chain variable region of the OD185 IgM antibody may be characterized by being encoded by a nucleotide sequence represented by SEQ ID NO: 249, and the heavy chain variable region thereof may be characterized by being encoded by a nucleotide sequence represented by SEQ ID NO: 250.

The OD196 IgM antibody may include a light chain variable region including a light chain CDR1 represented by SEQ ID NO: 151, a light chain CDR2 represented by SEQ ID NO: 152 and a light chain CDR3 represented by SEQ ID NO: 153 and a heavy chain variable region including a heavy chain CDR1 represented by SEQ ID NO: 154, a heavy chain CDR2 represented by SEQ ID NO: 155 and a heavy chain CDR3 represented by SEQ ID NO: 156, and the OD196 IgM antibody may be preferably characterized by including a light chain variable region represented by SEQ ID NO: 221 and a heavy chain variable region represented by SEQ ID NO: 222.

The light chain variable region of the OD196 IgM antibody may be characterized by being encoded by a nucleotide sequence represented by SEQ ID NO: 251, and the heavy chain variable region thereof may be characterized by being encoded by a nucleotide sequence represented by SEQ ID NO: 252.

The OD210A IgM antibody may include a light chain variable region including a light chain CDR1 represented by SEQ ID NO: 157, a light chain CDR2 represented by SEQ ID NO: 158 and a light chain CDR3 represented by SEQ ID NO: 159 and a heavy chain variable region including a heavy chain CDR1 represented by SEQ ID NO: 160, a heavy chain CDR2 represented by SEQ ID NO: 161 and a heavy chain CDR3 represented by SEQ ID NO: 162, and the OD210A IgM antibody may be preferably characterized by including a light chain variable region represented by SEQ ID NO: 223, and a heavy chain variable region represented by SEQ ID NO: 224.

The light chain variable region of the OD210A IgM antibody may be characterized by being encoded by a nucleotide sequence represented by SEQ ID NO: 253, and the heavy chain variable region thereof may be characterized by being encoded by a nucleotide sequence represented by SEQ ID NO: 254.

The OD225 IgM antibody may include a light chain variable region including a light chain CDR1 represented by SEQ ID NO: 163, a light chain CDR2 represented by SEQ ID NO: 164 and a light chain CDR3 represented by SEQ ID NO: 165 and a heavy chain variable region including a heavy chain CDR1 represented by SEQ ID NO: 166, a heavy chain CDR2 represented by SEQ ID NO: 167 and a heavy chain CDR3 represented by SEQ ID NO: 168, and the OD225 IgM antibody may be preferably characterized by including a light chain variable region represented by SEQ ID NO: 225, and a heavy chain variable region represented by SEQ ID NO: 226.

The light chain variable region of the OD225 IgM antibody may be characterized by being encoded by a nucleotide sequence represented by SEQ ID NO: 255, and the heavy chain variable region thereof may be characterized by being encoded by a nucleotide sequence represented by SEQ ID NO: 256.

The OD234 IgM antibody may include a light chain variable region including a light chain CDR1 represented by SEQ ID NO: 169, a light chain CDR2 represented by SEQ ID NO: 170 and a light chain CDR3 represented by SEQ ID NO: 171 and a heavy chain variable region including a heavy chain CDR1 represented by SEQ ID NO: 172, a heavy chain CDR2 represented by SEQ ID NO: 173 and a heavy chain CDR3 represented by SEQ ID NO: 174, and the OD234 IgM antibody may be preferably characterized by including a light chain variable region represented by SEQ ID NO: 227, and a heavy chain variable region represented by SEQ ID NO: 228.

The light chain variable region of the OD234 IgM antibody may be characterized by being encoded by a nucleotide sequence represented by SEQ ID NO: 257, and the heavy chain variable region thereof may be characterized by being encoded by a nucleotide sequence represented by SEQ ID NO: 258.

The OD241 IgM antibody may include a light chain variable region including a light chain CDR1 represented by SEQ ID NO: 175, a light chain CDR2 represented by SEQ ID NO: 176 and a light chain CDR3 represented by SEQ ID NO: 177 and a heavy chain variable region including a heavy chain CDR1 represented by SEQ ID NO: 178, a heavy chain CDR2 represented by SEQ ID NO: 179 and a heavy chain CDR3 represented by SEQ ID NO: 180, and the OD241 IgM antibody may be preferably characterized by including a light chain variable region represented by SEQ ID NO: 229, and a heavy chain variable region represented by SEQ ID NO: 230.

The light chain variable region of the OD241 IgM antibody may be characterized by being encoded by a nucleotide sequence represented by SEQ ID NO: 259, and the heavy chain variable region thereof may be characterized by being encoded by a nucleotide sequence represented by SEQ ID NO: 260.

The OD244 IgM antibody may include a light chain variable region including a light chain CDR1 represented by SEQ ID NO: 181, a light chain CDR2 represented by SEQ ID NO: 182 and a light chain CDR3 represented by SEQ ID NO: 183 and a heavy chain variable region including a heavy chain CDR1 represented by SEQ ID NO: 184, a heavy chain CDR2 represented by SEQ ID NO: 185 and a heavy chain CDR3 represented by SEQ ID NO: 186, and the OD244 IgM antibody may be preferably characterized by including a light chain variable region represented by SEQ ID NO: 231, and a heavy chain variable region represented by SEQ ID NO: 232.

The light chain variable region of the OD244 IgM antibody may be characterized by being encoded by a nucleotide sequence represented by SEQ ID NO: 261, and the heavy chain variable region thereof may be characterized by being encoded by a nucleotide sequence represented by SEQ ID NO: 262.

The OD270 IgM antibody may include a light chain variable region including a light chain CDR1 represented by SEQ ID NO: 187, a light chain CDR2 represented by SEQ ID NO: 188 and a light chain CDR3 represented by SEQ ID NO: 189 and a heavy chain variable region including a heavy chain CDR1 represented by SEQ ID NO: 190, a heavy chain CDR2 represented by SEQ ID NO: 191 and a heavy chain CDR3 represented by SEQ ID NO: 192, and the OD270 IgM antibody may be preferably characterized by including a light chain variable region represented by SEQ ID NO: 233, and a heavy chain variable region represented by SEQ ID NO: 234.

The light chain variable region of the OD270 IgM antibody may be characterized by being encoded by a nucleotide sequence represented by SEQ ID NO: 263, and the heavy chain variable region thereof may be characterized by being encoded by a nucleotide sequence represented by SEQ ID NO: 264.

The OD296 IgM antibody may include a light chain variable region including a light chain CDR1 represented by SEQ ID NO: 193, a light chain CDR2 represented by SEQ ID NO: 194 and a light chain CDR3 represented by SEQ ID NO: 195 and a heavy chain variable region including a heavy chain CDR1 represented by SEQ ID NO: 196, a heavy chain CDR2 represented by SEQ ID NO: 197 and a heavy chain CDR3 represented by SEQ ID NO: 198, and the OD296 IgM antibody may be preferably characterized by including a light chain variable region represented by SEQ ID NO: 235, and a heavy chain variable region represented by SEQ ID NO: 236.

The light chain variable region of the OD296 IgM antibody may be characterized by being encoded by a nucleotide sequence represented by SEQ ID NO: 265, and the heavy chain variable region thereof may be characterized by being encoded by a nucleotide sequence represented by SEQ ID NO: 266.

The OD298 IgM antibody may include a light chain variable region including a light chain CDR1 represented by SEQ ID NO: 199, a light chain CDR2 represented by SEQ ID NO: 200 and a light chain CDR3 represented by SEQ ID NO: 201 and a heavy chain variable region including a heavy chain CDR1 represented by SEQ ID NO: 202, a heavy chain CDR2 represented by SEQ ID NO: 203 and a heavy chain CDR3 represented by SEQ ID NO: 204, and the OD298 IgM antibody may be preferably characterized by including a light chain variable region represented by SEQ ID NO: 237, and a heavy chain variable region represented by SEQ ID NO: 238.

The light chain variable region of the OD298 IgM antibody may be characterized by being encoded by a nucleotide sequence represented by SEQ ID NO: 267, and the heavy chain variable region thereof may be characterized by being encoded by a nucleotide sequence represented by SEQ ID NO: 268.

The OD340 IgM antibody may include a light chain variable region including a light chain CDR1 represented by SEQ ID NO: 205, a light chain CDR2 represented by SEQ ID NO: 206 and a light chain CDR3 represented by SEQ ID NO: 207 and a heavy chain variable region including a heavy chain CDR1 represented by SEQ ID NO: 208, a heavy chain CDR2 represented by SEQ ID NO: 209 and a heavy chain CDR3 represented by SEQ ID NO: 210, and the OD340 IgM antibody may be preferably characterized by including a light chain variable region represented by SEQ ID NO: 239, and a heavy chain variable region represented by SEQ ID NO: 240.

The light chain variable region of the OD340 IgM antibody may be characterized by being encoded by a nucleotide sequence represented by SEQ ID NO: 269, and the heavy chain variable region antibody may be characterized by being encoded by a nucleotide sequence represented by SEQ ID NO: 270.

The antibody sequence of the present invention may be modified, for example, conservatively substituted according to the technical common sense of those skilled in the art as long as it can achieve the object of the present invention as specific-binding to odontoblasts and may include the polypeptide having 80% to 99% of sequence homology, preferably 85% to 99% of sequence homology, more preferably 90 to 99% of sequence homology with those obtained by the same.

The term "conservative substitution" refers to the replacement of one of one class of amino acids with another of the same class. Conservative substitutions do not alter the structure or function of the polypeptide or both. The classes of amino acids for conservative substitution include hydrophobic (e.g., Met, Ala, Val, and Leu), neutral hydrophilic (e.g. Cys, Ser, and Thr), acidic (e.g. Asp and Glu), basic (e.g., Asn, Gln, His, Lys, and Arg) substance, sterically hindered disrupter (e.g., Gly and Pro) and aromatic (e.g., Trp, Tyr, and Phe).

Further, as long as the IgG monoclonal antibodies of the present invention may achieve the object of the present invention as specific-binding to the surface of odontoblasts, they may be encoded by various sequences encoding light chain and heavy chain variable regions and CDR regions, respectively, represented by SEQ ID NOS: 1-96, in particular, may be preferably encoded by respective nucleotide sequences represented by SEQ ID NOS: 97-120, but is not limited thereto. Further, it may be encoded by a nucleotide sequence having 80% to 99% homology, 90% to 99% homology, 95% to 99% homology, which can encode the polypeptide equivalent thereto.

Further, as long as the IgM monoclonal antibodies of the present invention may achieve the object of the present invention as specific-binding to the surface of differentiated odontoblasts, they may be encoded by various sequences encoding light chain and heavy chain variable regions and CDR regions, respectively, represented by SEQ ID NOS: 120-240, in particular, may be preferably encoded by respective nucleotide sequences represented by SEQ ID NOS: 241-270, but is not limited thereto. Further, it may be encoded by a nucleotide sequence having 80% to 99% homology, 90% to 99% homology, 95% to 99% homology, which can encode the polypeptide equivalent thereto.

IgG or IgM monoclonal antibodies of the present invention may be characterized by specific-binding to differentiated odontoblasts. For example, the antibodies may specifically bind to cells in which dental pulp stem cells are differentiated into odontoblasts by treatment with bone morphogenetic protein 2 (BMP2) and bone morphogenetic protein 4 (BMP4).

Monoclonal antibodies provided in the present invention can be prepared by methods known in the art. For example, the antibody may be prepared by a chemical peptide synthesis method. The antibody may be prepared by amplification of a gene encoding the monoclonal antibody by a polymerase chain reaction (PCR) or synthetization of a gene encoding the monoclonal antibody by known methods, followed by cloning into an expression vector and expressing. The antibody may be prepared using a hybridoma cell line derived from a lymphocyte obtained by injecting an immunogen of the monoclonal antibody into an animal. In another example, the antibody may be prepared using a hybridoma cell line which is prepared using lymphocytes obtained from an animal after inoculating the animal with differentiated odontoblasts an immunogen.

Therefore, the present invention provides a hybridoma cell line that produces IgG or IgM monoclonal antibodies.

As used herein, the term "hybridoma cell line" refers to a cell resulting from the artificial fusion of two different cells, which means one cell or cell line into which two or more homogenous cells or heterogeneous cells prepared using a substance inducing cell fusion such as polyethylene glycol or a type of virus are fused to integrate different functions of different cells into one cell. In particular, a hybrid cell, which is prepared by the fusion of myeloma cells and a B cell which is a precursor cell responsible for producing antibodies among lymphocytes in the spleen or lymph node, produces monoclonal antibodies and is thus widely used in researches or clinical trials. In addition, lymphokines (physiologically active substance)-producing T cells and hybridomas which are tumor cells thereof are also practically used. The hybridoma cells of the present invention are preferably cells fused with myeloma cells and lymphocytes in which odontoblasts are immunized, and may include, without limitation, a hybridoma cell line capable of producing an IgG monoclonal antibody that specifically binds to the differentiated odontoblast.

Further, the present invention provides a composition and kit for identifying differentiated odontoblasts, the composition and kit including IgG or IgM monoclonal antibodies of the present invention.

An IgG or IgM monoclonal antibody of the present invention specifically binds to an odontoblast, preferably an odontoblast differentiated from a dental pulp stem cell, which can bind more effectively to the surface of odontoblast compared to the pre-differentiated dental pulp stem cell. Therefore, the IgG or IgM monoclonal antibody of the present invention is used to effectively identify and determine whether a precursor cell in the sample is differentiated into an odontoblast.

For identification and determination of such differentiation, the antibody of the present invention may be labeled with a distinguishable labeling substance. The labeling substance is not particularly limited as long as it binds to the monoclonal antibody so that the desired surface antigen is used to separate or isolate the differentiated odontoblast expressed. For example, the labeling substance may include, without limitation, a ligand, a bead, a radionuclide, an enzyme, a substrate, a cofactor, an inhibitor, a fluorescer, a chemiluminescent substance, a magnetic particle, a hapten, a dye, and the like. Further, the labeling substance may include, without limitation, ligands such as a biotin, an avidin, and a streptavidin, enzymes such as luciferase, peroxidase, and beta-galactosidase, and fluorescers such as fluorescein, 6-carboxyfluorescein, hexachloro-6-carboxyfluorescein, tetrachloro-6-carboxyfluorescein, VIC, JOE, 5-(2'-aminoethyl) aminonaphthalene-1-sulfonic acid, coumarin and derivatives thereof, cyanine-5, Lucifer yellow, Texas red, tetramethyl rhodamine, Yakima Yellow, Cal Fluor Red 610, coumarin and derivatives thereof.

Further, the present invention provides a method for identifying a differentiated odontoblast, the method including the step of treating a sample with the IgG or IgM monoclonal antibody.

According to the present invention method, it is easy to confirm whether or not the dental pulp stem cells have been differentiated into odontoblasts using the property of binding to a specific antigen expressed on the surface of odontoblast of IgG or IgM monoclonal antibody of the present invention.

For example, the IgG or IgM monoclonal antibody of the present invention may be labeled for detection, and when the dental pulp stem cell present in the sample is induced to differentiate into an odontoblast, through the marker detection of IgG or IgM monoclonal antibody bound to the odontoblast, the differentiated odontoblast can be identified. In this case, the method of the present invention can include the steps of a) treating the sample with an IgG or IgM monoclonal antibody, and b) detecting an IgG or IgM monoclonal antibody bound to the cells in the sample.

If the bound IgG or IgM monoclonal antibody detected in a sample containing cells before differentiated, such as a dental pulp stem cell, is compared with the bound IgG or IgM monoclonal antibody detected in the sample subjected to differentiation-induction, when the content of the bound IgG or IgM monoclonal antibody detected from the sample subjected to differentiation-induction increases, it can be confirmed the dental pulp stem cell is differentiated into the odontoblast, and the differentiated odontoblast is present in the sample.

Further, the present invention provides a composition and kit for isolating an odontoblast, the composition and kit including an IgG or IgM monoclonal antibody.

The IgG or IgM monoclonal antibody of the present invention may specifically detect the differentiated odontoblast. The property may be used to effectively isolate an odontoblast from a sample, for example, a sample which is mixed with the undifferentiated dental pulp stem cell.

Further, the present invention provides a method for isolating odontoblast, the method including: a) treating a sample with an IgG or IgM monoclonal antibody of the present invention; and b) isolating the antibody binding to the odontoblast.

The step of isolating the antibody binding to the odontoblast can be carried out using a method commonly used in the art. For example, flow cytometry, immunoprecipitation, magnetic activated cell sorting method, and chromatography may be used. As another example, flow cytometry using a composition labeled with a fluorescent substance, immunoprecipitation using a composition including a preparation combined with gold particles, magnetic separation using a composition combined with magnetic beads, a chromatography method using a column filled with beads combined with the preparation, and the like may be used.

Further, the present invention provides a composition and kit for screening a differentiation-promoting substance that promotes the differentiation of an undifferentiated dental pulp stem cell into an odontoblast, the composition and kit including the IgG or IgM monoclonal antibody of the present invention.

The IgG or IgM monoclonal antibody of the present invention binds specifically to the differentiated odontoblast, and thus the property may be used to compare the binding level before treating with the differentiation promoting candidate and the binding level after treating with the differentiation promoting candidate, thereby using for screening a differentiation-promoting substance that promotes the differentiation of an undifferentiated dental pulp stem cell into an odontoblast.

Therefore, the present invention provides a method for screening a substance which differentiates an undifferentiated dental pulp stem cell into an odontoblast, the method including a) treating the undifferentiated dental pulp stem cell with the IgG or IgM monoclonal antibody of the present invention, b) treating the undifferentiated dental pulp stem cell in a sample with a candidate substance, and c) treating the sample of b) step with the IgG or IgM monoclonal antibody of the present invention and comparing a binding reaction of a) step.

The kit used in the present invention may be an immunofluorescence kit including a substrate on which the formulation of the composition is fixed and a secondary antibody conjugated to a fluorescent substance and being specific to the IgG or IgM monoclonal antibody. As another example, the kit may be a chromatography kit including a bead combined with the formulation of the composition, a column into which the bead may be filled and a buffer for developing. As still another example, the kit may be a MACS kit including biotin combined with the formulation of the composition, a streptavidin combined with a magnetic bead and a magnetic generator.

Hereinafter, the present invention is in detail with reference to Examples. However, the following Examples are merely illustrative of the present invention, and the contents of the present invention are not limited by the following Examples.

MODES OF THE INVENTION

Example 1: Identification of Gene Expression by Treatment Human Dental Pulp Stem Cells (hDPSCs) with Cytokine To identify the conditions for differentiation of human dental pulp stem cells into odontoblasts, human dental pulp stem cells were treated with cytokines such as bone morphogenetic protein 2 (BMP2), bone morphogenetic protein 4 (BMP4), fibroblast growth factor 2 (FGF2), transforming growth factor β (TGFβ), or a combination thereof. The types and amounts of cytokines treated in this Example are shown in Table 1 below.

TABLE 1

| | Control | BMP2 | BMP4 | BMP2 + BMP4 | FGF2 | TGFβ | FGF + TGFβ |
|---|---|---|---|---|---|---|---|
| ng/ml | 0 | 100 | 100 | 100 + 100 | 50 | 5 | 50 + 5 |

As shown in Table 1, After treatment with a cytokine, qRT-PCR was performed to identify whether genes expressing odontoblasts were expressed.

The sequences of target genes and primers identified in the qRT-PCR experiment are shown in Table 2 below. Among them, bone sialoprotein (BSP) is a gene expressed in differentiated osteoblasts, odontoblasts, and cementoblasts. Runt-related transcription factor 2 (Runx2) is a gene expressed in osteoblasts, preodontoblasts and odontoblasts. Ostrerix is a gene expressed in osteoblasts.

TABLE 2

| Target gene | Forward primer | Reverse primer |
|---|---|---|
| Scleraxis | AGAAAGTTGAGCAAGGACC | CTGTCTGTACGTCCGTCT |
| Runx2 | GTCTCACTGCCTCTCACT | TACACACATCTCCTCCCTTC |
| hCOLα1 | GGAGGAGAGTCAGGAAGG | TCAGCAACACAGTTACACAA |
| Osteopontin | CTGTTGCCTGTCTCTAAACC | CACCATCATCAAATTCTCCT |
| Ostrerix | TTGACATGTACCCCTTTCTG | CAATACCCCTGATGAAGAGG |
| DMP-1 | GACTCTCAAGAAGACAGCAA | GACTCACTCACCACCTCT |
| BSP | TACCGAGCCTATGAAGATGA | CTTCCTGAGTTGAACTTCGA |
| DSPP | CAGTACAGGATGAGTTAAATGCCAGTG | CCATTCCCTTCTCCCTTGTGACC |
| GAPDH | GTATGACAACAGCCTCAAGAT | CCT TCCACGATACCAAAGTT |

The results of qRT-PCR are illustrated in FIG. 1.

As illustrated in FIG. 1, the result of analyzing the expression of dentin-forming marker gene indicated that their expression levels were the highest when dentin sialophosphoprotein (DSPP) and dentin matrix protein-1 (DMP-1) were treated with combination with BMP2 and BMP4. Meanwhile, the result of analyzing the expression of bone marker gene revealed that expression of Ostrerix, hCOLα1 (collagen-1) and Runx2 genes, which are significant osteoblast markers, was increased under the condition of treating with BMP4 only. The expression of BSP gene in differentiated osteoblast, odontoblast and cementoblast was increased when BMP2 and BMP4 were treated in combination.

Therefore, it was confirmed that the optimal condition for differentiating dental pulp stem cells into odontoblasts is the treatment with BMP2 and BMP4 at the same time.

Example 2: Determination of Optimal Condition for BMP2 and BMP4 Combination for Differentiation into Odontoblast The results of Example 1 confirmed that treating with BMP2 and BMP4 at the same time was efficient in order to differentiate human-derived dental pulp stem cells into odontoblasts. Further, in order to establish the optimal combination conditions of BMP2 and BMP4, human dental pulp stem cells were treated with various concentrations of BMP2 and BMP4 combinations as described in Table 3 below.

TABLE 3

| | | | | | |
|---|---|---|---|---|---|
| BMP2(ng/ml) | 0 | 10 | 10 | 100 | 100 |
| BMP4(ng/ml) | 0 | 10 | 100 | 10 | 100 |

After the treatment, the expression of the genes in dental pulp stem cells, which were described in Table 2, was confirmed by qRT-PCR, and the results are illustrated in FIG. 2.

As illustrated in FIG. 2, it was confirmed that the expression of Runx2, osteopontin, BSP, DMP1, and DSPP genes, which are odontoblast-related genes except for ligament progenitor markers such as hCOL1 and scleraxis genes, were significantly increased when treated with 100 ng/ml of BMP2 and 10 ng/ml of BMP4.

Further, the expression level of odontoblast gene was examined under the condition of treating with 100 ng/ml of BMP2 and 10 ng/ml of BMP4, and the results are illustrated in FIG. 3.

As illustrated in FIG. 3, it was confirmed that the expression of genes in odontoblasts treated with 100 ng/ml of BMP2 and 10 ng/ml of BMP4 was significantly higher than that of the control untreated.

Therefore, it was confirmed that the condition for treating with 100 ng/ml of BMP2 and 10 ng/ml of BMP4, that is, a condition in which a ratio of BMP2:BMP4 is 10:1, was the optimal condition for the differentiation into odontoblasts.

Example 3. Identification of Differentiation Efficiency Under Optimal Condition for Differentiation into Odontoblast The mineralization and bone differentiation degree thereof was measured to determine how high differentiation efficiency of the differentiated odontoblast was in the condition of the weight ratio of 10:1, which is the optimal combination ratio as confirmed in Example 2 above.

Specifically, the morphology of the cells was observed for 7 days in which dental pulp stem cells were treated with BMP2 and BMP4 at the same time as 10:1 and then differentiated into odontoblasts. The results are illustrated in FIG. 4.

As illustrated in FIG. 4, it was confirmed that there was no significant difference in terms of morphology during the differentiation of dental pulp stem cells into odontoblasts.

Thereafter, the cells were treated with a differentiation-inducing agent for mineralization and stood for 14 days. After the treatment, the cells were stained with Alizarin-red S (ARS) to observe the cell morphology and the differentiation level at $0^{th}$, $7^{th}$ and $14^{th}$ days after treating with the differentiation-inducing agent. The results are illustrated in FIG. 5. The level of differentiation is quantified, and the result is illustrated in FIG. 6.

As illustrated in FIGS. 5 and 6, it was confirmed that the mineralization was gradually increased in odontoblasts compared with the dental pulp stem cells for 14 days after treatment with the differentiation-inducing agent for mineralization, and the differentiation ability was significantly increased in the cells differentiated into odontoblasts.

Example 4. Identification of the Differentiation Ability of Differentiated Odontoblast into Bone and Dentin Alkaline phosphatase (ALP) activity assay was performed to determine the differentiation ability of odontoblasts into bone and dentin, which were differentiated under optimal conditions for differentiation into odontoblast. The results of the analysis are illustrated in FIG. 7.

As illustrated in FIG. 7, it was observed that the level of ALP activity in differentiated odontoblasts was significantly higher compared with one in dental pulp stem cells.

Therefore, it was confirmed that the differentiation ability of odontoblasts into dentin was increased compared to that of the dental pulp stem cells.

Example 5. Obtaining Odontoblast-Specific Monoclonal Antibodies

The wisdom teeth provided by adult patients (aged 20-27 years) approved by IRB's review at Dankook University Dental Hospital were used for the primary culture of human dental pulp stem cells (hDPSCs). Human dental pulp tissue was obtained by cutting the teeth and extracting the tissue contained therein. After finely cutting, they were treated with 3 mg/ml collagenase type I (Millipore) and 4 mg/ml dispase (Sigma-Aldrich) at 37° C. for 1 hour to isolate into single cells (Choi et al., 2015, Min et al., 2011). The isolated single cells were cultured in α-MEM (Hyclone) supplemented with 20% fetal bovine serum (FBS, Hyclone) and antibiotic (Lonza) in a 5% $CO_2$ incubator at 37° C. In order to differentiate human dental pulp-derived stem cells into odontoblasts, hDPSCs cultured in α-MEM supplemented with 10% FBS were treated simultaneously with 100 ng/ml rhBMP2 (Sino Biological) and 10 ng/ml rhBMP4 (Prospec) and further cultured for 7 days. It was confirmed that hDPSCs were effectively differentiated into odontoblasts because of the treatment of rhBMP2 and rhBMP4. Further, the odontoblasts differentiated by treatment with rhBMP2 and rhBMP4 showed a marker indicating significantly higher expression levels compared to hDPSCs. The results are illustrated in FIG. 8.

As illustrated in FIG. 8, it was confirmed that genes of Runx2, osteopontin, osterix, BSP, DMP1 and DSPP in odontoblasts treated with 100 ng/ml rBMP2 and 10 ng/ml rBMP4 were significantly highly expressed compared to those in hDPSCs.

Decoy immunization was performed using the obtained odontoblasts as an immunogen in order to obtain a monoclonal antibody against molecules expressing only on the surface of the differentiated odontoblast. hDPSCs not differentiated were used as negative control cells. More specifically, the cells cultured in the incubator were detached using an Enzyme Free Cell Dissociation Solution (Millipore). Then about $5\times10^5$ cells were suspended in 30 μl of PBS, and they were injected into the hind paw pad of 10 six-week-old Balb/c mice (DBL). Referring previously reported method (Yin et al., 1997), the negative control hDPSCs were injected on the right hind paw pad at 0, 3, 6, 9, 12, 15, 18, 21, and 24th days so as to induce immune reaction, and the differentiation-induced odontoblasts were injected on the left hind paw pad at 3, 6, 9, 12, 15, 18, 21, and 24th days so as to induce immune reaction. On the 24th day, lymph nodes were extracted from the left ham, and the extracted lymphocytes (lymphocytes immunized with odontoblasts, $8\times10^7$ cells/10 mice) were cell-fused with the myeloma cells (ATCC). Fused hybridoma cells were seeded in 96-well plates with DMEM medium supplemented with 20% FBS (Hyclone), HFCS (Roche) and HAT (Sigma-Aldrich) (Kohler and Milstein, 1975). The hybridoma culture media were collected, and ELISA and flow cytometry were used to verify whether antibodies are produced and bind to odontoblasts. FIG. 9 briefly illustrates the procedure for obtaining antibodies that bind to factors specifically expressing on the only surface of the differentiation-induced odontoblasts using the decoy immunization.

Example 6. Purification of Monoclonal Antibody

The monoclonal antibody prepared in Example 5 was purified using a column chromatography using a medium in which hybridomas were cultured. Protein G agarose (Incospharm) column was used to purify IgG type monoclonal antibody, and Protein L Agarose (Thermo) column was used to purify the IgM type monoclonal antibody. Agarose was washed with PBS after the medium was released. The IgG and IgM monoclonal antibodies bound were eluted with 100 mM glycine buffer (pH 2.8) and then immediately neutralized by adding 1 M Tris-HCl buffer (pH 9.0). After dialysis with PBS, the antibody concentration was determined.

6.1. Isotyping Analysis of Monoclonal Antibody

In order to determine the immuno-isotype of the purified monoclonal antibody, a 96-well plate was first coated with anti-mouse IgG1, IgG2a, IgG2b, IgG3, IgM, IgA, Igκ and Igλ, and then was blocked with PBS supplemented with 10% FBS. Medium in which each hybridoma was grown or purified monoclonal antibody was added thereto. Then, they were reacted for a specified period of time and then reacted with the secondary antibody. The secondary antibody was an antibody conjugated with horseradish peroxidase. The reaction was identified at a wavelength of 450 nm. The results are shown in Table 4.

TABLE 4

| Type | Heavy chain | | | | | | Light chain | |
|---|---|---|---|---|---|---|---|---|
| | IgG | | | | | | | |
| MAb | G1 | G2a | G2b | G3 | IgM | IgA | κ | λ |
| OD40 | + | − | − | − | − | − | + | − |
| OD46 | − | − | + | − | − | − | + | − |
| OD82B | + | | | | | | + | |
| OD142B | + | | | | | | + | |
| OD142D | + | | | | | | + | |
| OD149A | + | − | − | − | − | − | + | − |
| OD218A | + | − | − | − | − | − | + | − |
| OD218B | + | | | | | | + | |
| OD228 | + | − | − | − | − | − | + | − |
| OD238 | + | − | − | − | − | − | + | − |
| OD243A | + | | | | | | + | |
| OD256 | + | − | − | − | − | − | + | − |

As shown in Table 4, it was confirmed that 12 kinds of IgG-type antibodies such as OD40, OD46, OD82B, OD142B, OD142D, OD149A, OD218A, OD218B, OD228, OD238, OD243A, and OD256 were obtained finally.

6.2 Measurement of Antibody Binding Affinity by Flow Cytometry

Flow cytometry analysis was performed on the cell-antibody reaction so as to identify whether the antibody prepared in Example 5 binds better to the surface of odontoblasts among the surfaces of hDPSCs and odontoblasts. More specifically, Enzyme Free Cell Dissociation Solution (Millipore) was added thereto, and they were cultured for 10 minutes. Then, they were detached from the culture dish to be collected.

About $3\times10^4$ cells of hDPSCs and odontoblasts were resuspended in PBS supplemented with 1% BSA (GeneDEPOT), and then hybridoma culture medium or purified monoclonal antibodies were added thereto. Then, the cells were reacted on ice for 1 hour. After washing, FITC-conjugated anti-mouse IgG (1,100, Santa Cruz) or PE-conjugated anti-mouse IgM (1,100, Santa Cruz) was added as a secondary antibody, and they were reacted on ice for 1 hour. The degree of binding of antibody binding to the cell surface was analyzed by FACS Calibur™ (BD Biosciences). Antibody binding affinity was quantified using Cell Quest pro and WinMDI program. Cells that only reacted with the secondary antibody were used as a control group. It was confirmed that all of the 12 kinds of IgG type antibodies were bound to highly expressed antigens in odontoblasts than in hDPSCs, or bound to antigens expressed on only odontoblasts. These results indicate that the 12 kinds of monoclonal antibodies specifically bind to surface antigens specifically expressed in human odontoblast so that they can be used for purely isolating odontoblasts.

Example 7. Analysis of Antibody Sequence

In order to analyze the gene sequences of the antibodies obtained in Example 5, primers for amplifying the heavy chain and light chain variable region of the antibodies were synthesized according to the method disclosed in Wang et al., 2000 and the like. The sequences of the primers used are as follows. For other isotypes, suitable primers were synthesized to be used.

TABLE 5

| | Heavy chain |
|---|---|
| 5'MH1 | SAR GTN MAG CTG SAG SAG TC |
| 5'MH2 | SAR GTN MAG CTG SAG SAG TCW GG |
| IgA | 5'-GAT GGT GGG ATT TCT CGC AGA CTC-3' |
| IgE | 5'-TAA GGG GTA GAG CTG AGG GTT CCT G-3' |
| IgM | 5'-GAC ATT TGG GAA GGA CTG ACT CTC-3' |
| IgG1 | 5'-ATA GAC AGA TGG GGG TGT CGT TTT GGC-3' |
| IgG2a | 5'-CTT GAC CAG GCA TCC TAG AGT CA-3' |
| IgG2b | 5'-AGG GGC CAG TGG ATA GAC TGA TGG-3' |
| IgG3 | 5'-AGG GAC CAA GGG ATA GAC AGA TGG-3' |
| | **Light chain** |
| 5'MK | GAY ATT GTG MTS ACM CAR WCT MCA |
| 3'CK | GGA TAC AGT TGG TGC AGC ATC |
| Primer6 | GAC ATT GTG CTG ACC CAA TCT CCA GCT TCT |
| primer7 | GAC ATT CAG CTG ACC CAG TCT CCA |

The Easy-spin™ Total RNA Extraction kit (Intron) was used to collect hybridoma cells (up to $1\times10^6$ cells) and extract total RNA. The cDNA was synthesized at 45° C. for 30 minutes using Maxime RT-PCR PreMix Kit (Intron). RT-PCR was performed by 1 cycle at 94° C. for 5 minutes, 30 cycles at 94° C. for 1 minute, 45° C. for 1 minute, and 72° C. for 1 minute and a final cycle at 72° C. for 5 minutes. The amplified DNA fragment was cloned into pBluescript KS (+) vector, and its sequence was analyzed. The consensus domain of the antibody was analyzed according to Dr. Andrew C. R. Martin's Group database.

The CDR region is a site that recognizes and binds to a specific antigen. CDR1 and CDR2 are found in a variable region (V). For CDR3, a heavy chain includes a portion of V region, a diversity region (D) and a joining region (J), and light chain includes V, J regions. Sequence information of the IgG type antibody confirmed by analysis of sequences is illustrated in FIG. 10.

In addition, the nucleotide sequences encoding the light and heavy chains of these individual antibodies are represented by SEQ ID NOS: 97 to 120.

Example 8. Immunohistochemistry Assay

After massive purification of each monoclonal antibody, tissue immunohistochemistry was performed to analyze the location of the antigens bound to these monoclonal antibodies in the pulp tissue in human teeth. Extracted human pulp tissues were immersed and fixed in 4% paraformaldehyde (PFA). After washing with PBS, they were reacted in 30% sucrose for one day. The fixed tissue was prepared as a block using the OCT compound (SAKURA) and sectioned in a thickness of 10 μm. After washing with PBS, 0.3% $H_2O_2$ diluted in PBS was added to inhibit the endogenous peroxidase activity. The tissue fragments were reacted in blocking solution (0.1% PBST with serum, BSA, 0.1% tween 20 in PBS) for 1 hour at room temperature, and they were treated with the purified monoclonal antibodies at 4° C. for 16 hours. After washing with 0.1% PBST, they were treated with biotin-conjugated anti-mouse IgG. Then, the reaction proceeded at room temperature for one hour. Then, they were treated with VECTASTAIN® ABC Reagent at room temperature for 30 minutes. The degree of staining was then monitored while the DAB substrate was added. Cell nuclei in the tissue were stained with Harris hematoxylin. After dehydration, they were sealed with Eukitt quick-harder mounting medium (Sigma-Aldrich) and observed with an upright microscope (Nikon). The results are illustrated in FIG. 11. Biotin-conjugated anti-mouse IgG was used as a control.

As illustrated in FIG. 11, it was confirmed that the monoclonal antibody was stained in the odontoblast layer, which is the marginal portion of the dental pulp tissue. In particular, it was confirmed that OD82B stained nuclei of odontoblasts. In addition, it was confirmed that OD228 and OD256 stained the pulp core region where blood vessels in which dental pulp stem cells were located were located. On the other hand, when staining with biotin-conjugated anti-mouse IgG as a control, staining was not clearly observed in the odontoblast layer.

The above results indicated that the monoclonal antibodies prepared can be used to recognize and isolate surface markers specifically expressed in human odontoblast, which may then be used as various diagnostic antibodies.

Example 9. Obtaining Odontoblast-Specific IgM Monoclonal Antibody

The odontoblast-specific IgM monoclonal antibodies were obtained in the same manner as in Example 5. Specifically, decoy immunization was performed using the obtained odontoblasts as an immunogen in order to obtain a monoclonal antibody against molecules expressing only on the surface of the differentiated odontoblast. hDPSCs not differentiated were used as negative control cells. More specifically, the cells cultured in the incubator were detached using an Enzyme Free Cell Dissociation Solution (Millipore). Then about $5\times10^5$ cells were suspended in 30 μl of PBS, and they were injected on the hind paw pad of 10 six-week-old Balb/c mice (DBL). Referring the previously reported method (Yin et al., 1997), the negative control hDPSCs were injected on the right hind paw pad at 0, 3, 6, 9, 12, 15, 18, 21, and 24th days so as to induce immune reaction, and differentiation-induced odontoblasts were injected on the left hind paw pad at 3, 6, 9, 12, 15, 18, 21, and 24th days so as to induce immune reaction. On the 24th day, lymph nodes were extracted from the left ham, and the extracted lymphocytes (lymphocytes immunized with odontoblasts, $8\times10^7$ cells/10 mice) were cell-fused with the myeloma cells (ATCC). Fused hybridoma cells were seeded in 96-well plates with DMEM medium supplemented with 20% FBS (Hyclone), HFCS (Roche), and HAT (Sigma-Aldrich) (Kohler and Milstein, 1975). The hybridoma culture media were collected, and ELISA and flow cytometry were used to verify whether antibodies are produced and bind to odontoblasts. FIG. 9 briefly illustrates the procedure for obtaining antibodies that bind to factors specifically expressing on the only surface of the differentiation-induced odontoblasts using the decoy immunization.

Example 10. Purification of Monoclonal Antibody

The monoclonal antibody prepared in Example 9 was purified using a column chromatography using a medium in which hybridomas were cultured. Protein L Agarose (Thermo) column was used to purify the IgM type monoclonal antibody. Agarose was washed with PBS after the medium was released. The IgM monoclonal antibodies bound were eluted with 100 mM glycine buffer (pH 2.8) and then immediately neutralized by adding 1 M Tris-HCl buffer (pH 9.0). After dialysis with PBS, the antibody concentration was determined.

10.1. Isotyping Analysis of Monoclonal Antibody

In order to determine the immuno-isotype of the purified monoclonal antibody, a 96-well plate was first coated with anti-mouse IgM1, IgM2a, IgM2b, IgM3, IgM, IgA, Igκ and Igλ, and then was blocked with PBS supplemented with 10% FBS. Medium in which each hybridoma was grown or purified monoclonal antibody was added thereto. Then, they were reacted for a specified period of time and then reacted with the secondary antibody. The secondary antibody was an antibody conjugated with horseradish peroxidase. The reaction was identified at a wavelength of 450 nm. The results are shown in Table 6.

TABLE 6

| Type | Heavy chain | | | | | | Light chain | |
|---|---|---|---|---|---|---|---|---|
| | IgG | | | | | | | |
| MAb | G1 | G2a | G2b | G3 | IgM | IgA | κ | λ |
| OD7 | − | − | − | − | + | − | + | − |
| OD111-A | − | − | − | − | + | − | + | − |
| OD169-B | − | − | − | | + | | + | |
| OD184 | − | − | − | | + | | + | |
| OD185 | − | − | − | | + | | + | |
| OD196 | − | − | − | − | + | − | + | − |
| OD210-A | − | − | − | − | + | − | + | − |
| OD225 | − | − | − | | + | | + | |
| OD234 | − | − | − | − | + | − | − | + |
| OD241 | − | − | − | − | + | − | + | − |
| OD244 | − | − | − | − | + | − | + | − |
| OD270 | − | − | − | − | + | − | + | − |
| OD296 | − | − | − | − | + | − | + | − |
| OD298 | − | − | − | − | + | − | + | − |
| OD340 | − | − | − | − | + | − | + | − |

As shown in Table 6, it was confirmed that 15 kinds of IgM-type antibodies such as OD7, OD111A, OD169B, OD184, OD185, OD196, OD210A, OD225, OD234, OD241, OD244, OD270, OD296, OD298 and OD340 were obtained finally.

10.2 Measurement of Antibody Binding Affinity by Flow Cytometry

Flow cytometry analysis was performed on the cell-antibody reaction so as to identify whether the antibody prepared in Example 9 binds better to the surface of odontoblasts among the surfaces of hDPSCs and odontoblasts. More specifically, Enzyme Free Cell Dissociation Solution (Millipore) was added thereto, and they were cultured for 10 minutes. Then, they were detached from the culture dish to be collected.

About $3\times10^4$ cells of hDPSCs and odontoblasts were resuspended in PBS supplemented with 1% BSA (GeneDEPOT), and then hybridoma culture medium or purified monoclonal antibodies were added thereto. Then, the cells were reacted on ice for 1 hour. After washing, FITC-conjugated anti-mouse IgM (1,100, Santa Cruz) or PE-conjugated anti-mouse IgM (1,100, Santa Cruz) was added as a secondary antibody, and they were reacted on ice for 1 hour. The degree of binding of antibody binding to the cell surface was analyzed by FACS Calibur™ (BD Biosciences). Antibody binding affinity was quantified using Cell Quest pro and WinMDI program. Cells stained using only PE-conjugated anti-mouse IgM were used as a control group.

It was confirmed that all of the 15 kinds of IgM type antibodies were bound to highly expressed antigens in odontoblasts than in hDPSCs, or bound to antigens expressed on only odontoblasts. These results indicate that the 15 kinds of monoclonal antibodies specifically bind to surface antigens specifically expressed in human odontoblast so that they can be used for purely isolating odontoblasts.

Example 11. Analysis of Antibody Sequence

In order to analyze the gene sequences of the antibodies obtained in Example 9, primers for amplifying the heavy chain and light chain variable regions of the antibodies were synthesized according to the method disclosed in Wang et al., 2000 and the like. The sequences of the primers used are as follows. For other isotypes, suitable primers were synthesized to be used.

TABLE 7

| Heavy chain | |
|---|---|
| 5'MH1 | SAR GTN MAG CTG SAG SAG TC |
| 5'MH2 | SAR GTN MAG CTG SAG SAG TCW GG |
| IgA | 5'-GAT GGT GGG ATT TCT CGC AGA CTC-3' |
| IgE | 5'-TAA GGG GTA GAG CTG AGG GTT CCT G-3' |
| IgM | 5'-GAC ATT TGG GAA GGA CTG ACT CTC-3' |
| IgM1 | 5'-ATA GAC AGA TGG GGG TGT CGT TTT GGC-3' |
| IgM2a | 5'-CTT GAC CAG GCA TCC TAG AGT CA-3' |
| IgM2b | 5'-AGG GGC CAG TGG ATA GAC TGA TGG-3' |
| IgM3 | 5'-AGG GAC CAA GGG ATA GAC AGA TGG-3' |
| Light chain | |
| 5'MK | GAY ATT GTG MTS ACM CAR WCT MCA |
| 3'CK | GGA TAC AGT TGG TGC AGC ATC |

TABLE 7-continued

| | |
|---|---|
| Primer6 | GAC ATT GTG CTG ACC CAA TCT CCA GCT TCT |
| primer7 | GAC ATT CAG CTG ACC CAG TCT CCA |

The Easy-spin™ Total RNA Extraction kit (Intron) was used to collect hybridoma cells (up to $1\times10^6$ cells) and extract total RNA. The cDNA was synthesized at 45° C. for 30 minutes using Maxime RT-PCR PreMix Kit (Intron). RT-PCR reaction was performed by 1 cycle at 94° C. for 5 minutes, 30 cycles at 94° C. for 1 minute, 45° C. for 1 minute and 72° C. for 1 minute and a final cycle at 72° C. for 5 minutes. The amplified DNA fragment was cloned into pBluescript KS (+) vector, and its sequence was analyzed. The consensus domain of the antibody was analyzed according to Dr. Andrew C. R. Martin's Group database.

The CDR region is a site that recognizes and binds to a specific antigen. CDR1 and CDR2 are found in a variable region (V). For CDR3, a heavy chain includes a portion of V region, a diversity region (D) and a joining region (J), and light chain includes V, J regions. Sequence information of the IgM type antibody confirmed by analysis of sequences is illustrated in FIG. 12.

Further, the nucleotide sequences encoding the light and heavy chains of these individual antibodies are represented by SEQ ID NOS: 241 to 270.

The invention claimed is:

1. An odontoblast-specific IgG monoclonal antibody selected from the group consisting of a) an odontoblast-specific OD40 IgG antibody comprising a light chain variable region comprising a light chain CDR1 represented by SEQ ID NO: 1, a light chain CDR2 represented by SEQ ID NO: 2 and a light chain CDR3 represented by SEQ ID NO: 3 and a heavy chain variable region comprising a heavy chain CDR1 represented by SEQ ID NO: 4, a heavy chain CDR2 represented by SEQ ID NO: 5 and a heavy chain CDR3 represented by SEQ ID NO: 6, b) an odontoblast-specific OD46 IgG antibody comprising a light chain variable region comprising a light chain CDR1 represented by SEQ ID NO: 7, a light chain CDR2 represented by SEQ ID NO: 8 and a light chain CDR3 represented by SEQ ID NO: 9 and a heavy chain variable region comprising a heavy chain CDR1 represented by SEQ ID NO: 10, a heavy chain CDR2 represented by SEQ ID NO: 11 and a heavy chain CDR3 represented by SEQ ID NO: 12, c) an odontoblast-specific OD142B IgG antibody comprising a light chain variable region comprising a light chain CDR1 represented by SEQ ID NO: 19, a light chain CDR2 represented by SEQ ID NO: 20 and a light chain CDR3 represented by SEQ ID NO: 21 and a heavy chain variable region comprising a heavy chain CDR1 represented by SEQ ID NO: 22, a heavy chain CDR2 represented by SEQ ID NO: 23 and a heavy chain CDR3 represented by SEQ ID NO: 24, d) an odontoblast-specific OD149A IgG antibody comprising a light chain variable region comprising a light chain CDR1 represented by SEQ ID NO: 31, a light chain CDR2 represented by SEQ ID NO: 32 and a light chain CDR3 represented by SEQ ID NO: 33 and a heavy chain variable region comprising a heavy chain CDR1 represented by SEQ ID NO: 34, a heavy chain CDR2 represented by SEQ ID NO: 35 and a heavy chain CDR3 represented by SEQ ID NO: 36, and e) an odontoblast-specific OD238 IgG antibody comprising a light chain variable region comprising a light chain CDR1 represented by SEQ ID NO: 55, a light chain CDR2 represented by SEQ ID NO: 56 and a light chain CDR3 represented by SEQ ID NO: 57 and a heavy chain variable region comprising a heavy chain CDR1 represented by SEQ ID NO: 58, a heavy chain CDR2 represented by SEQ ID NO: 59 and a heavy chain CDR3 represented by SEQ ID NO: 60.

2. The antibody according to claim 1, wherein the OD40 IgG antibody comprises a light chain variable region represented by SEQ ID NO: 73 and a heavy chain variable region represented by SEQ ID NO: 74.

3. The antibody according to claim 2, wherein the light chain variable region of the OD40 IgG antibody is encoded by a nucleotide sequence represented by SEQ ID NO: 97 and the heavy chain variable region thereof is encoded by a nucleotide sequence represented by SEQ ID NO: 98.

4. The antibody according to claim 1, wherein the OD46 IgG antibody comprises a light chain variable region represented by SEQ ID NO: 75 and a heavy chain variable region represented by SEQ ID NO: 76.

5. The antibody according to claim 4, wherein the light chain variable region of the OD46 IgG antibody is encoded by a nucleotide sequence represented by SEQ ID NO: 99 and the heavy chain variable region thereof is encoded by a nucleotide sequence represented by SEQ ID NO: 100.

6. The antibody according to claim 1, wherein the OD142B IgG antibody comprises a light chain variable region represented by SEQ ID NO: 79 and a heavy chain variable region represented by SEQ ID NO: 80.

7. The antibody according to claim 6, wherein the light chain variable region of the OD142B IgG antibody is encoded by a nucleotide sequence represented by SEQ ID NO: 103 and the heavy chain variable region thereof is encoded by a nucleotide sequence represented by SEQ ID NO: 104.

8. The antibody according to claim 1, wherein the OD149A IgG antibody comprises a light chain variable region represented by SEQ ID NO: 83 and a heavy chain variable region represented by SEQ ID NO: 84.

9. The antibody according to claim 8, wherein the light chain variable region of the OD149A IgG antibody is encoded by a nucleotide sequence represented by SEQ ID NO: 107 and the heavy chain variable region thereof is encoded by a nucleotide sequence represented by SEQ ID NO: 108.

10. The antibody according to claim 1, wherein the OD238 IgG antibody comprises a light chain variable region represented by SEQ ID NO: 91 and a heavy chain variable region represented by SEQ ID NO: 92.

11. The antibody according to claim 10, wherein the light chain variable region of the OD238 IgG antibody is encoded by a nucleotide sequence represented by SEQ ID NO: 115 and the heavy chain variable region thereof is encoded by a nucleotide sequence represented by SEQ ID NO: 116.

12. A method for screening a substance which differentiates an undifferentiated dental pulp stem cell into an odontoblast, the method comprising:

a) treating the undifferentiated dental pulp stem cell with the odontoblast-specific IgG monoclonal antibody according to claim 1;

b) treating the undifferentiated dental pulp stem cell with a candidate substance; and c) treating the sample of b) step with the IgG monoclonal antibody according to claim 1 and comparing a binding reaction of a) step.

13. A composition for identifying a differentiated odontoblast or isolating an odontoblast, the composition comprising the odontoblast-specific IgG monoclonal antibody according to claim 1, and an odontoblast-specific IgG or IgM monoclonal antibody selected from the group consisting of a) an odontoblast-specific OD142D IgG antibody comprising a light chain variable region comprising a light chain CDR1 represented by SEQ ID NO: 25, a light chain CDR2 represented by SEQ ID NO: 26 and a light chain CDR3 represented by SEQ ID NO: 27 and a heavy chain variable region comprising a heavy chain CDR1 represented by SEQ ID NO: 28, a heavy chain CDR2 represented by SEQ ID NO: 29 and a heavy chain CDR3 represented by SEQ ID NO: 30, b) an odontoblast-specific OD82 IgG antibody comprising a light chain variable region comprising a light chain CDR1 represented by SEQ ID NO: 13, a light chain CDR2 represented by SEQ ID NO: 14 and a light chain CDR3 represented by SEQ ID NO: 15 and a heavy chain variable region comprising a heavy chain CDR1 represented by SEQ ID NO: 16, a heavy chain CDR2 represented by SEQ ID NO: 17 and a heavy chain CDR3 represented by SEQ ID NO: 18, c) an odontoblast-specific OD218A IgG antibody comprising a light chain variable region comprising a light chain CDR1 represented by SEQ ID NO: 37, a light chain CDR2 represented by SEQ ID NO: 38 and a light chain CDR3 represented by SEQ ID NO: 39 and a heavy chain variable region comprising a heavy chain CDR1 represented by SEQ ID NO: 40, a heavy chain CDR2 represented by SEQ ID NO: 41 and a heavy chain CDR3 represented by SEQ ID NO: 42, d) an odontoblast-specific OD218B IgG antibody comprising a light chain variable region comprising a light chain CDR1 represented by SEQ ID NO: 43, a light chain CDR2 represented by SEQ ID NO: 44 and a light chain CDR3 represented by SEQ ID NO: 45 and a heavy chain variable region comprising a heavy chain CDR1 represented by SEQ ID NO: 46, a heavy chain CDR2 represented by SEQ ID NO: 47 and a heavy chain CDR3 represented by SEQ ID NO: 48, e) an odontoblast-specific OD228 IgG antibody comprising a light chain variable region comprising a light chain CDR1 represented by SEQ ID NO: 49, a light chain CDR2 represented by SEQ ID NO: 50 and a light chain CDR3 represented by SEQ ID NO: 51 and a heavy chain variable region comprising a heavy chain CDR1 represented by SEQ ID NO: 52, a heavy chain CDR2 represented by SEQ ID NO: 53 and a heavy chain CDR3 represented by SEQ ID NO: 54, f) an odontoblast-specific OD243A IgG antibody comprising a light chain variable region comprising a light chain CDR1 represented by SEQ ID NO: 61, a light chain CDR2 represented by SEQ ID NO: 62 and a light chain CDR3 represented by SEQ ID NO: 63 and a heavy chain variable region comprising a heavy chain CDR1 represented by SEQ ID NO: 64, a heavy chain CDR2 represented by SEQ ID NO: 65 and a heavy chain CDR3 represented by SEQ ID NO: 66, g) an odontoblast-specific OD256 IgG antibody comprising a light chain variable region comprising a light chain CDR1 represented by SEQ ID NO: 67, a light chain CDR2 represented by SEQ ID NO: 68 and a light chain CDR3 represented by SEQ ID NO: 69 and a heavy chain variable region comprising a heavy chain CDR1 represented by SEQ ID NO: 70, a heavy chain CDR2 represented by SEQ ID NO: 71 and a heavy chain CDR3 represented by SEQ ID NO: 72, h) an odontoblast-specific OD7 IgM antibody comprising a light chain variable region comprising a light chain CDR1 represented by SEQ ID NO: 121, a light chain CDR2 represented by SEQ ID NO: 122 and a light chain CDR3 represented by SEQ ID NO: 123 and a heavy chain variable region comprising a heavy chain CDR1 represented by SEQ ID NO: 124, a heavy chain CDR2 represented by SEQ ID NO: 125 and a heavy chain CDR3 represented by SEQ ID NO: 126, i) an odontoblast-specific OD111A IgM antibody comprising a light chain variable region comprising a light chain CDR1 represented by SEQ ID NO: 127, a light chain CDR2 represented by SEQ ID NO: 128 and a light chain CDR3 represented by SEQ ID NO: 129 and a heavy chain variable region comprising a heavy chain CDR1 represented by SEQ ID NO: 130, a heavy chain CDR2 represented by SEQ ID NO: 131 and a heavy chain CDR3 represented by SEQ ID NO: 132, j) an odontoblast-specific OD169B IgM antibody comprising a light chain variable region comprising a light chain CDR1 represented by SEQ ID NO: 133, a light chain CDR2 represented by SEQ ID NO: 134 and a light chain CDR3 represented by SEQ ID NO: 135 and a heavy chain variable region comprising a heavy chain CDR1 represented by SEQ ID NO: 136, a heavy chain CDR2 represented by SEQ ID NO: 137 and a heavy chain CDR3 represented by SEQ ID NO: 138, k) an odontoblast-specific OD184 IgM antibody comprising a light chain variable region comprising a light chain CDR1 represented by SEQ ID NO: 139, a light chain CDR2 represented by SEQ ID NO: 140 and a light chain CDR3 represented by SEQ ID NO: 141 and a heavy chain variable region comprising a heavy chain CDR1 represented by SEQ ID NO: 142, a heavy chain CDR2 represented by SEQ ID NO: 143 and a heavy chain CDR3 represented by SEQ ID NO: 144, l) an odontoblast-specific OD185 IgM antibody comprising a light chain variable region comprising a light chain CDR1 represented by SEQ ID NO: 145, a light chain CDR2 represented by SEQ ID NO: 146 and a light chain CDR3 represented by SEQ ID NO: 147 and a heavy chain variable region comprising a heavy chain CDR1 represented by SEQ ID NO: 148, a heavy chain CDR2 represented by SEQ ID NO: 149 and a heavy chain CDR3 represented by SEQ ID NO: 150, m) an odontoblast-specific OD196 IgM antibody comprising a light chain variable region comprising a light chain CDR1 represented by SEQ ID NO: 151, a light chain CDR2 represented by SEQ ID NO: 152 and a light chain CDR3 represented by SEQ ID NO: 153 and a heavy chain variable region comprising a heavy chain CDR1 represented by SEQ ID NO: 154, a heavy chain CDR2 represented by SEQ ID NO: 155 and a heavy chain CDR3 represented by SEQ ID NO: 156, n) an odontoblast-specific OD210A IgM antibody comprising a light chain variable region comprising a light chain CDR1 represented by SEQ ID NO: 157, a light chain CDR2 represented by SEQ ID NO: 158 and a light chain CDR3 represented by SEQ ID NO: 159 and a heavy chain variable region comprising a heavy chain CDR1 represented by SEQ ID NO: 160, a heavy chain CDR2 represented by SEQ ID NO: 161 and a heavy chain CDR3 represented by SEQ ID NO: 162, o) an odontoblast-specific OD225 IgM antibody comprising a light chain variable region comprising a light chain CDR1 represented by SEQ ID NO: 163, a light chain CDR2 represented by SEQ ID NO: 164 and a light chain CDR3 represented by SEQ ID NO: 165 and a heavy chain variable region comprising a heavy chain CDR1 represented by SEQ ID NO: 166, a heavy chain CDR2 represented by SEQ ID NO: 167 and a heavy chain CDR3 represented by SEQ ID NO: 168, p) an odontoblast-specific OD234 IgM antibody comprising a light chain variable region comprising a light chain CDR1 represented by SEQ ID NO: 169, a light chain CDR2 represented by SEQ ID NO: 170 and a light chain CDR3 represented by SEQ ID NO: 171 and a heavy chain variable region comprising a heavy chain CDR1 represented by SEQ ID NO: 172, a heavy chain CDR2 represented by SEQ ID NO: 173 and a heavy chain CDR3 represented by SEQ ID NO: 174, q) an odontoblast-specific OD241 IgM antibody comprising a light chain variable region comprising a light chain CDR1 represented by SEQ ID NO: 175, a light chain CDR2 represented by SEQ ID NO: 176 and a light chain CDR3 represented by SEQ ID NO: 177 and a heavy chain variable region comprising a heavy chain CDR1 represented by SEQ ID NO: 178, a heavy chain CDR2 represented by SEQ ID NO: 179 and a heavy chain CDR3 represented by SEQ ID NO: 180, r) an odontoblast-specific OD244 IgM antibody comprising a light chain variable region comprising a light chain CDR1 represented by SEQ ID NO: 181, a light chain CDR2 represented by SEQ ID NO: 182 and a light chain CDR3 represented by SEQ ID NO: 183 and a heavy chain variable region comprising a heavy chain CDR1 represented by SEQ ID NO: 184, a heavy chain CDR2 represented by SEQ ID NO: 185 and a heavy chain CDR3 represented by SEQ ID NO: 186, s) an odontoblast-specific OD270 IgM antibody comprising a light chain variable region comprising a light chain CDR1 represented by SEQ ID NO: 187, a light chain CDR2 represented by SEQ ID NO: 188 and a light chain CDR3 represented by SEQ ID NO: 189 and a heavy chain variable region comprising a heavy chain CDR1 represented by SEQ ID NO: 190, a heavy chain CDR2 represented by SEQ ID NO: 191 and a heavy chain CDR3 represented by SEQ ID NO: 192, t) an odontoblast-specific OD296 IgM antibody comprising a light chain variable region comprising a light chain CDR1 represented by SEQ ID NO: 193, a light chain CDR2 represented by SEQ ID NO: 194 and a light chain CDR3 represented by SEQ ID NO: 195 and a heavy chain variable region comprising a heavy chain CDR1 represented by SEQ ID NO: 196, a heavy chain CDR2 represented by SEQ ID NO: 197 and a heavy chain CDR3 represented by SEQ ID NO: 198, u) an odontoblast-specific OD298 IgM antibody comprising a light chain variable region comprising a light chain CDR1 represented by SEQ ID NO: 199, a light chain CDR2 represented by SEQ ID NO: 200 and a light chain CDR3 represented by SEQ ID NO: 201 and a heavy chain variable region comprising a heavy chain CDR1 represented by SEQ ID NO: 202, a heavy chain CDR2 represented by SEQ ID NO: 203 and a heavy chain CDR3 represented by SEQ ID NO: 204, and v) an odontoblast-specific OD340 IgM antibody comprising a light chain variable region comprising a light chain CDR1 represented by SEQ ID NO: 205, a light chain CDR2 represented by SEQ ID NO: 206 and a light chain CDR3 represented by SEQ ID NO: 207 and a heavy chain variable region comprising a heavy chain CDR1 represented by SEQ ID NO: 208, a heavy chain CDR2 represented by SEQ ID NO: 209 and a heavy chain CDR3 represented by SEQ ID NO: 210.

14. A kit for identifying a differentiated odontoblast or isolating an odontoblast, the kit comprising: a culture plate for culturing a target cell to induce differentiation into an odontoblast or a reagent capable of evaluating the state of the differentiation into an odontoblast; the odontoblast-specific IgG monoclonal antibody according to claim 1; and an odontoblast-specific IgG or IgM monoclonal antibody selected from the group consisting of a) an odontoblast-specific OD142D IgG antibody including a light chain variable region including a light chain CDR1 represented by SEQ ID NO: 25, a light chain CDR2 represented by SEQ ID NO: 26 and a light chain CDR3 represented by SEQ ID NO: 27 and a heavy chain variable region including a heavy chain CDR1 represented by SEQ ID NO: 28, a heavy chain CDR2 represented by SEQ ID NO: 29 and a heavy chain CDR3 represented by SEQ ID NO: 30, b) an odontoblast-specific OD82 IgG antibody comprising a light chain variable region comprising a light chain CDR1 represented by SEQ ID NO: 13, a light chain CDR2 represented by SEQ ID NO: 14 and a light chain CDR3 represented by SEQ ID NO: 15 and a heavy chain variable region comprising a heavy chain CDR1 represented by SEQ ID NO: 16, a heavy chain CDR2 represented by SEQ ID NO: 17 and a heavy chain CDR3 represented by SEQ ID NO: 18, c) an odontoblast-specific OD218A IgG antibody comprising a light chain variable region comprising a light chain CDR1 represented by SEQ ID NO: 37, a light chain CDR2 represented by SEQ ID NO: 38 and a light chain CDR3 represented by SEQ ID NO: 39 and a heavy chain variable region comprising a heavy chain CDR1 represented by SEQ ID NO: 40, a heavy chain CDR2 represented by SEQ ID NO: 41 and a heavy chain CDR3 represented by SEQ ID NO: 42, d) an odontoblast-specific OD218B IgG antibody comprising a light chain variable region comprising a light chain CDR1 represented by SEQ ID NO: 43, a light chain CDR2 represented by SEQ ID NO: 44 and a light chain CDR3 represented by SEQ ID NO: 45 and a heavy chain variable region comprising a heavy chain CDR1 represented by SEQ ID NO: 46, a heavy chain CDR2 represented by SEQ ID NO: 47 and a heavy chain CDR3 represented by SEQ ID NO: 48, e) an odontoblast-specific OD228 IgG antibody comprising a light chain variable region comprising a light chain CDR1 represented by SEQ ID NO: 49, a light chain CDR2 represented by SEQ ID NO: 50 and a light chain CDR3 represented by SEQ ID NO: 51 and a heavy chain variable region comprising a heavy chain CDR1 represented by SEQ ID NO: 52, a heavy chain CDR2 represented by SEQ ID NO: 53 and a heavy chain CDR3 represented by SEQ ID NO: 54, f) an odontoblast-specific OD243A IgG antibody comprising a light chain variable region comprising a light chain CDR1 represented by SEQ ID NO: 61, a light chain CDR2 represented by SEQ ID NO: 62 and a light chain CDR3 represented by SEQ ID NO: 63 and a heavy chain variable region comprising a heavy chain CDR1 represented by SEQ ID NO: 64, a heavy chain CDR2 represented by SEQ ID NO: 65 and a heavy chain CDR3 represented by SEQ ID NO: 66, g) an odontoblast-specific OD256 IgG antibody comprising a light chain variable region comprising a light chain CDR1 represented by SEQ ID NO: 67, a light chain CDR2 represented by SEQ ID NO: 68 and a light chain CDR3 represented by SEQ ID NO: 69 and a heavy chain variable region comprising a heavy chain CDR1 represented by SEQ ID NO: 70, a heavy chain CDR2 represented by SEQ ID NO: 71 and a heavy chain CDR3 represented by SEQ ID NO: 72, h) an odontoblast-specific OD7 IgM antibody comprising a light chain variable region comprising a light chain CDR1 represented by SEQ ID NO: 121, a light chain CDR2 represented by SEQ ID NO: 122 and a light chain CDR3 represented by SEQ ID NO: 123 and a heavy chain variable region comprising a heavy chain CDR1 represented by SEQ ID NO: 124, a heavy chain CDR2 represented by SEQ ID NO: 125 and a heavy chain CDR3 represented by SEQ ID NO: 126, i) an odontoblast-specific OD111A IgM antibody comprising a light chain variable region comprising a light chain CDR1 represented by SEQ ID NO: 127, a light chain CDR2 represented by SEQ ID NO: 128 and a light chain CDR3 represented by SEQ ID NO: 129 and a heavy chain variable region comprising a heavy chain CDR1 represented by SEQ ID NO: 130, a heavy chain CDR2 represented by SEQ ID NO: 131 and a heavy chain CDR3 represented by SEQ ID NO: 132, j) an odontoblast-specific OD169B IgM antibody comprising a light chain variable region comprising a light chain CDR1 represented by SEQ ID NO: 133, a light chain CDR2 represented by SEQ ID NO: 134 and a light chain CDR3 represented by SEQ ID NO: 135 and a heavy chain variable region comprising a heavy chain CDR1 represented by SEQ ID NO: 136, a heavy chain CDR2 represented by SEQ ID NO: 137 and a heavy chain CDR3 represented by SEQ ID NO: 138, k) an odontoblast-specific OD184 IgM antibody comprising a light chain variable region comprising a light chain CDR1 represented by SEQ ID NO: 139, a light chain CDR2 represented by SEQ ID NO: 140 and a light chain CDR3 represented by SEQ ID NO: 141 and a heavy chain variable region comprising a heavy chain CDR1 represented by SEQ ID NO: 142, a heavy chain CDR2 represented by SEQ ID NO: 143 and a heavy chain CDR3 represented by SEQ ID NO: 144, l) an odontoblast-specific OD185 IgM antibody comprising a light chain variable region comprising a light chain CDR1 represented by SEQ ID NO: 145, a light chain CDR2 represented by SEQ ID NO: 146 and a light chain CDR3 represented by SEQ ID NO: 147 and a heavy chain variable region comprising a heavy chain CDR1 represented by SEQ ID NO: 148, a heavy chain CDR2 represented by SEQ ID NO: 149 and a heavy chain CDR3 represented by SEQ ID NO: 150, m) an odontoblast-specific OD196 IgM antibody comprising a light chain variable region comprising a light chain CDR1 represented by SEQ ID NO: 151, a light chain CDR2 represented by SEQ ID NO: 152 and a light chain CDR3 represented by SEQ ID NO: 153 and a heavy chain variable region comprising a heavy chain CDR1 represented by SEQ ID NO: 154, a heavy chain CDR2 represented by SEQ ID NO: 155 and a heavy chain CDR3 represented by SEQ ID NO: 156, n) an odontoblast-specific OD210A IgM antibody comprising a light chain variable region comprising a light chain CDR1 represented by SEQ ID NO: 157, a light chain CDR2 represented by SEQ ID NO: 158 and a light chain CDR3 represented by SEQ ID NO: 159 and a heavy chain variable region comprising a heavy chain CDR1 represented by SEQ ID NO: 160, a heavy chain CDR2 represented by SEQ ID NO: 161 and a heavy chain CDR3 represented by SEQ ID NO: 162, o) an odontoblast-specific OD225 IgM antibody comprising a light chain variable region comprising a light chain CDR1 represented by SEQ ID NO: 163, a light chain CDR2 represented by SEQ ID NO: 164 and a light chain CDR3 represented by SEQ ID NO: 165 and a heavy chain variable region comprising a heavy chain CDR1 represented by SEQ ID NO: 166, a heavy chain CDR2 represented by SEQ ID NO: 167 and a heavy chain CDR3 represented by SEQ ID NO: 168, p) an odontoblast-specific OD234 IgM antibody comprising a light chain variable region comprising a light chain CDR1 represented by SEQ ID NO: 169, a light chain CDR2 represented by SEQ ID NO: 170 and a light chain CDR3 represented by SEQ ID NO: 171 and a heavy chain variable region comprising a heavy chain CDR1 represented by SEQ ID NO: 172, a heavy chain CDR2 represented by SEQ ID NO: 173 and a heavy chain CDR3 represented by SEQ ID NO: 174, q) an odontoblast-specific OD241 IgM antibody comprising a light chain variable region comprising a light chain CDR1 represented by SEQ ID NO: 175, a light chain CDR2 represented by SEQ ID NO: 176 and a light chain CDR3 represented by SEQ ID NO: 177 and a heavy chain variable region comprising a heavy chain CDR1 represented by SEQ ID NO: 178, a heavy chain CDR2 represented by SEQ ID NO: 179 and a heavy chain CDR3 represented by SEQ ID NO: 180, r) an odontoblast-specific OD244 IgM antibody comprising a light chain variable region comprising a light chain CDR1 represented by SEQ ID NO: 181, a light chain CDR2 represented by SEQ ID NO: 182 and a light chain CDR3 represented by SEQ ID NO: 183 and a heavy chain variable region comprising a heavy chain CDR1 represented by SEQ ID NO: 184, a heavy chain CDR2 represented by SEQ ID NO: 185 and a heavy chain CDR3 represented by SEQ ID NO: 186, s) an odontoblast-specific OD270 IgM antibody comprising a light chain variable region comprising a light chain CDR1 represented by SEQ ID NO: 187, a light chain CDR2 represented by SEQ ID NO: 188 and a light chain CDR3 represented by SEQ ID NO: 189 and a heavy chain variable region comprising a heavy chain CDR1 represented by SEQ ID NO: 190, a heavy chain CDR2 represented by SEQ ID NO: 191 and a heavy chain CDR3 represented by SEQ ID NO: 192, t) an odontoblast-specific OD296 IgM antibody comprising a light chain variable region comprising a light chain CDR1 represented by SEQ ID NO: 193, a light chain CDR2 represented by SEQ ID NO: 194 and a light chain CDR3 represented by SEQ ID NO: 195 and a heavy chain variable region comprising a heavy chain CDR1 represented by SEQ ID NO: 196, a heavy chain CDR2 represented by SEQ ID NO: 197 and a heavy chain CDR3 represented by SEQ ID NO: 198, u) an odontoblast-specific OD298 IgM antibody comprising a light chain variable region comprising a light chain CDR1 represented by SEQ ID NO: 199, a light chain CDR2 represented by SEQ ID NO: 200 and a light chain CDR3 represented by SEQ ID NO: 201 and a heavy chain variable region comprising a heavy chain CDR1 represented by SEQ ID NO: 202, a heavy chain CDR2 represented by SEQ ID NO: 203 and a heavy chain CDR3 represented by SEQ ID NO: 204, and v) an odontoblast-specific OD340 IgM antibody comprising a light chain variable region comprising a light chain CDR1 represented by SEQ ID NO: 205, a light chain CDR2 represented by SEQ ID NO: 206 and a light chain CDR3 represented by SEQ ID NO: 207 and a heavy chain variable region comprising a heavy chain CDR1 represented by SEQ ID NO: 208, a heavy chain CDR2 represented by SEQ ID NO: 209 and a heavy chain CDR3 represented by SEQ ID NO: 210.

* * * * *